(12) United States Patent
Thommen et al.

(10) Patent No.: US 11,950,766 B2
(45) Date of Patent: *Apr. 9, 2024

(54) SURGICAL VISUALIZATION SYSTEMS AND RELATED METHODS

(71) Applicant: MEDOS INTERNATIONAL SARL, Le Locle (CH)

(72) Inventors: Daniel Thommen, Liestal (CH); Judith Flock, Basel (CH); Veronique Christine Zollmann, Gebenstorf (CH); William Kane, Newport Beach, CA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 75 days.

This patent is subject to a terminal disclaimer.

(21) Appl. No.: 17/728,967

(22) Filed: Apr. 25, 2022

(65) Prior Publication Data
US 2022/0249125 A1 Aug. 11, 2022

Related U.S. Application Data

(63) Continuation of application No. 15/692,845, filed on Aug. 31, 2017, now Pat. No. 11,331,090, which is a
(Continued)

(51) Int. Cl.
*A61B 1/12* (2006.01)
*A61B 1/00* (2006.01)
(Continued)

(52) U.S. Cl.
CPC .......... *A61B 1/051* (2013.01); *A61B 1/00045* (2013.01); *A61B 1/00089* (2013.01);
(Continued)

(58) Field of Classification Search
CPC ............ A61B 1/00089; A61B 1/00091; A61B 1/00103; A61B 1/00128; A61B 1/00133;
(Continued)

(56) References Cited

U.S. PATENT DOCUMENTS 4,132,227 A 1/1979 Ibe
4,318,401 A 3/1982 Zimmerman
(Continued)

FOREIGN PATENT DOCUMENTS

CN 2659368 Y 12/2004
CN 1735380 A 2/2006
(Continued)

OTHER PUBLICATIONS

U.S. Appl. No. 18/479,048, filed Sep. 30, 2023, Surgical Visualization Systems and Related Methods.
(Continued)

*Primary Examiner* — Samuel S Hanna
(74) *Attorney, Agent, or Firm* — Barnes & Thornburg LLP

(57) ABSTRACT

Surgical visualization systems and related methods are disclosed herein, e.g., for providing visualization during surgical procedures. Systems and methods herein can be used in a wide range of surgical procedures, including spinal surgeries such as minimally-invasive fusion or discectomy procedures. Systems and methods herein can include various features for enhancing end user experience, improving clinical outcomes, or reducing the invasiveness of a surgery. Exemplary features can include access port integration, hands-free operation, active and/or passive lens cleaning, adjustable camera depth, and many others.

12 Claims, 29 Drawing Sheets

Related U.S. Application Data continuation-in-part of application No. 15/437,792, filed on Feb. 21, 2017, now Pat. No. 10,874,425, which is a continuation-in-part of application No. 15/254,877, filed on Sep. 1, 2016, now Pat. No. 10,987,129.

(60) Provisional application No. 62/468,475, filed on Mar. 8, 2017, provisional application No. 62/214,297, filed on Sep. 4, 2015.

(51) Int. Cl.

| | | |
|---|---|---|
| *A61B 1/012* | (2006.01) | |
| *A61B 1/018* | (2006.01) | |
| *A61B 1/05* | (2006.01) | |
| *A61B 1/055* | (2006.01) | |
| *A61B 1/07* | (2006.01) | |
| *A61B 1/233* | (2006.01) | |
| *A61B 1/267* | (2006.01) | |
| *A61B 1/313* | (2006.01) | |
| *A61B 1/317* | (2006.01) | |
| *A61B 1/32* | (2006.01) | |
| *A61B 5/00* | (2006.01) | |
| *A61B 5/06* | (2006.01) | |
| *A61B 5/24* | (2021.01) | |
| *A61B 17/00* | (2006.01) | |
| *A61B 17/02* | (2006.01) | |
| *A61B 17/32* | (2006.01) | |
| *A61B 17/34* | (2006.01) | |
| *A61B 17/60* | (2006.01) | |
| *A61B 17/70* | (2006.01) | |
| *A61B 18/18* | (2006.01) | |
| *A61B 90/00* | (2016.01) | |
| *A61B 90/50* | (2016.01) | |
| *A61B 90/57* | (2016.01) | |
| *A61F 2/44* | (2006.01) | |
| *A61F 2/46* | (2006.01) | |
| *A61B 17/16* | (2006.01) | |
| *A61B 17/17* | (2006.01) | |
| *A61B 17/56* | (2006.01) | |
| *A61B 18/00* | (2006.01) | |
| *A61B 34/00* | (2016.01) | |
| *A61B 34/20* | (2016.01) | |
| *A61B 34/30* | (2016.01) | |
| *A61B 90/30* | (2016.01) | |

(52) U.S. Cl.
CPC ...... *A61B 1/00091* (2013.01); *A61B 1/00094* (2013.01); *A61B 1/00096* (2013.01); *A61B 1/00103* (2013.01); *A61B 1/00128* (2013.01); *A61B 1/00133* (2013.01); *A61B 1/00135* (2013.01); *A61B 1/00154* (2013.01); *A61B 1/012* (2013.01); *A61B 1/018* (2013.01); *A61B 1/05* (2013.01); *A61B 1/055* (2013.01); *A61B 1/07* (2013.01); *A61B 1/126* (2013.01); *A61B 1/233* (2013.01); *A61B 1/2676* (2013.01); *A61B 1/3132* (2013.01); *A61B 1/3135* (2013.01); *A61B 1/317* (2013.01); *A61B 1/32* (2013.01); *A61B 5/068* (2013.01); *A61B 5/24* (2021.01); *A61B 5/4041* (2013.01); *A61B 5/407* (2013.01); *A61B 17/00234* (2013.01); *A61B 17/0218* (2013.01); *A61B 17/025* (2013.01); *A61B 17/0293* (2013.01); *A61B 17/320068* (2013.01); *A61B 17/3421* (2013.01); *A61B 17/3423* (2013.01); *A61B 17/3462* (2013.01); *A61B 17/60* (2013.01); *A61B 17/7032* (2013.01); *A61B 17/7074* (2013.01); *A61B 17/708* (2013.01); *A61B 18/1815* (2013.01); *A61B 90/03* (2016.02); *A61B 90/361* (2016.02); *A61B 90/50* (2016.02); *A61B 90/57* (2016.02); *A61F 2/4455* (2013.01); *A61F 2/4611* (2013.01); *A61B 1/00149* (2013.01); *A61B 2017/00261* (2013.01); *A61B 2017/00314* (2013.01); *A61B 2017/0034* (2013.01); *A61B 2017/00345* (2013.01); *A61B 2017/00407* (2013.01); *A61B 2017/00477* (2013.01); *A61B 2017/00557* (2013.01); *A61B 2017/00738* (2013.01); *A61B 2017/00831* (2013.01); *A61B 2017/00858* (2013.01); *A61B 2017/00871* (2013.01); *A61B 2017/00946* (2013.01); *A61B 2017/00991* (2013.01); *A61B 17/0206* (2013.01); *A61B 2017/0256* (2013.01); *A61B 2017/0262* (2013.01); *A61B 17/1637* (2013.01); *A61B 17/1671* (2013.01); *A61B 17/1703* (2013.01); *A61B 17/1757* (2013.01); *A61B 2017/320075* (2017.08); *A61B 17/3403* (2013.01); *A61B 17/3439* (2013.01); *A61B 2017/3443* (2013.01); *A61B 2017/3445* (2013.01); *A61B 2017/3447* (2013.01); *A61B 2017/345* (2013.01); *A61B 2017/3454* (2013.01); *A61B 2017/347* (2013.01); *A61B 2017/3484* (2013.01); *A61B 2017/564* (2013.01); *A61B 17/70* (2013.01); *A61B 17/7083* (2013.01); *A61B 2018/00339* (2013.01); *A61B 2018/00565* (2013.01); *A61B 2018/00577* (2013.01); *A61B 2018/1861* (2013.01); *A61B 2018/1869* (2013.01); *A61B 2034/2055* (2016.02); *A61B 34/30* (2016.02); *A61B 34/70* (2016.02); *A61B 2090/034* (2016.02); *A61B 2090/036* (2016.02); *A61B 2090/08021* (2016.02); *A61B 90/30* (2016.02); *A61B 2090/306* (2016.02); *A61B 2090/371* (2016.02); *A61B 2090/3983* (2016.02); *A61B 2218/002* (2013.01); *A61B 2218/007* (2013.01); *A61F 2002/4635* (2013.01)

(58) Field of Classification Search
CPC ..... A61B 1/00135; A61B 1/012; A61B 1/018; A61B 1/233; A61B 1/2676; A61B 1/3132; A61B 1/3135; A61B 1/317; A61B 1/32; A61B 17/00234; A61B 17/0206; A61B 17/0218; A61B 17/3421; A61B 17/3423; A61B 2018/1861; A61B 2018/1869; A61B 1/00094; A61B 1/126; A61B 2218/002; A61B 2218/007; A61B 1/051; A61B 1/05; A61B 1/055; A61B 90/361; A61F 2002/4635

See application file for complete search history.

(56) References Cited

U.S. PATENT DOCUMENTS

| | | |
|---|---|---|
| 4,573,448 A | 3/1986 | Kambin |
| 4,646,738 A | 3/1987 | Trott |
| 4,678,459 A | 7/1987 | Onik et al. |
| 4,807,593 A | 2/1989 | Ito |
| 4,863,430 A | 9/1989 | Klyce et al. |
| 4,874,375 A | 10/1989 | Ellison |
| 4,888,146 A | 12/1989 | Dandeneau |
| 5,080,662 A | 1/1992 | Paul |
| 5,195,541 A | 3/1993 | Obenchain |
| 5,207,213 A | 5/1993 | Auhll et al. |
| 5,285,795 A | 2/1994 | Ryan et al. |

(56) References Cited

U.S. PATENT DOCUMENTS

| | | |
|---|---|---|
| 5,395,317 A | 3/1995 | Kambin |
| 5,439,464 A | 8/1995 | Shapiro |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |
| 5,615,690 A | 4/1997 | Giurtino et al. |
| 5,618,293 A | 4/1997 | Sample et al. |
| 5,662,300 A | 9/1997 | Michelson |
| 5,688,222 A | 11/1997 | Hluchy et al. |
| 5,697,888 A | 12/1997 | Kobayashi et al. |
| 5,730,754 A | 3/1998 | Obenchain |
| 5,733,242 A | 3/1998 | Rayburn et al. |
| 5,735,792 A | 4/1998 | Vanden Hoek et al. |
| 5,749,602 A | 5/1998 | Delaney et al. |
| 5,792,044 A | 8/1998 | Foley et al. |
| 5,820,623 A | 10/1998 | Ng |
| 5,885,300 A | 3/1999 | Tokuhashi et al. |
| 5,894,369 A | 4/1999 | Akiba et al. |
| 5,899,425 A | 5/1999 | Corey, Jr. et al. |
| 5,928,137 A | 7/1999 | Green |
| 5,954,635 A | 9/1999 | Foley et al. |
| 5,976,075 A | 11/1999 | Beane et al. |
| 5,989,183 A | 11/1999 | Reisdorf et al. |
| 6,017,333 A | 1/2000 | Bailey |
| 6,033,105 A | 3/2000 | Barker et al. |
| 6,053,907 A | 4/2000 | Zirps |
| 6,063,021 A | 5/2000 | Hossain et al. |
| 6,110,182 A | 8/2000 | Mowlai-Ashtiani |
| 6,126,592 A | 10/2000 | Proch et al. |
| 6,139,563 A | 10/2000 | Cosgrove, III et al. |
| 6,200,322 B1 | 3/2001 | Branch et al. |
| 6,217,509 B1 | 4/2001 | Foley et al. |
| 6,234,961 B1 | 5/2001 | Gray |
| 6,283,966 B1 | 9/2001 | Houfburg |
| 6,286,179 B1 | 9/2001 | Byrne |
| 6,296,644 B1 | 10/2001 | Saurat et al. |
| 6,322,498 B1 | 11/2001 | Gravenstein et al. |
| 6,354,992 B1 | 3/2002 | Kato |
| 6,357,710 B1 | 3/2002 | Fielden et al. |
| 6,371,968 B1 | 4/2002 | Kogasaka et al. |
| 6,383,191 B1 | 5/2002 | Zdeblick et al. |
| 6,447,446 B1 | 9/2002 | Smith et al. |
| 6,468,289 B1 | 10/2002 | Bonutti |
| 6,520,495 B1 | 2/2003 | La Mendola |
| 6,558,407 B1 | 5/2003 | Ivanko et al. |
| 6,575,899 B1 | 6/2003 | Foley et al. |
| 6,579,281 B2 | 6/2003 | Palmer et al. |
| 6,596,008 B1 | 7/2003 | Kambin |
| 6,626,830 B1 | 9/2003 | Califiore et al. |
| 6,648,915 B2 | 11/2003 | Sazy |
| 6,663,563 B1 | 12/2003 | Sharratt |
| 6,676,597 B2 | 1/2004 | Guenst et al. |
| 6,679,833 B2 | 1/2004 | Smith et al. |
| 6,685,724 B1 | 2/2004 | Haluck |
| 6,688,564 B2 | 2/2004 | Salvermoser et al. |
| 6,758,809 B2 | 7/2004 | Briscoe et al. |
| 6,808,505 B2 | 10/2004 | Kadan |
| 6,887,198 B2 | 5/2005 | Phillips et al. |
| 6,983,930 B1 | 1/2006 | La Mendola et al. |
| 7,001,342 B2 | 2/2006 | Faciszewski |
| 7,087,058 B2 | 8/2006 | Cragg |
| 7,104,986 B2 | 9/2006 | Hovda et al. |
| 7,137,949 B2 | 11/2006 | Scirica et al. |
| 7,179,261 B2 | 2/2007 | Sicvol et al. |
| 7,182,731 B2 | 2/2007 | Nguyen et al. |
| 7,226,413 B2 | 6/2007 | McKinley |
| 7,341,556 B2 | 3/2008 | Shalman |
| 7,434,325 B2 | 10/2008 | Foley et al. |
| 7,491,168 B2 | 2/2009 | Raymond et al. |
| 7,591,790 B2 | 9/2009 | Pflueger |
| 7,594,888 B2 | 9/2009 | Raymond et al. |
| 7,618,431 B2 | 11/2009 | Roehm, III et al. |
| 7,636,596 B2 | 12/2009 | Solar |
| 7,637,905 B2 | 12/2009 | Saadat et al. |
| 7,641,659 B2 | 1/2010 | Emstad et al. |
| 7,766,313 B2 | 8/2010 | Panosian |
| 7,771,384 B2 | 8/2010 | Ravo |
| 7,794,456 B2 | 9/2010 | Sharps et al. |
| 7,794,469 B2 | 9/2010 | Kao et al. |
| 7,811,303 B2 | 10/2010 | Fallin et al. |
| 7,931,579 B2 | 4/2011 | Bertolero et al. |
| 7,946,981 B1 | 5/2011 | Cubb |
| 7,951,141 B2 | 5/2011 | Sharps et al. |
| 7,959,564 B2 | 6/2011 | Ritland |
| 7,988,623 B2 | 8/2011 | Pagliuca et al. |
| 8,007,492 B2 | 8/2011 | DiPoto et al. |
| 8,038,606 B2 | 10/2011 | Otawara |
| 8,043,381 B2 | 10/2011 | Hestad et al. |
| 8,062,218 B2 | 11/2011 | Sebastian et al. |
| 8,079,952 B2 | 12/2011 | Fujimoto |
| 8,092,464 B2 | 1/2012 | McKay |
| 8,096,944 B2 | 1/2012 | Harrel |
| 8,202,216 B2 | 6/2012 | Melkent et al. |
| 8,206,357 B2 | 6/2012 | Bettuchi |
| 8,230,863 B2 | 7/2012 | Ravikumar et al. |
| 8,236,006 B2 | 8/2012 | Hamada |
| 8,267,896 B2 | 9/2012 | Hartoumbekis et al. |
| 8,303,492 B2 | 11/2012 | Ito |
| 8,333,690 B2 | 12/2012 | Ikeda |
| 8,360,970 B2 | 1/2013 | Mangiardi |
| 8,372,131 B2 | 2/2013 | Hestad et al. |
| 8,382,048 B2 | 2/2013 | Nesper et al. |
| 8,397,335 B2 | 3/2013 | Gordin et al. |
| 8,419,625 B2 | 4/2013 | Ito |
| 8,435,174 B2 | 5/2013 | Cropper et al. |
| 8,460,180 B1 | 6/2013 | Zarate et al. |
| 8,460,186 B2 | 6/2013 | Ortiz et al. |
| 8,460,310 B2 | 6/2013 | Stern |
| 8,518,087 B2 | 8/2013 | Lopez et al. |
| 8,535,220 B2 | 9/2013 | Mondschein |
| 8,556,809 B2 | 10/2013 | Vijayanagar |
| 8,585,726 B2 | 11/2013 | Yoon et al. |
| 8,602,979 B2 | 12/2013 | Kitano |
| 8,622,894 B2 | 1/2014 | Banik et al. |
| 8,636,655 B1 | 1/2014 | Childs |
| 8,648,932 B2 | 2/2014 | Talbert et al. |
| 8,688,186 B1 | 4/2014 | Mao et al. |
| 8,690,764 B2 | 4/2014 | Clark et al. |
| 8,721,536 B2 | 5/2014 | Marino et al. |
| 8,740,779 B2 | 6/2014 | Yoshida |
| 8,784,421 B2 | 7/2014 | Carrison et al. |
| 8,821,378 B2 | 9/2014 | Morgenstern Lopez et al. |
| 8,834,507 B2 | 9/2014 | Mire et al. |
| 8,845,734 B2 | 9/2014 | Weiman |
| 8,852,242 B2 | 10/2014 | Morgenstern Lopez et al. |
| 8,870,753 B2 | 10/2014 | Boulais et al. |
| 8,870,756 B2 | 10/2014 | Maurice |
| 8,876,712 B2 | 11/2014 | Yee et al. |
| 8,888,689 B2 | 11/2014 | Poll et al. |
| 8,888,813 B2 | 11/2014 | To |
| 8,894,573 B2 | 11/2014 | Loftus et al. |
| 8,894,653 B2 | 11/2014 | Solsberg et al. |
| 8,926,502 B2 | 1/2015 | Levy et al. |
| 8,932,207 B2 | 1/2015 | Greenburg et al. |
| 8,932,360 B2 | 1/2015 | Womble et al. |
| 8,936,545 B2 | 1/2015 | To |
| 8,936,605 B2 | 1/2015 | Greenberg |
| 8,952,312 B2 | 2/2015 | Blanquart et al. |
| 8,961,404 B2 | 2/2015 | Ito |
| 8,972,714 B2 | 3/2015 | Talbert et al. |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,036 B2 | 6/2015 | Poll et al. |
| 9,050,037 B2 | 6/2015 | Poll et al. |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,123,602 B2 | 9/2015 | Blanquart |
| 9,131,948 B2 | 9/2015 | Fang et al. |

(56) References Cited

U.S. PATENT DOCUMENTS

| | | |
|---|---|---|
| 9,144,374 B2 | 9/2015 | Maurice, Jr. |
| 9,153,609 B2 | 10/2015 | Blanquart |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,226,647 B2 | 1/2016 | Sugawara |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik |
| RE46,062 E | 7/2016 | James |
| 9,386,971 B1 | 7/2016 | Casey et al. |
| 9,387,313 B2 | 7/2016 | Culbert et al. |
| 9,414,828 B2 | 8/2016 | Abidin et al. |
| 9,462,234 B2 | 10/2016 | Blanquart et al. |
| 9,486,296 B2 | 11/2016 | Mire et al. |
| 9,492,194 B2 | 11/2016 | Morgenstern Lopez et al. |
| 9,509,917 B2 | 11/2016 | Blanquart et al. |
| 9,510,853 B2 | 12/2016 | Aljuri et al. |
| 9,516,239 B2 | 12/2016 | Blanquart et al. |
| 9,522,017 B2 | 12/2016 | Poll et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,622,650 B2 | 4/2017 | Blanquart |
| 9,629,521 B2 | 4/2017 | Ratnakar |
| 9,641,815 B2 | 5/2017 | Richardson et al. |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 10,111,712 B2 | 10/2018 | Chegini et al. |
| 10,561,427 B2 | 2/2020 | Weitzman et al. |
| 10,576,231 B2 | 3/2020 | Gunday et al. |
| 10,682,130 B2 | 6/2020 | White et al. |
| 10,758,220 B2 | 9/2020 | White et al. |
| 10,869,659 B2 | 12/2020 | Thommen et al. |
| 10,874,425 B2 | 12/2020 | Thommen et al. |
| 10,987,129 B2 | 4/2021 | Thommen et al. |
| 11,000,312 B2 | 5/2021 | Thommen et al. |
| 11,331,090 B2 | 5/2022 | Thommen et al. |
| 11,439,380 B2 | 9/2022 | Thommen et al. |
| 11,559,328 B2 | 1/2023 | Richter et al. |
| 11,672,562 B2 | 6/2023 | Thommen et al. |
| 11,712,264 B2 | 8/2023 | Thommen et al. |
| 11,744,447 B2 | 9/2023 | Thommen et al. |
| 11,793,546 B2 | 10/2023 | Thommen et al. |
| 2002/0022762 A1 | 2/2002 | Beane et al. |
| 2002/0035313 A1 | 3/2002 | Scirica et al. |
| 2002/0091390 A1 | 7/2002 | Michelson |
| 2002/0138020 A1 | 9/2002 | Pflueger |
| 2002/0165560 A1 | 11/2002 | Danitz et al. |
| 2003/0083555 A1 | 5/2003 | Hunt et al. |
| 2003/0083688 A1 | 5/2003 | Simonson |
| 2003/0171744 A1 | 9/2003 | Leung et al. |
| 2003/0191474 A1 | 10/2003 | Cragg et al. |
| 2004/0092940 A1 | 5/2004 | Zwirnmann |
| 2004/0122446 A1 | 6/2004 | Solar |
| 2004/0127992 A1 | 7/2004 | Serhan et al. |
| 2004/0143165 A1 | 7/2004 | Alleyne |
| 2004/0158260 A1 | 8/2004 | Blau et al. |
| 2004/0158286 A1 | 8/2004 | Roux et al. |
| 2004/0249246 A1 | 12/2004 | Campos |
| 2005/0021040 A1 | 1/2005 | Bertagnoli |
| 2005/0075540 A1 | 4/2005 | Shluzas et al. |
| 2005/0075644 A1 | 4/2005 | DiPoto et al. |
| 2005/0080435 A1 | 4/2005 | Smith et al. |
| 2005/0085692 A1 | 4/2005 | Kiehn et al. |
| 2005/0090848 A1 | 4/2005 | Adams |
| 2005/0107671 A1 | 5/2005 | McKinley |
| 2005/0137461 A1 | 6/2005 | Marchek et al. |
| 2005/0187570 A1 | 8/2005 | Nguyen et al. |
| 2005/0192589 A1 | 9/2005 | Raymond et al. |
| 2005/0256525 A1 | 11/2005 | Culbert et al. |
| 2006/0020165 A1 | 1/2006 | Adams |
| 2006/0041270 A1 | 2/2006 | Lenker et al. |
| 2006/0052671 A1 | 3/2006 | McCarthy |
| 2006/0074445 A1 | 4/2006 | Gerber et al. |
| 2006/0142643 A1 | 6/2006 | Parker |
| 2006/0161189 A1 | 7/2006 | Harp |
| 2006/0173521 A1 | 8/2006 | Pond, Jr. et al. |
| 2006/0200186 A1 | 9/2006 | Marchek et al. |
| 2006/0206118 A1 | 9/2006 | Kim et al. |
| 2006/0264895 A1 | 11/2006 | Flanders |
| 2007/0049794 A1 | 3/2007 | Glassenberg et al. |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0162223 A1 | 7/2007 | Clark |
| 2007/0203396 A1 | 8/2007 | McCutcheon et al. |
| 2007/0213716 A1 | 9/2007 | Lenke et al. |
| 2007/0225556 A1 | 9/2007 | Ortiz et al. |
| 2007/0249899 A1 | 10/2007 | Seifert |
| 2007/0255100 A1 | 11/2007 | Barlow et al. |
| 2007/0260113 A1 | 11/2007 | Otawara |
| 2007/0260120 A1 | 11/2007 | Otawara |
| 2007/0260184 A1 | 11/2007 | Justis et al. |
| 2007/0270866 A1 | 11/2007 | von Jako |
| 2008/0015621 A1 | 1/2008 | Emanuel |
| 2008/0033251 A1 | 2/2008 | Araghi |
| 2008/0064921 A1 | 3/2008 | Larkin et al. |
| 2008/0064928 A1 | 3/2008 | Otawara |
| 2008/0081951 A1 | 4/2008 | Frasier et al. |
| 2008/0139879 A1 | 6/2008 | Olson et al. |
| 2008/0147109 A1 | 6/2008 | Kambin et al. |
| 2008/0183189 A1 | 7/2008 | Teichman et al. |
| 2008/0188714 A1 | 8/2008 | McCaffrey |
| 2008/0242930 A1 | 10/2008 | Hanypsiak et al. |
| 2008/0260342 A1 | 10/2008 | Kuroiwa |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0125032 A1 | 5/2009 | Gutierrez et al. |
| 2009/0149857 A1 | 6/2009 | Culbert et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0247831 A1* | 10/2009 | Miyamoto ......... A61B 1/00091 600/157 |
| 2009/0253965 A1 | 10/2009 | Miyamoto |
| 2009/0259184 A1 | 10/2009 | Okoniewski |
| 2009/0264895 A1 | 10/2009 | Gasperut et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0036384 A1 | 2/2010 | Gorek et al. |
| 2010/0076476 A1 | 3/2010 | To et al. |
| 2010/0081875 A1 | 4/2010 | Fowler et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0268241 A1 | 10/2010 | Flom et al. |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2010/0312103 A1 | 12/2010 | Gorek et al. |
| 2010/0317928 A1 | 12/2010 | Subramaniam |
| 2010/0324506 A1 | 12/2010 | Pellegrino et al. |
| 2011/0009905 A1 | 1/2011 | Shluzas |
| 2011/0028791 A1 | 2/2011 | Marino et al. |
| 2011/0040333 A1 | 2/2011 | Simonson et al. |

(56) References Cited

U.S. PATENT DOCUMENTS

| | | |
|---|---|---|
| 2011/0054507 A1 | 3/2011 | Batten et al. |
| 2011/0056500 A1 | 3/2011 | Shin et al. |
| 2011/0073594 A1 | 3/2011 | Bonn |
| 2011/0098628 A1 | 4/2011 | Yeung et al. |
| 2011/0106261 A1 | 5/2011 | Chin et al. |
| 2011/0112588 A1 | 5/2011 | Linderman et al. |
| 2011/0125158 A1 | 5/2011 | Diwan et al. |
| 2011/0130634 A1 | 6/2011 | Solitario, Jr. et al. |
| 2011/0201888 A1 | 8/2011 | Verner |
| 2011/0230965 A1 | 9/2011 | Schell et al. |
| 2011/0251597 A1 | 10/2011 | Bharadwaj et al. |
| 2011/0257478 A1 | 10/2011 | Kleiner et al. |
| 2011/0295070 A1 | 12/2011 | Yasunaga |
| 2011/0319941 A1 | 12/2011 | Bar et al. |
| 2012/0016192 A1 | 1/2012 | Jansen et al. |
| 2012/0029412 A1 | 2/2012 | Yeung et al. |
| 2012/0095296 A1 | 4/2012 | Trieu et al. |
| 2012/0101338 A1 | 4/2012 | O'Prey et al. |
| 2012/0111682 A1 | 5/2012 | Andre |
| 2012/0116170 A1 | 5/2012 | Vayser et al. |
| 2012/0157788 A1 | 6/2012 | Serowski et al. |
| 2012/0172664 A1 | 7/2012 | Hayman et al. |
| 2012/0197320 A1 | 8/2012 | Bereczki |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0259173 A1 | 10/2012 | Waldron et al. |
| 2012/0265022 A1 | 10/2012 | Menn |
| 2012/0296171 A1 | 11/2012 | Lovell et al. |
| 2012/0298820 A1 | 11/2012 | Manolidis |
| 2012/0316400 A1 | 12/2012 | Vijayanagar |
| 2012/0323080 A1 | 12/2012 | DeRidder et al. |
| 2013/0030535 A1 | 1/2013 | Foley et al. |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172674 A1 | 7/2013 | Kennedy, II et al. |
| 2013/0172676 A1 | 7/2013 | Levy et al. |
| 2013/0211202 A1 | 8/2013 | Perez-Cruet et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2013/0304106 A1 | 11/2013 | Breznock |
| 2014/0025121 A1 | 1/2014 | Foley et al. |
| 2014/0066940 A1 | 3/2014 | Fang et al. |
| 2014/0074170 A1 | 3/2014 | Mertens et al. |
| 2014/0088367 A1 | 3/2014 | DiMauro et al. |
| 2014/0128979 A1 | 5/2014 | Womble et al. |
| 2014/0142584 A1 | 5/2014 | Sweeney |
| 2014/0148647 A1 | 5/2014 | Okazaki |
| 2014/0163319 A1 | 6/2014 | Blanquart et al. |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0221749 A1 | 8/2014 | Grant et al. |
| 2014/0222092 A1 | 8/2014 | Anderson et al. |
| 2014/0257296 A1 | 9/2014 | Morgenstern Lopez |
| 2014/0257332 A1 | 9/2014 | Zastrozna |
| 2014/0257489 A1 | 9/2014 | Warren et al. |
| 2014/0261545 A1 | 9/2014 | Jenkins et al. |
| 2014/0275793 A1 | 9/2014 | Song |
| 2014/0275799 A1 | 9/2014 | Schuele |
| 2014/0276840 A1 | 9/2014 | Richter et al. |
| 2014/0276916 A1 | 9/2014 | Ahluwalia et al. |
| 2014/0277204 A1 | 9/2014 | Sandhu |
| 2014/0285644 A1 | 9/2014 | Richardson et al. |
| 2014/0318582 A1 | 10/2014 | Mowlai-Ashtiani |
| 2014/0336764 A1 | 11/2014 | Masson et al. |
| 2014/0357945 A1 | 12/2014 | Duckworth |
| 2014/0371763 A1 | 12/2014 | Poll et al. |
| 2014/0378985 A1 | 12/2014 | Mafi |
| 2015/0018623 A1 | 1/2015 | Friedrich et al. |
| 2015/0065795 A1 | 3/2015 | Titus |
| 2015/0073218 A1 | 3/2015 | Ito |
| 2015/0087913 A1 | 3/2015 | Dang et al. |
| 2015/0112398 A1 | 4/2015 | Morgenstern Lopez et al. |
| 2015/0133727 A1 | 5/2015 | Bacich et al. |
| 2015/0164496 A1 | 6/2015 | Karpowicz et al. |
| 2015/0216593 A1 | 8/2015 | Biyani |
| 2015/0223671 A1 | 8/2015 | Sung et al. |
| 2015/0223676 A1 | 8/2015 | Bayer et al. |
| 2015/0230697 A1 | 8/2015 | Phee et al. |
| 2015/0238073 A1 | 8/2015 | Charles et al. |
| 2015/0250377 A1 | 9/2015 | Iizuka |
| 2015/0257746 A1 | 9/2015 | Seifert |
| 2015/0272694 A1 | 10/2015 | Charles |
| 2015/0313585 A1 | 11/2015 | Abidin et al. |
| 2015/0313633 A1 | 11/2015 | Gross et al. |
| 2015/0327757 A1 | 11/2015 | Rozenfeld et al. |
| 2015/0335389 A1 | 11/2015 | Greenberg |
| 2015/0342619 A1 | 12/2015 | Weitzman |
| 2015/0342621 A1 | 12/2015 | Jackson, III |
| 2015/0366552 A1 | 12/2015 | Sasaki et al. |
| 2015/0374213 A1 | 12/2015 | Maurice, Jr. |
| 2015/0374354 A1 | 12/2015 | Boyd et al. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0192921 A1 | 7/2016 | Pimenta et al. |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0256036 A1 | 9/2016 | Gomez et al. |
| 2016/0287264 A1 | 10/2016 | Chegini et al. |
| 2016/0296220 A1 | 10/2016 | Mast et al. |
| 2016/0324541 A1 | 11/2016 | Pellegrino et al. |
| 2016/0345952 A1 | 12/2016 | Kucharzyk et al. |
| 2016/0353978 A1 | 12/2016 | Miller et al. |
| 2016/0367294 A1 | 12/2016 | Boyd et al. |
| 2017/0003493 A1 | 1/2017 | Zhao |
| 2017/0007226 A1 | 1/2017 | Fehling |
| 2017/0007294 A1 | 1/2017 | Iwasaka et al. |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086878 A1 | 3/2017 | Geist |
| 2017/0086939 A1 | 3/2017 | Vayser et al. |
| 2017/0105770 A1 | 4/2017 | Woolley et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2017/0245930 A1 | 8/2017 | Brannan et al. |
| 2017/0280969 A1 | 10/2017 | Levy et al. |
| 2017/0296038 A1 | 10/2017 | Gordon et al. |
| 2017/0311789 A1 | 11/2017 | Mulcahey et al. |
| 2018/0008138 A1 | 1/2018 | Thommen et al. |
| 2018/0008253 A1 | 1/2018 | Thommen et al. |
| 2018/0014858 A1 | 1/2018 | Biester et al. |
| 2018/0098788 A1 | 4/2018 | White et al. |
| 2018/0098789 A1 | 4/2018 | White et al. |
| 2018/0110503 A1 | 4/2018 | Flock et al. |
| 2018/0110506 A1 | 4/2018 | Thommen et al. |
| 2018/0153592 A1 | 6/2018 | Larson |
| 2018/0214016 A1 | 8/2018 | Thommen et al. |
| 2018/0249992 A1 | 9/2018 | Truckey |
| 2018/0333061 A1 | 11/2018 | Pracyk et al. |
| 2019/0105459 A1 | 4/2019 | Lajarín Barquero |
| 2019/0209154 A1 | 7/2019 | Richter et al. |
| 2019/0216454 A1 | 7/2019 | Thommen et al. |
| 2019/0216486 A1 | 7/2019 | Weitzman |
| 2019/0374236 A1 | 12/2019 | Weitzman et al. |
| 2020/0268368 A1 | 8/2020 | White et al. |

(56) References Cited

U.S. PATENT DOCUMENTS

| | | | |
|---|---|---|---|
| 2020/0360048 A1 | 11/2020 | White et al. |
| 2020/0367737 A1 | 11/2020 | Matsumoto et al. |
| 2021/0052298 A1 | 2/2021 | Thommen et al. |
| 2021/0186316 A1 | 6/2021 | Thommen et al. |
| 2021/0204973 A1 | 7/2021 | Thommen et al. |
| 2021/0282806 A1 | 9/2021 | Thommen et al. |
| 2022/0192700 A1 | 6/2022 | Thommen et al. |
| 2022/0265134 A1 | 8/2022 | Thommen et al. |

FOREIGN PATENT DOCUMENTS

| | | | |
|---|---|---|---|
| CN | 1742685 A | 3/2006 |
| CN | 101426437 A | 5/2009 |
| CN | 201290744 Y | 8/2009 |
| CN | 101815476 A | 8/2010 |
| CN | 102448380 A | 5/2012 |
| CN | 202211669 U | 5/2012 |
| CN | 102843984 A | 12/2012 |
| CN | 202740102 U | 2/2013 |
| CN | 102727309 B | 11/2014 |
| CN | 102497828 B | 9/2015 |
| CN | 102821673 B | 6/2016 |
| CN | 103976779 B | 9/2016 |
| CN | 106794032 A | 5/2017 |
| CN | 105286776 B | 11/2017 |
| CN | 107126254 B | 1/2020 |
| DE | 9415039 U1 | 11/1994 |
| DE | 29916026 U1 | 11/1999 |
| DE | 20309079 U1 | 8/2003 |
| EP | 0537116 A1 | 4/1993 |
| EP | 0890341 A1 | 1/1999 |
| EP | 0807415 B1 | 12/2003 |
| EP | 0891156 B1 | 7/2004 |
| EP | 2491848 B1 | 1/2014 |
| GB | 2481727 B | 5/2012 |
| JP | H05207962 A | 8/1993 |
| JP | H0681501 A | 3/1994 |
| JP | H08278456 A | 10/1996 |
| JP | 2000126190 A | 5/2000 |
| JP | 2000511788 A | 9/2000 |
| JP | 2001520906 A | 11/2001 |
| JP | 2002541901 A | 12/2002 |
| JP | 2007007438 A | 1/2007 |
| JP | 2008508943 A | 3/2008 |
| JP | 2009543612 A | 12/2009 |
| JP | 2011512943 A | 4/2011 |
| JP | 2012045325 A | 3/2012 |
| JP | 2012527327 A | 11/2012 |
| JP | 2012527930 A | 11/2012 |
| JP | 2013059688 A | 4/2013 |
| JP | 2013538624 A | 10/2013 |
| JP | 2014054561 A | 3/2014 |
| JP | 2014517710 A | 7/2014 |
| JP | 2015500680 A | 1/2015 |
| JP | 2015521913 A | 8/2015 |
| WO | 1996029014 A1 | 9/1996 |
| WO | 1997034536 A2 | 9/1997 |
| WO | 2001056490 A1 | 8/2001 |
| WO | 2001089371 A1 | 11/2001 |
| WO | 2002002016 A1 | 1/2002 |
| WO | 2004039235 A2 | 5/2004 |
| WO | 2004103430 A2 | 12/2004 |
| WO | 2006017507 A2 | 2/2006 |
| WO | 2007059068 A1 | 5/2007 |
| WO | 2008121162 A1 | 10/2008 |
| WO | 2009033207 A1 | 3/2009 |
| WO | 2009108318 A2 | 9/2009 |
| WO | 2010111629 A2 | 9/2010 |
| WO | 2010135537 A2 | 11/2010 |
| WO | 2010138083 A1 | 12/2010 |
| WO | 2012004766 A2 | 1/2012 |
| WO | 2012040239 A1 | 3/2012 |
| WO | 2012122294 A1 | 9/2012 |
| WO | 2013033426 A2 | 3/2013 |
| WO | 2013059640 A1 | 4/2013 |
| WO | 2013074396 A1 | 5/2013 |
| WO | 2014041540 A1 | 3/2014 |
| WO | 2014050236 A1 | 4/2014 |
| WO | 2014100761 A2 | 6/2014 |
| WO | 2014185334 A1 | 11/2014 |
| WO | 2014188796 A1 | 11/2014 |
| WO | 2015026793 A1 | 2/2015 |
| WO | 2015175635 A1 | 11/2015 |
| WO | 2016111373 A1 | 7/2016 |
| WO | 2016131077 A1 | 8/2016 |
| WO | 2016168673 A1 | 10/2016 |
| WO | 2016201292 A1 | 12/2016 |
| WO | 2017006684 A1 | 1/2017 |
| WO | 2017015480 A1 | 1/2017 |
| WO | 2017040873 A1 | 3/2017 |
| WO | 2017083648 A1 | 5/2017 |
| WO | 2018131039 A1 | 7/2018 |
| WO | 2018147225 A1 | 8/2018 |
| WO | 2018165365 A2 | 9/2018 |
| WO | 2021209987 A1 | 10/2021 |

OTHER PUBLICATIONS

U.S. Appl. No. 18/479,059, filed Sep. 30, 2023, Devices and Methods for Providing Surgical Access.
U.S. Appl. No. 15/254,877, filed Sep. 1, 2016, Multi-Shield Spinal Access System.
U.S. Appl. No. 15/437,792, filed Feb. 21, 2017, Multi-Shield Spinal Access System.
U.S. Appl. No. 15/692,845, filed Aug. 31, 2017, Surgical Visualization Systems and Related Methods.
U.S. Appl. No. 15/697,494, filed Sep. 7, 2017, Multi-Shield Spinal Access System.
U.S. Appl. No. 15/786,846, filed Oct. 18, 2017, Devices and Methods for Surgical Retraction.
U.S. Appl. No. 15/786,858, filed Oct. 18, 2017, Devices and Methods for Providing Surgical Access.
U.S. Appl. No. 15/786,891, filed Oct. 18, 2017, Surgical Access Port Stabilization.
U.S. Appl. No. 15/786,923, filed Oct. 18, 2017, Surgical Instrument Connectors and Related Methods.
U.S. Appl. No. 15/901,435, filed Feb. 21, 2018, Surgical Visualization Systems and Related Methods.
U.S. Appl. No. 15/931,839, filed May 14, 2020, Surgical Access Port Stabilization.
U.S. Appl. No. 15/966,293, filed Apr. 30, 2018, Neural Monitoring Devices and Methods.
U.S. Appl. No. 16/352,654, filed Mar. 13, 2019, Multi-Shield Spinal Access System.
U.S. Appl. No. 16/362,497, filed Mar. 22, 2019, Surgical Instrument Connectors and Related Methods.
U.S. Appl. No. 16/985,200, filed Aug. 4, 2020, Devices and Methods for Providing Surgical Access.
U.S. Appl. No. 17/089,695, filed Nov. 4, 2020, Multi-Shield Spinal Access System.
U.S. Appl. No. 17/159,129, filed Jan. 26, 2021, Multi-Shield Spinal Access System.
U.S. Appl. No. 17/192,889, filed Mar. 5, 2021, Surgical Visualization Systems and Related Methods.
U.S. Appl. No. 17/214,759, filed Mar. 26, 2021, Multi-Shield Spinal Access System.
U.S. Appl. No. 17/692,942, filed Mar. 11, 2022, Multi-Shield Spinal Access System.
U.S. Appl. No. 17/740,305, filed May 9, 2022, Surgical Visualization Systems and Related Methods.
U.S. Appl. No. 18/091,255, filed Dec. 29, 2022, Multi-Shield Spinal Access System.
Australian Examination Report for Application No. 2018225113, dated Jul. 15, 2022 (4 pages).
Chinese Office Action for Application No. 201880013056.7, dated Mar. 25, 2021 (15 pages).
Chinese Office Action for Application No. 201880013056.7, dated Oct. 26, 2021 (6 Pages).

(56) References Cited

OTHER PUBLICATIONS

Chinese Office Action for Application No. 201880016688.9, dated Mar. 8, 2022, with Translation (21 pages).
Chinese Decision of Reexamination issued for 201680051245.4, dated Aug. 23, 2022, (23 pages).
Chinese Office Action and Search Report issued for Application No. 201880058099, dated Nov. 2, 2022 (14 pages).
Clinical Workbook of Neurosurgery in Xijing [M], edited by Fei Zhou, Xi'an: Fourth Military Medical University Press, Aug. 2012, pp. 431-432: an endoscope with a diameter of 3.7 mm is used for intramedullary examination).
Extended European Search Report for Application No. 16843037.9; dated Mar. 14, 2019 (8 pages).
Extended European Search Report for Application No. 18758290.3, dated Nov. 27, 2020 (7 pages).
Extended European Search Report for Application No. 20212396.4, dated Sep. 23, 2021 (9 pages).
Extended European Search Report for Application No. 18854503.2, dated Apr. 15, 2021 (10 pages).
Extended European Search Report for Application No. 19758283.6, dated Sep. 28, 2021 (8 pages).
Extended European Search Report for Application No. 18764249.1, dated Mar. 11, 2022 (8 pages).
Extended European Search Report for Application No. 18764504.9, dated Mar. 18, 2022 (7 pages).
Extended European Search Report for Application No. 18764370.5, dated Mar. 25, 2022 (8 pages).
Hott, J. S., et al., "A new table-fixed retractor for anterior odontoid screw fixation: technical note," J Neurosurg (Spine) 3), 2003, v. 98, pp. 118-120.
International Search Report and Written Opinion for Application No. PCT/US2015/043554, dated Nov. 19, 2015 (8 pages).
International Search Report and Written Opinion for Application No. PCT/US2015/048485, dated Feb. 9, 2016. (16 pages).
International Search Report and Written Opinion for Application No. PCT/US2015/060978, dated Feb. 15, 2016 (8 pages).
Invitation to Pay Additional Fees for Application No. PCT/US2016/050022, dated Nov. 3, 2016 (2 pages).
International Search Report and Written Opinion for Application No. PCT/US2016/050022, dated Feb. 1, 2017 (19 pages).
International Preliminary Report on Patentability issued for Application No. PCT/US2016/050022, dated Mar. 15, 2018.
International Search Report and Written Opinion for Application No. PCT/US2018/018905, dated May 7, 2018 (10 pages).
International Search Report for Application No. PCT/IB2018/057367, dated Jan. 29, 2019, (4 pages).
International Search Report and Written Opinion for Application No. PCT/US2018/021449, dated Aug. 27, 2018 (13 pages).
International Search Report and Written Opinion for Application No. PCT/US2018/021454, dated Jul. 3, 2018 (16 pages).
International Search Report and Written Opinion for Application No. PCT/US2018/021466 dated Jul. 3, 2018 (8 pages).
International Search Report and Written Opinion for Application No. PCT/US2018/047136, dated Jan. 23, 2019 (9 pages).
International Search Report and Written Opinion for Application No. PCT/EP2020/056706, dated Jun. 9, 2020 (17 pages).
International Search Report and Written Opinion issued for Application No. PCT/US2018/021472, dated Jul. 19, 2018.
International Search Report and Written Opinion for Application No. PCT/US19/18700, dated May 3, 2019 (7 pages).
Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Japanese Office Action issued in Appln. No. JP 2018-511695, dated May 26, 2020 (21 pages).
Japanese Office Action for Application No. JP 2019-548591, dated Oct. 5, 2021, (14 pages).
Japanese Office Action for Application No. JP 2019-545263, dated Jan. 4, 2022 (11 pages).
Japanese Office Action for Application No. JP 2019-545263, dated Aug. 9, 2022 (8 pages).
Japanese Office Action for Application No. JP 2020-513791, dated May 17, 2022 (8 pages).
Japanese Office Action for Application No. JP 2020-177880, dated May 31, 2022 (3 pages).
Japanese Decision to Grant a Patent for Application No. JP 2020-177880, dated Dec. 6, 2022 (2 pages).
Japanese Decision to Grant Patent for Application No. JP 2020-544278, dated Mar. 14, 2023.
Jung, K., et al., "A hands-free region-of-interest selection interface for solo surgery with a wide-angle endoscope: preclinical proof of concept," Surg Endosc, 2017, v. 31, pp. 974-980.
Regan, J. M. et al., "Burr Hole Washout versus Craniotomy for Chronic Subdural Hematoma: Patient Outcome and Cost Analysis," Plos One, Jan. 22, 2015, DOI:10.1371/journal.pone.0115085.
Shalayev, S. G. et al, "Retrospective analysis and modifications of retractor systems for anterior odontoid screw fixation," Neurosurg Focus 16 (1):Article 14, 2004, pp. 1-4.

\* cited by examiner

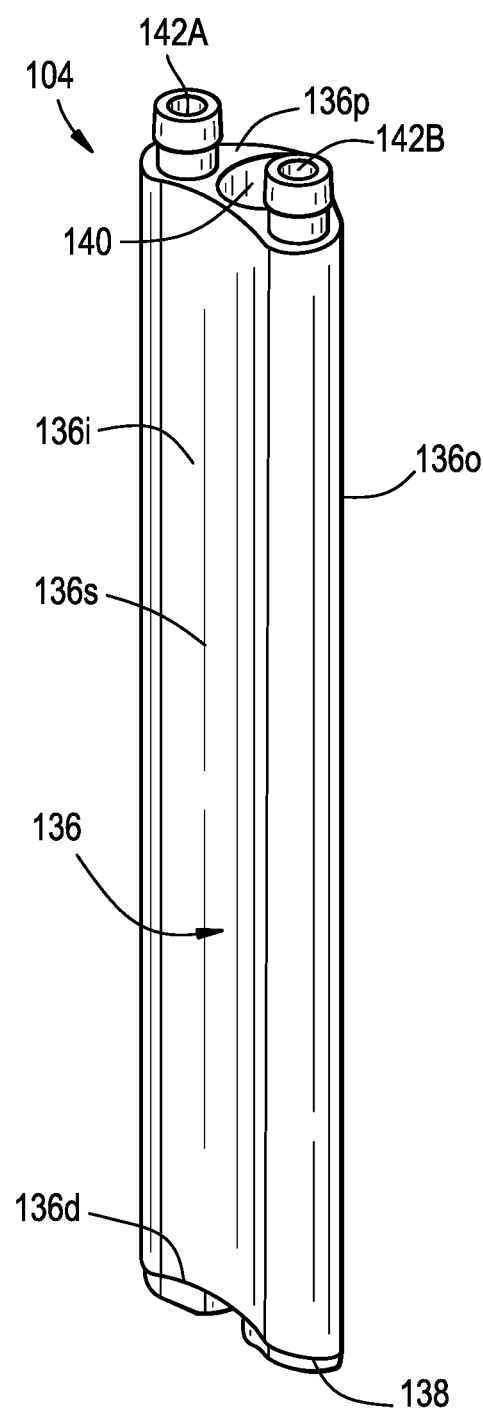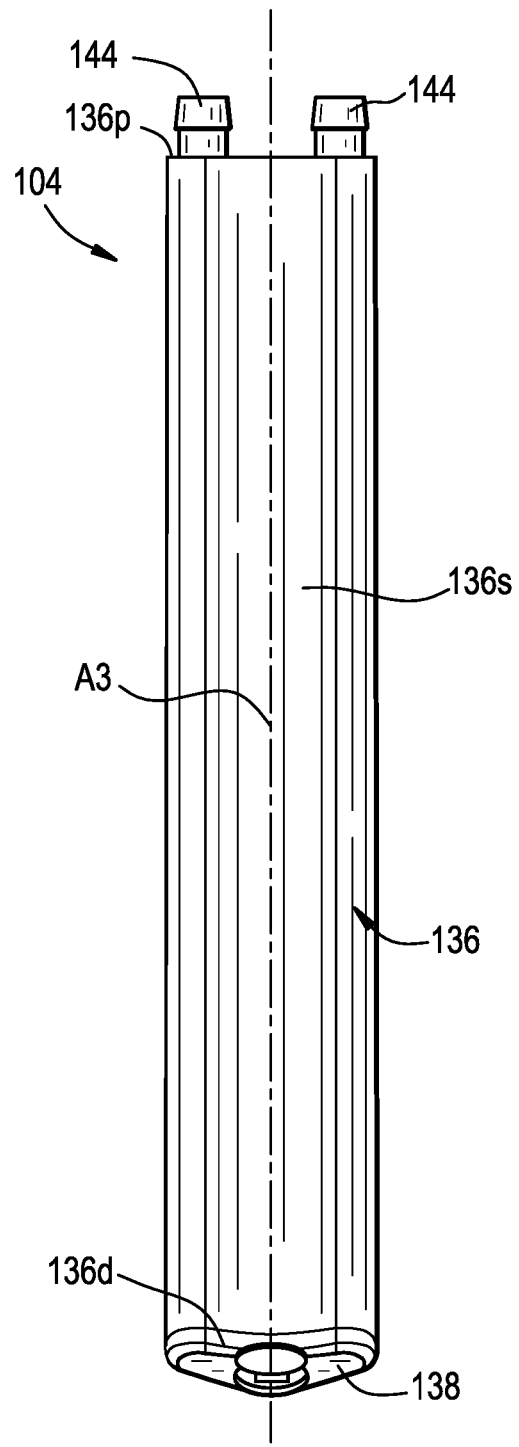

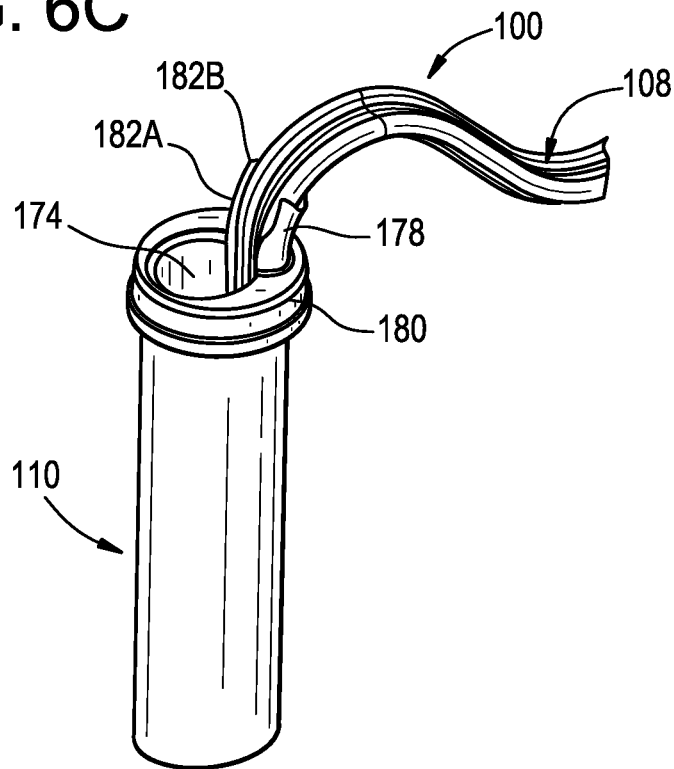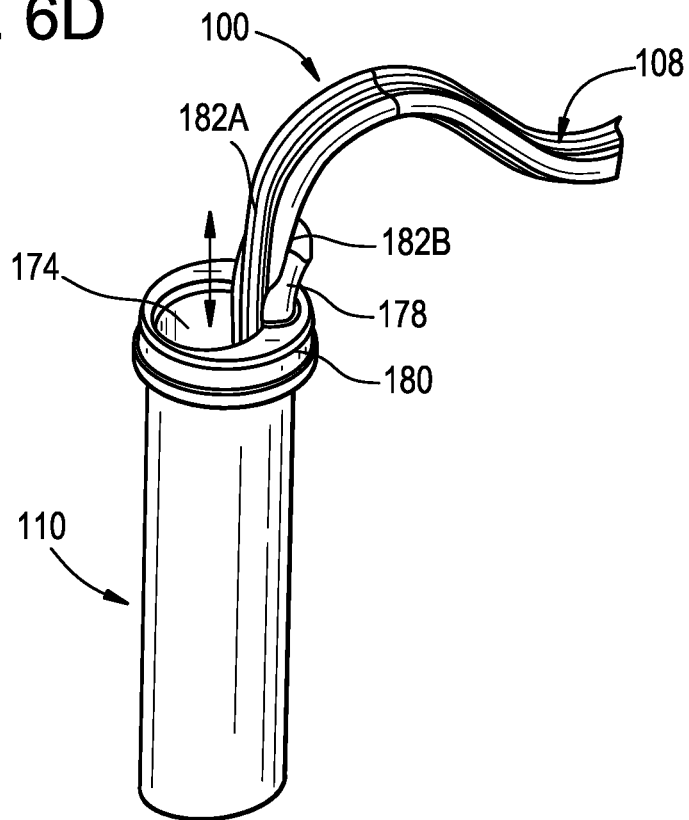

SURGICAL VISUALIZATION SYSTEMS AND RELATED METHODS

CROSS-REFERENCE TO RELATED APPLICATIONS

The present application claims priority to, and is a continuation of, U.S. application Ser. No. 15/692,845, filed on Aug. 31, 2017. U.S. application Ser. No. 15/692,845 claims priority to U.S. Provisional Application No. 62/468,475, filed on Mar. 8, 2017. U.S. application Ser. No. 15/692,845 is also a continuation-in-part of U.S. application Ser. No. 15/437,792 filed on Feb. 21, 2017, now issued as U.S. Pat. No. 10,874,425. U.S. application Ser. No. 15/437,792 is a continuation-in-part of U.S. application Ser. No. 15/254,877, filed on Sep. 1, 2016, now issued as U.S. Pat. No. 10,987,129. U.S. application Ser. No. 15/254,877 claims priority to U.S. Provisional Application No. 62/214,297 filed on Sep. 4, 2015. Each of these applications is hereby incorporated by reference in its entirety.

FIELD

Surgical visualization systems and related methods are disclosed herein, e.g., for providing visualization during surgical procedures, including minimally-invasive spinal procedures.

BACKGROUND

There are many instances in which it may be desirable to provide a surgeon or other user with visualization of a surgical site. While a number of surgical visualization systems have been developed, they are often heavy and cumbersome to use, difficult to clean or sterilize, or have properties that render them inadequate or impossible to use for many types of procedures. A spinal endoscope, for example, is typically used only in limited procedures, such as herniated disc repair and other pathologies that are reduced to a predictable, very small location. Such devices typically require very small, specialized tools with low output force and tissue processing capabilities. Such devices can require multiple human operators, with an assistant or other user holding and operating the visualization system while the surgeon uses both hands to perform the surgery. In addition, such devices can have a steep learning curve, as the visualization orientation may be dictated by instrument orientation, and therefore may be constantly changing over the course of the procedure.

SUMMARY

Surgical visualization systems and related methods are disclosed herein, e.g., for providing visualization during surgical procedures. Systems and methods herein can be used in a wide range of surgical procedures, including spinal surgeries such as minimally-invasive fusion or discectomy procedures. Systems and methods herein can include various features for enhancing end user experience, improving clinical outcomes, or reducing the invasiveness of a surgery. Exemplary features can include access port integration, hands-free operation, active and/or passive lens cleaning, adjustable camera depth, and many others.

In some embodiments, a surgical system can include an access device having a working channel and a visualization channel; and a visualization system at least partially disposed in the visualization channel, the visualization system comprising a camera module and a housing in which the camera module is mounted.

The camera module can include an image sensor and a lens configured to direct reflected light onto the image sensor, the image sensor and the lens being disposed within the housing. The camera module can include an optical fiber having a distal end disposed within the housing and a proximal end in optical communication with a light source. The lens can be disposed within a lens lumen of a lens barrel and the optical fiber can be disposed in an illumination lumen of the lens barrel. The illumination lumen can be disposed closer to the center of the access device working channel than the lens lumen. The lens barrel can include a distal-facing surface that is obliquely angled relative to a central longitudinal axis of the working channel. The system can include a diffuser mounted in a recess formed in the distal-facing surface of the lens barrel over the optical fiber. The recess can be crescent-shaped and can substantially follow the perimeter of the lens lumen. A central region of the lens can be coated with hydrophobic coating and a peripheral region of the lens can be coated with a hydrophilic coating.

The housing can include a main body and a distal end cap. The main body can include a camera lumen in which the camera module is disposed and first and second fluid lumens. The camera lumen can be disposed centrally in the main body, between the first and second fluid lumens. A distal facing surface of the main body and a distal facing surface of the end cap can be obliquely angled relative to a central longitudinal axis of the working channel. The main body can have a sidewall having a concave inner surface disposed adjacent the working channel and a convex outer surface disposed opposite the inner surface. The inner surface of the sidewall of the main body can define at least a portion of an inner surface of the working channel. The outer surface of the sidewall can include first and second planar regions connected by a central transition region that defines a section of a cylinder, the transition region following an outer perimeter of a camera lumen of the main body. The inner surface can be concavely curved and connected to the outer surface by first and second transition regions that define sections of respective cylinders, the first and second transition regions following the outer perimeters of first and second fluid lumens formed in the main body. The housing can be formed from an inner circular tube disposed within and attached to an outer oval tube to define a camera lumen and first and second fluid lumens. The housing can be formed from an inner circular tube having opposed first and second outer shells attached thereto to define a camera lumen and first and second fluid lumens. The end cap can include a cut-out axially aligned with a lens of the camera module and a cut-out axially aligned with an illumination system of the camera module. A proximal-facing surface of the end cap can define a recess configured to direct fluid flowing out of a first fluid lumen of the housing across a lens of the camera module and into a second fluid lumen of the housing. The recess can include lateral end portions axially aligned with the first and second fluid lumens and medial endportions that are open to a cut-out of the end cap.

The system can include a connector assembly extending from the housing, the connector assembly including electrical and optical connections to the camera module and fluid connections to the housing. The connector assembly can have an exterior shape that matches that of the housing. The system can include a controller having an electronic display configured to display image data captured by an image sensor of the camera module. The visualization channel can intersect or overlap with the working channel. The housing and the camera module can be axially-translatable relative to the access device. The visualization channel can have a central longitudinal axis disposed radially outward from a central longitudinal axis of the working channel.

The access device can include a mating feature configured to selectively hold the visualization system in a desired position relative to the access device. The mating feature can include a locking track configured to receive a portion of the visualization system to restrict movement of the visualization system relative to the access device. The locking track can be formed in a proximal extension of the access device. The locking track can receive the visualization system in a snap-fit or friction fit. The mating feature can include an adjustment track configured to receive at least a portion of the visualization system to allow movement of the visualization system relative to the access device. The visualization system can be configured such that the visualization system can be loaded into the locking track by moving it radially outward from a central longitudinal axis of the visualization channel. The locking track can be curved or obliquely angled away from a central longitudinal axis of the visualization channel. The visualization system can be configured such that the visualization system can be secured to the mating feature at any point along a connector assembly of the visualization system. The mating feature can include a wheel that, when rotated, advances or retracts the visualization system relative to the access device. The mating feature can include a coil spring clamp configured to selectively lock the visualization system in a fixed position relative to the access device. The mating feature can include an O-ring disposed around a portion of the visualization system and a cone movably coupled to the access device, the cone being movable between a first position in which it expands the O-ring to allow movement of the visualization system relative to the access device and a second position in which the O-ring is released to clamp onto the visualization system and prevent movement of the visualization system relative to the access device.

The system can include a sleeve insertable through the working channel of the access device, the sleeve having an outside diameter and a bulb movably coupled to the sleeve, the bulb being movable between a first position in which the bulb is disposed entirely within the outside diameter of the sleeve and a second position in which at least a portion of the bulb protrudes out from the outside diameter of the sleeve. The bulb in the second position can be configured to fill a void space within the access device distal to the visualization channel of the access device. The bulb can include a distal-facing surface that is curved or ramped to form a gradual transition between a cylindrical dilator inserted through the sleeve and an outer surface of the access device. The bulb can be movable between the first and second positions by translating the sleeve axially relative to the access device. The bulb can be movable between the first and second positions by rotating the sleeve relative to the access device. The bulb can be biased towards the second position. The access device can include a transition portion at a distal end thereof, the transition portion being movable between a first position in which the transition portion extends radially-inward to provide a gradual transition between a cylindrical dilator inserted through the working channel and an outer surface of the access device and a second position in which the transition portion is moved radially-outward from the first position. The system can include a dilation shaft insertable through the access device to move the transition portion to the second position. The transition portion can include a plurality of flexible and resilient fingers.

In some embodiments, a visualization system can include a camera module having an image sensor and a lens; and a housing in which the camera module is disposed, the housing having a main body, first and second fluid channels, and an end cap configured to direct fluid flow through the channels across the lens of the camera module.

The camera module can include an optical fiber having a distal end disposed within the housing and a proximal end in optical communication with a light source. The lens can be disposed within a lens lumen of a lens barrel and the optical fiber can be disposed in an illumination lumen of the lens barrel. The system can include a diffuser mounted in a recess formed in a distal-facing surface of the lens barrel over the optical fiber. The recess can be crescent-shaped and can substantially follow the perimeter of the lens lumen. A central region of the lens can be coated with a hydrophobic coating and a peripheral region of the lens can be coated with a hydrophilic coating.

The camera module can be disposed centrally in the main body, between the first and second fluid channels. A distal facing surface of the main body and a distal facing surface of the end cap can be obliquely angled relative to a central longitudinal axis of the camera module. The main body can have an outer surface that includes first and second planar regions connected by a central transition region that defines a section of a cylinder, the transition region following an outer perimeter of a camera lumen of the main body. The main body can have an inner surface that is concavely curved and connected to the outer surface by first and second transition regions that define sections of respective cylinders, the first and second transition regions following the outer perimeters of the first and second fluid channels. The housing can be formed from an inner circular tube disposed within and attached to an outer oval tube to define a camera lumen and the first and second fluid channels. The housing can be formed from an inner circular tube having opposed first and second outer shells attached thereto to define a camera lumen and the first and second fluid channels. The end cap can include a cut-out axially aligned with the lens. A proximal-facing surface of the end cap can define a recess configured to direct fluid flowing out of the first fluid channel of the housing across the lens and into the second fluid channel of the housing. The recess can include lateral end portions axially aligned with the first and second fluid channels and medial endportions that are open to the cut-out of the end cap.

The system can include a connector assembly extending from the housing, the connector assembly including electrical and optical connections to the camera module and fluid connections to the housing. The connector assembly can have an exterior shape that matches that of the housing. The system can include a controller having an electronic display configured to display image data captured by an image sensor of the camera module.

In some embodiments, a surgical method can include inserting an access device into a patient; mounting the access device to an anchor, the anchor comprising at least one of an anatomical structure of the patient and an implant implanted in the patient; inserting a camera module into the access device; adjusting a depth of the camera module relative to the access device; and securing the camera module to a mating feature of the access device to maintain the camera module at the adjusted depth.

The anchor can include a bone anchor implanted in a pedicle of the patient. The method can include performing a surgical procedure through the access device without using hands to hold the access device or the camera module. The method can include inserting a fusion cage through the access device and into an intervertebral disc space. Inserting the access device can include positioning a distal end of the access device in proximity to an intervertebral disc space of the patient via a TLIF approach. The method can include positioning the camera module in a relatively proximal position relative to the access device, performing a bone resection through the access device, positioning the camera module in a relatively distal position relative to the access device, and removing disc tissue through the access device. The method can include directing cleaning media through a housing in which the camera module is disposed and across a lens of the camera module. Inserting the access device can include positioning a distal end of the access device in a dry environment of the patient. Inserting the access device can include positioning a distal end of the access device in a sinus cavity of the patient. The method can include performing a laryngoscopy or a bronchoscopy using the camera module.

BRIEF DESCRIPTION OF THE DRAWINGS

FIG. 3C is a perspective view of the housing of FIG. 3A;

FIG. 3D is a side view of the housing of FIG. 3A;

FIG. 6C is a perspective view of the system and access device of FIG. 6A, with the system disposed in a locking track of the access device;

FIG. 6D is a perspective view of the system and access device of FIG. 6A, with the system disposed in an adjustment track of the access device;

DETAILED DESCRIPTION

Figure 1:
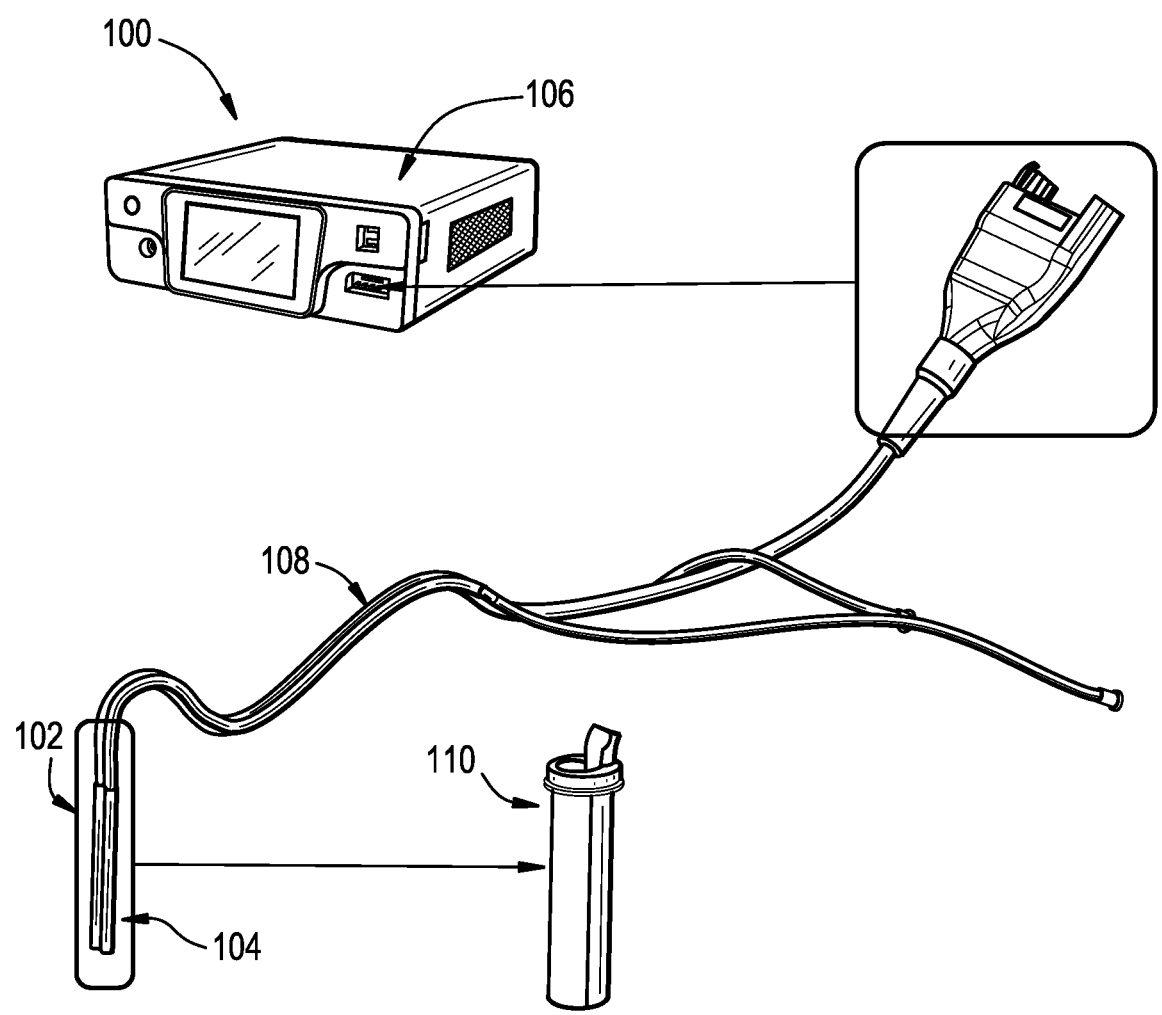
FIG. 1 is a perspective view of a surgical visualization system and an access device.

Surgical visualization systems and related methods are disclosed herein, e.g., for providing visualization during surgical procedures. Systems and methods herein can be used in a wide range of surgical procedures, including spinal surgeries such as minimally-invasive fusion or discectomy procedures. Systems and methods herein can include various features for enhancing end user experience, improving clinical outcomes, or reducing the invasiveness of a surgery. Exemplary features can include access port integration, hands-free operation, active and/or passive lens cleaning, adjustable camera depth, and many others.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

In some embodiments, the surgical visualization systems disclosed herein can enable hands free visualization. For example, a camera module can be mounted in an access device in a manner that eliminates the need for a surgeon, assistant, or other user to manually hold the camera in place. As another example, the access device can be secured to a support, e.g., an operating table, an anatomical anchor, or the like, eliminating the need for the user to manually hold the access port, or to hold a camera module disposed therein. Accordingly, the user's hands can be free to perform other steps of the surgery.

The camera module can be separate and independent from surgical instruments used to carry out the procedure. Accordingly, the instruments with which the visualization system can be used are not restricted, and the system can be used with any of a variety of custom or off-the-shelf instruments. Such instruments can include instruments with increased size, strength, output force, and/or tissue processing capabilities. In addition, the visual trajectory of the camera can be independent of instrument positioning. This can allow the camera, and/or an access device in which the camera is disposed, to remain relatively stationary as instruments are manipulated and as the procedure is carried out. The field of view of the camera can thus remain substantially fixed during the procedure, providing the user with good spatial orientation and providing a reduced learning curve as compared to other visualization systems.

Traditional spinal microscopes can protrude significantly from the patient, occupy a lot of space over a surgical incision, and a clear space must be maintained around the proximal end of the scope to allow a user to look through the scope. This can limit the degree to which other instruments can be manipulated during the surgery, for example limiting the possible access angles of the instruments. This can also restrict the size and types of instruments that can be used, the placement of the user's hands during various steps in the surgery, and so forth. Visualization systems of the type described herein can be integrated with an access device, can have a low-profile design, and/or can display captured images on an external monitor, reducing or eliminating these potential concerns.

In some embodiments, the surgical visualization systems disclosed herein can enable adjustment of the depth of a camera within an access device. In some embodiments, the camera depth can be quickly and easily adjusted. In some embodiments, the camera depth can be adjusted with one hand in a tool-free manner. The ability to easily adjust camera depth can allow visualization to be optimized for each stage of a surgical procedure in a seamless manner that does not interfere with or disrupt the surgical flow. In a spinal surgery, for example, the camera can be retracted proximally when performing gross bone removal and other steps that are relatively low risk, but could cause the camera lens to become obscured with debris. Later, when doing nerve work or other tasks that require greater precision, the camera can be advanced distally within the access device. In some cases, the camera can be advanced to protrude from the distal end of the access, e.g., to position the camera within an intervertebral disc space.

In some embodiments, the surgical visualization systems disclosed herein can provide improved visualization in harsh or challenging operating environments. In many spinal procedures, for example, the operating environment is dry (as compared to fluid filled cavities that exist in other surgeries where visualization systems are used) and a large amount of smoke and cutting debris can be generated during the surgery. The surgical visualization systems disclosed herein can include active and/or passive features for clearing such debris from the camera lens, or for preventing such debris from blocking or sticking to the lens in the first place. In some embodiments, the surgical visualization systems disclosed herein can provide high-resolution visualization in minimally-invasive spinal procedures, such as endoscopic transforaminal lumbar interbody fusion (TLIF) procedures.

In some embodiments, the surgical visualization systems disclosed herein can be a single-use disposable, can be easily cleanable or sterilizable, can have a low-profile, can be lightweight, can be low-cost, can have high resolution, and/or can be used in minimally-invasive surgery, e.g., spinal surgery.

FIG. 1 illustrates an exemplary surgical visualization system 100. The system 100 can include a camera module 102 disposed within a housing 104. The housing 104 can be configured for positioning at a surgical site or in proximity to a surgical site. The system 100 can include a controller or display 106 for controlling the camera module 102, for displaying images captured by the camera module, and so forth. The camera module 102 and/or the housing 104 can be coupled to the controller 106 by a connector or connector assembly 108. The connector assembly 108 can include electrical and/or optical connections to the camera module 102. The connector assembly 108 can include fluid connections to the housing 104. The fluid connections can be used to deliver material to the housing 104, to withdraw material from the housing, or to both deliver and withdraw material from the housing, e.g., for cleaning a lens of the camera module 102. The system 100 can be selectively mountable to an access device 110 or other support, can be used independently, can be selectively mountable to a surgical robot or connector arm, can be insertable through a surgical instrument, or can be used in various other ways to facilitate a surgical procedure.

Figure 2A:
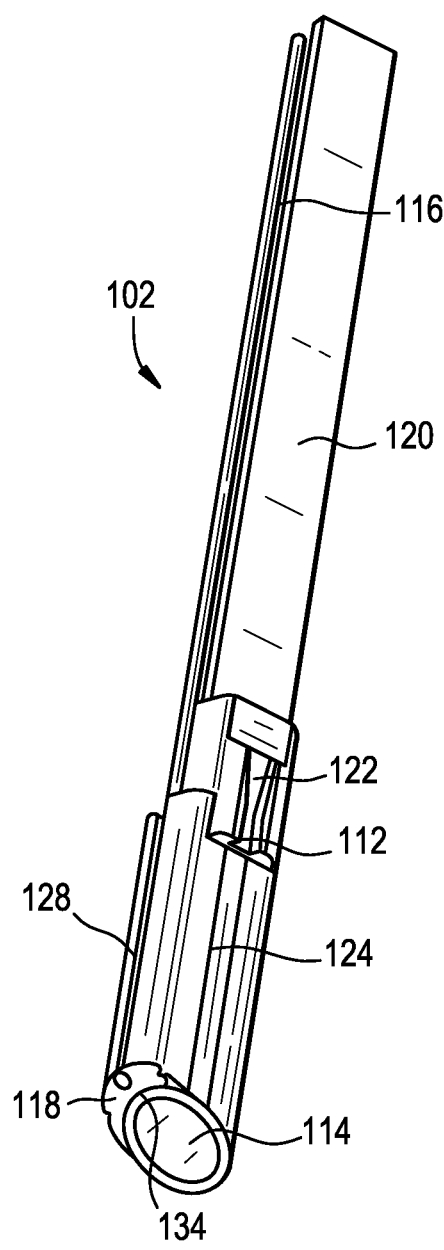
FIG. 2A is a perspective view of a camera module of the system of FIG. 1.
Figure 2B:
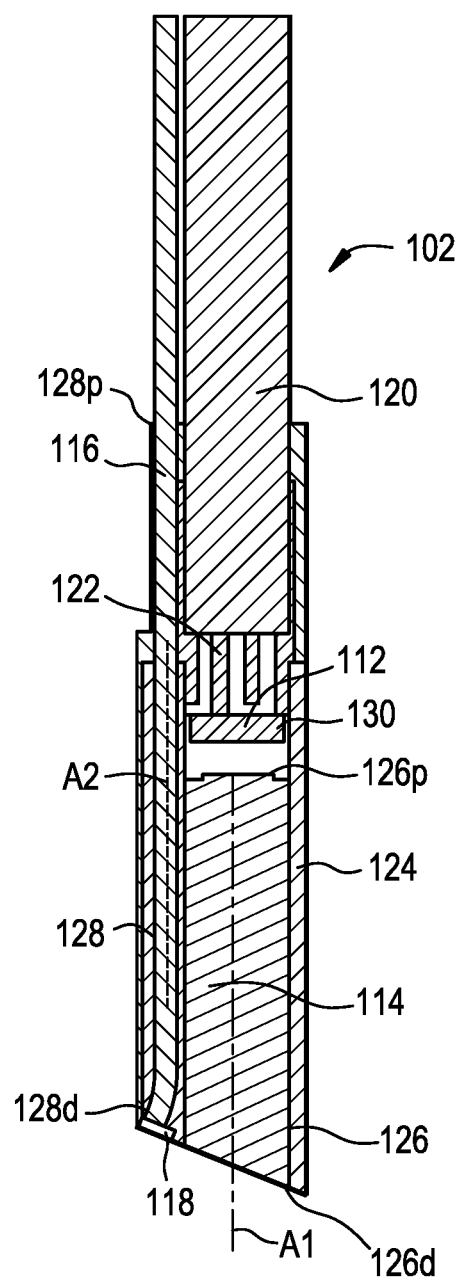
FIG. 2B is a sectional side view of the camera module of FIG. 2A.
Figure 2C:
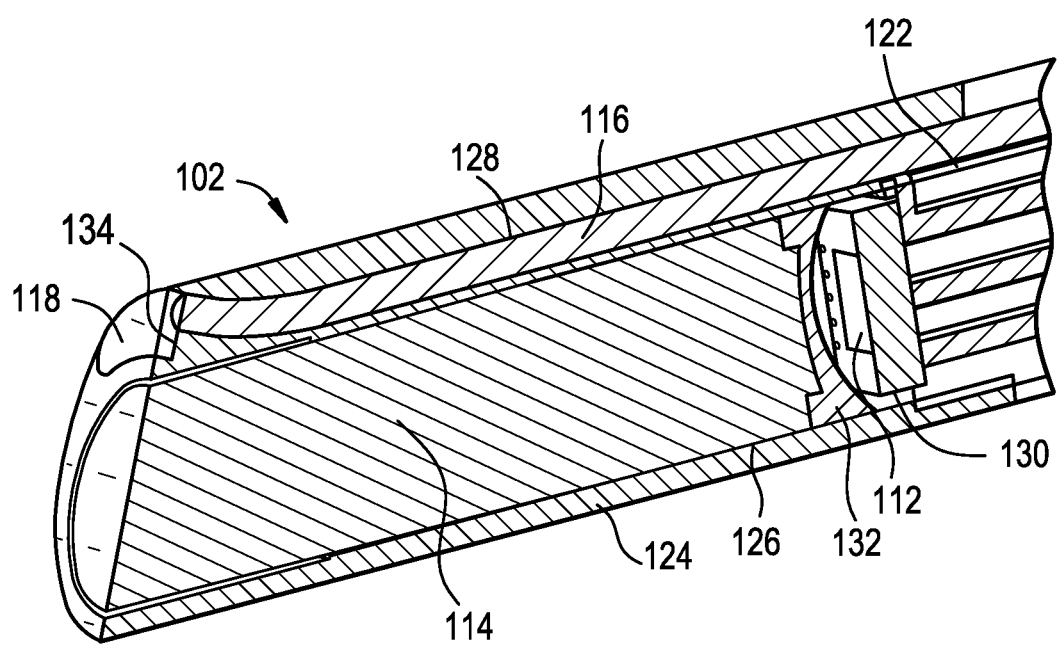
FIG. 2C is a sectional perspective view of the camera module of FIG. 2A.

The camera module 102 is shown in greater detail in FIGS. 2A-2C. The camera module 102 can include an image sensor 112 for capturing images of a field disposed in view of the image sensor, e.g., images of a surgical site. The image sensor 112 can be configured to convert light directed onto the image sensor into an electronic signal. The image sensor 112 can be configured to capture full color still and video images. The image sensor 112 can be configured to capture 1080p high definition video. The image sensor 112 can be a full-frame image sensor. The image sensor 112 can be a charge-coupled-device (CCD) image sensor, a complementary-metal-oxide-semiconductor (CMOS) image sensor, an N-type metal-oxide-semiconductor (NMOS) image sensor, a video chip, a chip-on-tip camera, and/or can use various other image sensing technologies. The image sensor 112 can be a monochromatic sensor having a pixel array and supporting circuitry that are sensitive to electromagnetic radiation of any wavelength. Exemplary image sensors 112, and other features that can be included or incorporated in the camera module 102, are disclosed in U.S. patent application Ser. No. 13/952,518 entitled CONTINUOUS VIDEO IN A LIGHT DEFICIENT ENVIRONMENT, issued as U.S. Pat. No. 10,568,496; U.S. patent application Ser. No. 14/214,412 entitled IMAGE ROTATION USING SOFTWARE FOR ENDOSCOPIC APPLICATIONS, issued as U.S. Pat. Nos. 10,362,240; 8,648,932 entitled SYSTEM, APPARATUS AND METHODS FOR PROVIDING A SINGLE USE IMAGING DEVICE FOR STERILE ENVIRONMENTS; U.S. Pat. No. 8,952,312 entitled IMAGE SENSOR FOR ENDOSCOPIC USE; U.S. Pat. No. 8,972,714 entitled SYSTEM AND METHOD FOR PROVIDING A SINGLE USE IMAGING DEVICE FOR MEDICAL APPLICATIONS; U.S. Pat. No. 9,123,602 entitled PIXEL ARRAY AREA OPTIMIZATION USING STACKING SCHEME FOR HYBRID IMAGE SENSOR WITH MINIMAL VERTICAL INTERCONNECTS; U.S. Pat. No. 9,153,609 entitled IMAGE SENSOR WITH TOLERANCE OPTIMIZING INTERCONNECTS; U.S. Pat. No. 9,462,234 entitled CAMERA SYSTEM WITH MINIMAL AREA MONOLITHIC CMOS IMAGE SENSOR; U.S. Pat. No. 9,509,917 entitled WIDE DYNAMIC RANGE USING MONOCHROMATIC SENSOR; and U.S. Pat. No. 9,622,650 entitled SYSTEM AND METHOD FOR SUB-COLUMN PARALLEL DIGITIZERS FOR HYBRID STACKED IMAGE SENSOR USING VERTICAL INTERCONNECTS, each of which is incorporated herein by reference.

The camera module 102 can include a lens or optical element 114 configured to direct light onto the image sensor 112. The lens 114 can be a static lens. The lens 114 can be a monolithic block of optically-transparent material. The lens 114 can be polymeric. The lens 114 can have a fixed focal length or can have an adjustable focal length. The lens 114 can include a mechanical shutter. The lens 114 can include multiple optical elements movable relative to one another. The lens 114 can include one or more motors, actuators, gears, etc. for adjusting the focal length, aperture size, shutter speed, and other parameters of the lens. The camera module 102 can include a modular lens receiver such that a user can attach any of a variety of lenses to the camera module. Exemplary lenses 114 can include prime lenses, normal lenses, wide-angle lenses, fisheye lenses, telephoto lenses, zoom lenses, anamorphic lenses, catadioptric lenses, lenses of varying focal lengths or varying ranges of focal lengths, etc. The lens 114 can include a high speed autofocus. The lens 114 can include an adjustable aperture and an adjustable shutter speed.

The camera module 102 can include an illumination system for illuminating a field of view of the image sensor 112. The illumination system can include a digital or analog light source. The light source can include one or more laser emitters or light-emitting diodes, an incandescent bulb, or the like. The light source can emit light in any dithered, diffused, or collimated emission and can be controlled digitally or through analog methods or systems. The light source can be pulsed to illuminate a surgical scene. The light source can pulse in one or more partitions, where each partition is a pre-determined range of wavelengths of the electromagnetic spectrum that is less than the entire electromagnetic spectrum. The pixel array of the image sensor 112 can be paired with the light source electronically, such that they are synced during operation for both receiving emissions of reflected electromagnetic radiation and for the adjustments made within the system. The light source can be tuned to emit electromagnetic radiation. The light source can pulse at an interval that corresponds to the operation and functionality of the pixel array. The light source can pulse light in a plurality of electromagnetic partitions, such that the pixel array receives reflected electromagnetic energy and produces a data set that corresponds (in time) with each specific electromagnetic partition. For example, the light source can emit a green electromagnetic partition, a blue electromagnetic partition, and a red electromagnetic partition in any desired sequence which can be combined to form a color image. Any color combination or any electromagnetic partition can be used in place of the red partition, green partition, and blue partition, such as cyan, magenta, and yellow, ultraviolet, infra-red, or any other combination, including all visible and non-visible wavelengths. Exemplary illumination systems, and other features that can be included or incorporated in the camera module 102, are disclosed in U.S. Pat. No. 9,516,239 entitled YCBCR PULSED ILLUMINATION SCHEME IN A LIGHT DEFICIENT ENVIRONMENT; and U.S. Pat. No. 9,641,815 entitled SUPER RESOLUTION AND COLOR MOTION ARTIFACT CORRECTION IN A PULSED COLOR IMAGING SYSTEM, each of which is incorporated herein by reference.

The light source can be disposed within the housing 104, or can be disposed remotely from the housing. For example, the illumination system can include an optical fiber 116 having a distal end disposed within or in close proximity to the housing 104 and a proximal end in optical communication with a light source disposed remotely from the housing. The optical fiber 116 can direct light emitted from the light source into the field of view of the image sensor 112. The illumination system can include an optical element 118 for adjusting various illumination properties. Exemplary optical elements 118 can include diffusers, filters, and so forth. In the illustrated embodiment, the camera module 102 includes an optical element 118, which is illustrated as a diffuser, disposed over the terminal distal end of an optical fiber 116.

The camera module 102 can include a printed circuit board assembly (PCBA) 120. The image sensor 112 can be mounted directly to the PCBA 120, or can be operably coupled thereto, e.g., using a connector 122. The PCBA 120 can include power conditioning circuitry, hardware logic, clocks, and/or other components for operating the image sensor 112 and communicating image data generated by the image sensor to the controller 106.

One or more of the above camera module 102 components can be mounted in a frame or lens barrel 124. The lens barrel 124 can include an outer sidewall having one or more channels or lumens formed therein. For example, as shown, the lens barrel 124 can include a lens lumen 126 and an illumination lumen 128.

The lens lumen 126 can include proximal and distal ends 126p, 126d and a central longitudinal axis A1. The lens lumen 126 can have a circular transverse cross-section. The lens 114 can be disposed within a distal end of the lens lumen 126. The image sensor 112 can be positioned at or in a proximal end of the lens lumen 126. The lens lumen 126 can be open at its proximal and distal ends and closed along its sides as shown, or a portion or all of the lens lumen can be open to an outer sidewall of the lens barrel 124.

The illumination lumen 128 can include proximal and distal ends 128p, 128d and a central longitudinal axis A2. The illumination lumen 128 can have a circular transverse cross-section. The optical fiber 116 can be disposed within the illumination lumen 128. The illumination lumen 128 can be open at its proximal and distal ends and closed along its sides or, as shown, a portion or all of the illumination lumen can be open to an outer sidewall of the lens barrel 124. This can facilitate insertion of the optical fiber 116 into the lens barrel 124 during assembly, e.g., by allowing the optical fiber to be side-loaded or laterally-inserted into the illumination lumen 128. The distal end of the illumination lumen 128 can be curved or angled, e.g., such that it extends in a direction that is not parallel to the axis A2. This arrangement can allow a planar distal end of a straight-cut optical fiber 116 to be oriented parallel to an angle-cut distal end of the lens barrel 124, as shown. In other arrangements, the optical fiber 116 can be angle-cut to match the distal end of the lens barrel 124.

The lumens 126, 128 can be coaxial with one another or can be non-coaxial. For example, the lumens 126, 128 can be laterally offset from each other. The lumens 126, 128 can be formed such that they extend parallel to one another, e.g., such that their respective central longitudinal axes A1, A2 are parallel. As described further below, when integrated with an access device 110, the illumination lumen 128 can be disposed radially-inward from the lens lumen 126, e.g., such that the illumination lumen is disposed closer to the center of the access device working channel than the lens lumen. This can provide a more even distribution of light within the working channel of the access device 110.

The proximal end of the lens barrel 124 can include a recess or pocket 130. The image sensor 112 can be disposed within the recess 130. An image sensor connector 122 and/or at least a portion of the PCBA 120 can be disposed within the recess 130. The lens barrel 124 can include an internal baffle 132 disposed between the lens 114 and the image sensor 112. The baffle 132 can include an aperture through which light passing through the lens 114 can be communicated to the image sensor 112. The aperture can have a fixed dimension or can be mechanically-adjustable.

The lens barrel 124 can include a distal-facing surface at a terminal distal end thereof. The lumens 126, 128 of the lens barrel 124 can be open to the distal-facing surface. The distal facing surface can be obliquely angled. For example, the distal facing surface can lie substantially in a plane that is obliquely angled with respect to the central axis A1 of the lens lumen 126, obliquely angled with respect to the central axis A2 of the illumination lumen 128, and/or obliquely angled with respect to the central longitudinal axis of a working channel or access device in which the camera module 102 is disposed. The lens 114 can be flush with the distal-facing surface as shown, or can be recessed or protruding therefrom. The distal-facing surface can include a recess 134 in which the diffuser or other optical element 118 of the illumination system can be disposed. The recess 134 can be formed about the perimeter of the illumination lumen 128. The recess 134, and the optical element 118 disposed therein, can have a curved or crescent shape as shown. The recess 134 can include an inner edge that follows or substantially follows the perimeter of the lens lumen 126.

As described further below, when integrated with an access device 110, the distal-facing surface of the lens barrel 124 can be angled, in a distal-to-proximal direction, towards the center of the access device or a working channel thereof in which the camera module 102 is disposed. This can provide a better view of the surgical site for the image sensor 112 and/or a more even distribution of light within the surgical site. The lens barrel 124 can have a transverse exterior cross-section that is oval, oblong, circular, elliptical, square, rectangular, etc.

As shown in FIGS. 3A-3J, the camera module 102 can be mounted in the housing 104. The housing 104 can include a main body 136 and a distal end cap 138. As described further below, the end cap 138 can be configured to direct the fluid across the lens 114 and/or the illumination system of the camera module 102, e.g., to clear obstructions therefrom. The housing 104 can be rigid or flexible. The housing 104 can be made as short as possible to facilitate positioning of the housing within an access device 110. The housing 104 can have a length that is less than about 60 mm. For example, the housing 104 can have a length of about 45 mm or that is less than about 45 mm.

The main body 136 of the housing 104 can include a proximal-facing surface 136p, a distal-facing surface 136d, and a sidewall 136s connecting the proximal-facing and distal-facing surfaces. One or more channels or lumens can be formed in the main body 136. The main body 136 can be formed by extrusion of a multi-lumen shaft. The main body 136 can be formed by welding or otherwise attaching multiple longitudinal components to one another.

The main body 136 can include a camera lumen 140 in which the camera module 102 can be selectively mounted. At least a portion of the camera lumen 140 can be lined with or can otherwise include a metallic tube, which can provide electromagnetic shielding for the components of the camera module 102.

The main body 136 can include one or more fluid lumens 142. For example, in the illustrated embodiment, the main body 136 includes a first fluid lumen 142A, which can be used to convey material from a proximal end of the housing 104 to a distal end of the housing, and a second fluid lumen 142B, which can be used to convey material from a distal end of the housing to the proximal end of the housing. While first and second fluid lumens 142 are shown, the housing 104 can include any number of fluid lumens. The first and second lumens 142 can form part of a lens cleaning system in which cleaning fluid or media is delivered through one lumen to deliver the cleaning fluid to the distal end of the camera module 102 and suction or vacuum is applied to the other lumen to draw cleaning fluid, tissue, debris, or other material away from the camera module. Each of the lumens 142 can include a fluid connector or coupling 144 at a proximal end thereof for establishing fluid communication between the lumens and the connector assembly 108. The fluid connectors 144 can be male barbed fittings that extend proximally from the proximal-facing surface 136p of the main body 136 as shown, or can be any other type of fluid fitting or connection, such as a luer connection, a female fitting, etc.

The lumens 140, 142 of the housing 104 can be co-axial, non-coaxial, or some lumens can be coaxial while others are non-coaxial. The camera lumen 140 can be disposed centrally between first and second fluid lumens 142 as shown. The lumens 140, 142 of the housing 104 can be parallel to one another. The lumens 140, 142 can have various shapes. The lumens 140, 142 can have a transverse interior cross-section that is oval, oblong, circular, elliptical, square, rectangular, etc. The camera lumen 140 can have an interior shape that matches the exterior shape of the camera module 102, or the lens barrel 124 thereof.

The distal facing surface 136d of the main body 136 can be obliquely angled. For example, the distal facing surface 136d can lie substantially in a plane that is obliquely angled with respect to a central longitudinal axis A3 of the housing 104 and/or obliquely angled with respect to the central longitudinal axis of a working channel or access device in which the housing is disposed. The distal-facing surface 136d of the main body 136 can be angled in the same manner as the distal-facing surface of the camera module 102 or lens barrel 124. The distal-facing surface of the camera module 102 can be flush with the distal-facing surface 136d of the main body 136, or can be recessed or protruding relative thereto.

The sidewall 136s of the housing 136 can have any of a variety of shapes. The sidewall 136s can have a transverse exterior cross-section that is substantially triangular, crescent shaped, circular, square, or rectangular. The sidewall 136s can be cylindrical. The sidewall 136s can be curved. The sidewall 136s can be shaped to facilitate integration of the housing 104 with an access device 110, e.g., to reduce or eliminate the degree to which the housing interferes with a working channel of the access device. The sidewall 136s can include an inner portion 136i that is concave. The inner portion 136i can be curved. The inner portion 136i can form a section of a working channel of an access device 110, e.g., a cylindrical or elliptical working channel. The sidewall 136s can include an outer portion 136o that is convex. The outer portion 136o can be curved. As shown for example in FIG. 3E, the sidewall 136s can include an outer portion 136o having first and second planar regions connected by a central transition region that defines a section of a cylinder. The transition region can follow the outer perimeter of the camera lumen 140. As also shown for example in FIG. 3E, the sidewall 136s can include an inner portion 136i that is concavely curved and connected to the outer portion 136o by first and second transition regions that define sections of respective cylinders. The first and second transition regions can follow the outer perimeters of the fluid lumens 142.

Figure 3A:
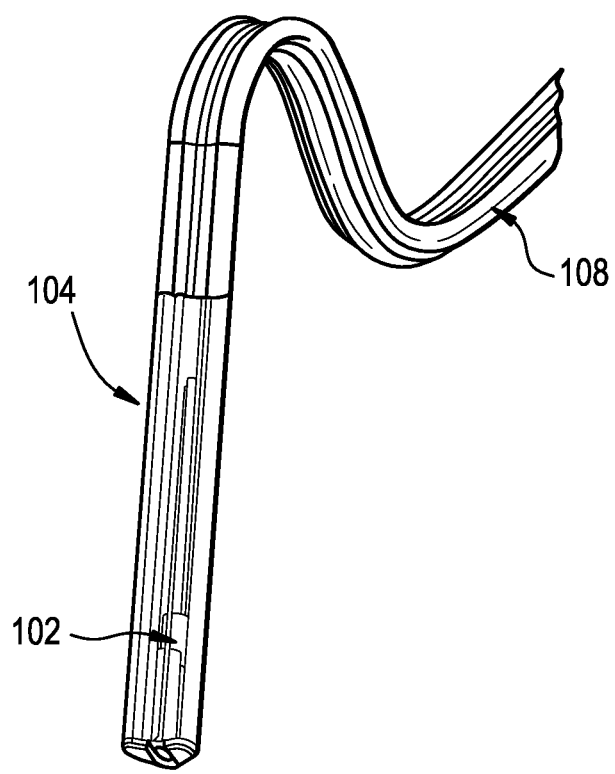
FIG. 3A is a perspective view of a housing of the system of FIG. 1, with the housing shown as transparent and with the camera module of FIG. 2A disposed therein.
Figure 3B:
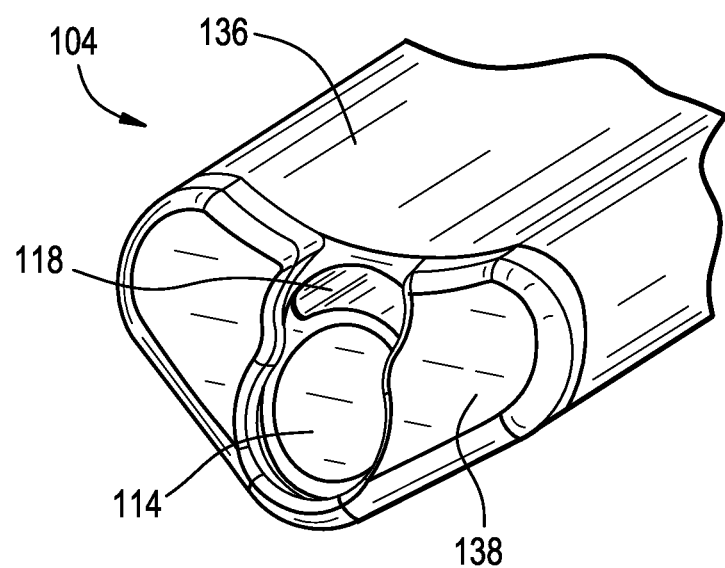
FIG. 3B is a perspective view of the distal end of the housing and camera module of FIG. 3A.
Figure 3E:
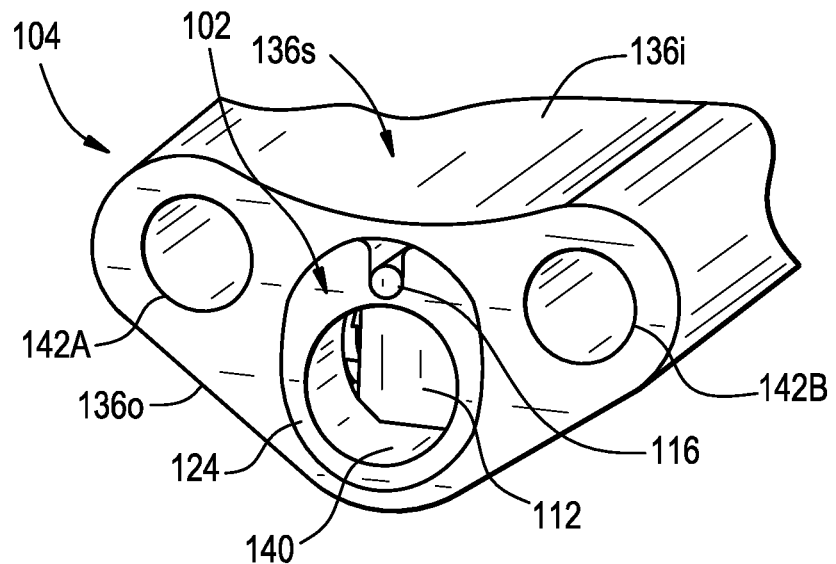
FIG. 3E is a sectional perspective view of the housing and camera module of FIG. 3A, adjacent a distal end thereof.
Figure 3F:
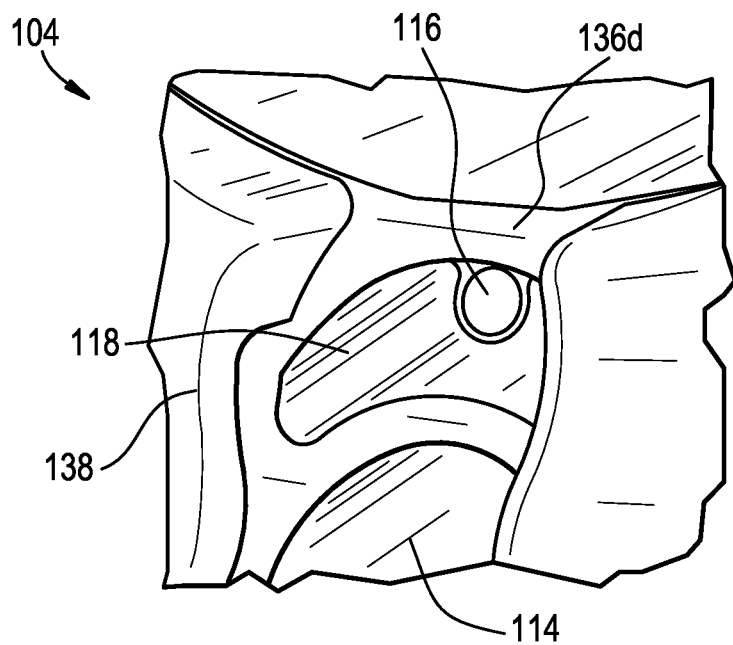
FIG. 3F is a perspective view of the distal end of the housing and camera module of FIG. 3A.
Figure 3G:
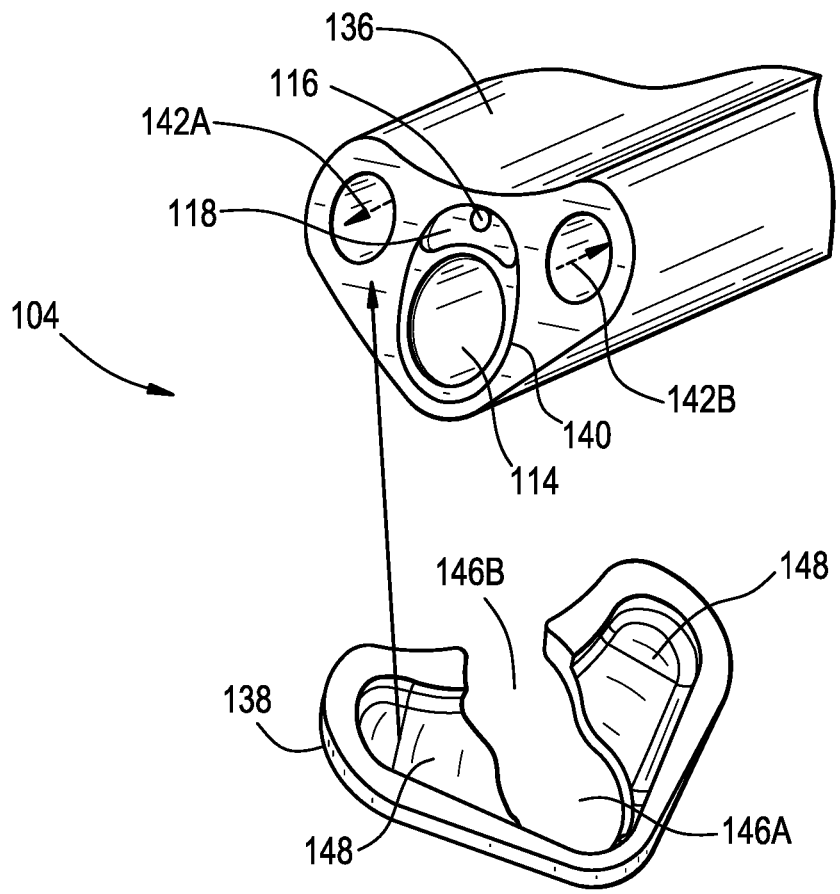
FIG. 3G is a partially exploded perspective view of the housing and camera module of FIG. 3A.
Figure 3H:
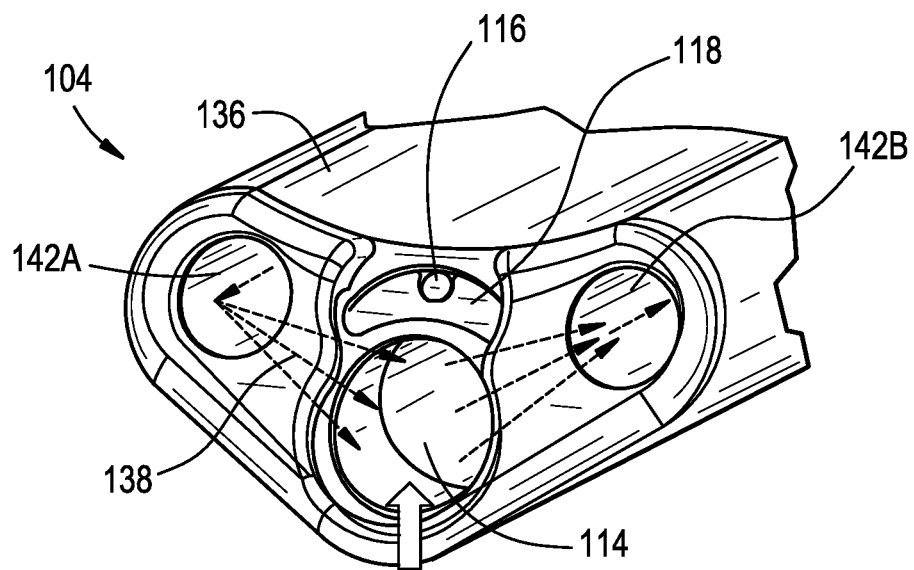
FIG. 3H is a perspective view of the housing and camera module of FIG. 3A, with an end cap of the housing shown as transparent and schematically illustrating fluid flow through the housing.
Figure 3I:
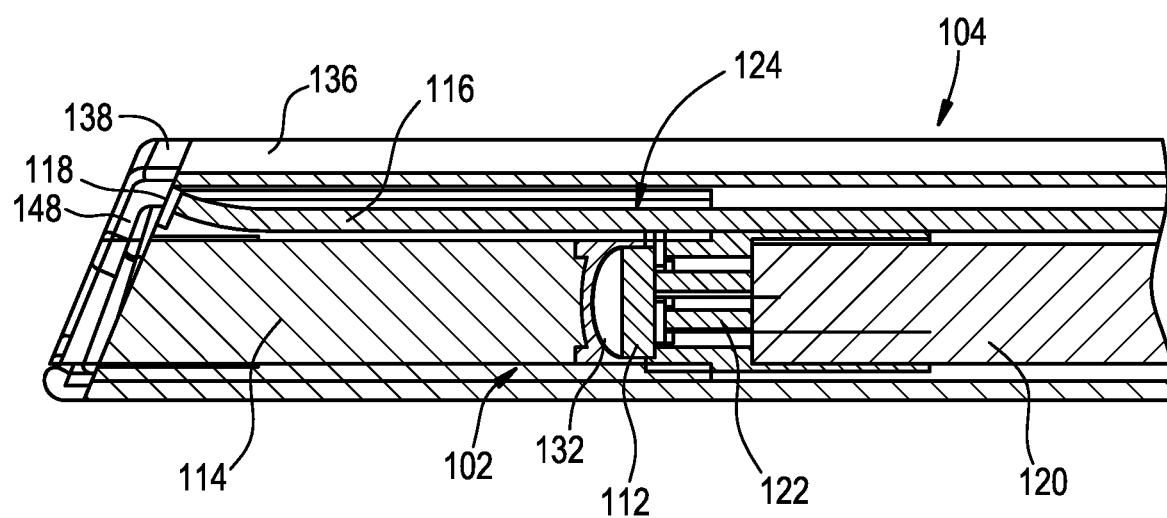
FIG. 3I is a sectional side view of the housing and camera module of FIG. 3A.
Figure 3J:
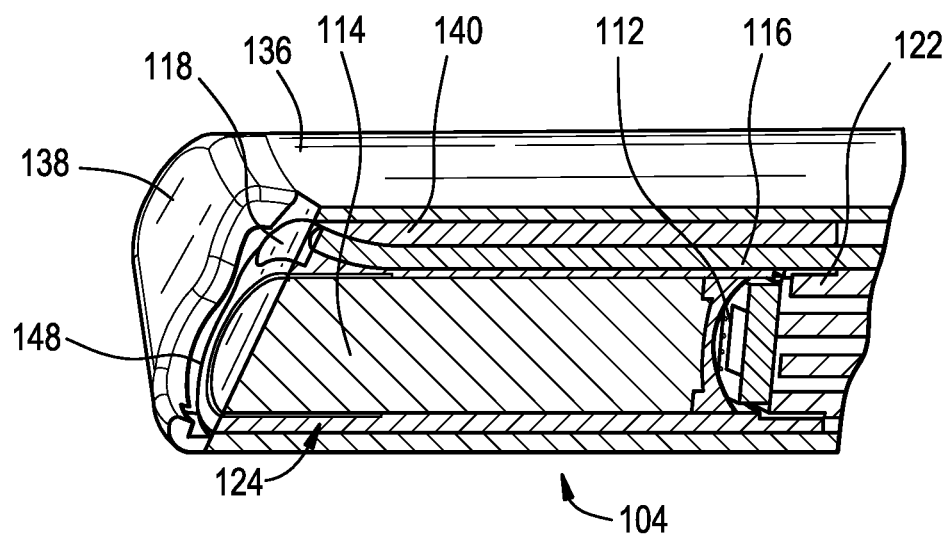
FIG. 3J is a sectional perspective view of the housing and camera module of FIG. 3A.

The end cap 138 of the housing 104 can be coupled to the distal end of the main body 136. An exterior sidewall of the end cap 138 can have a shape that matches that of the sidewall of the main body 136. The end cap 138 can include one or more cut-outs 146 formed therein. The end cap 138 can include a first cut-out 146A aligned with the lens 114 of the camera module 102 to allow light to pass through the end cap and into the lens. The end cap 138 can include a second cut-out 146B aligned with the illumination system of the camera module 102 to allow light to pass through the end cap and into the surgical site. The first and second cut-outs 146 can be discrete cut-outs or can be contiguous as shown. The first and second cut-outs 146 can be circular, can have a shape that matches that of the lens 114 or illumination system, or can be otherwise shaped to function as described above. A proximal-facing surface of the end cap 138 can include one or more recesses, grooves, or channels 148 for directing fluid flow. Alternatively, the proximal-facing surface of the end cap 138 can be a flat planar surface and the recesses, grooves, or channels 148 can be formed in the distal-facing surface of the main body 136. Lateral endportions of the recesses 148 can be axially aligned with the fluid lumens 142 of the main body 136. Medial endportions of the recesses 148 can be open to the cut-outs 146 and/or to the distal-facing surface of the lens 114 and the illumination system. In use, as shown in FIG. 3H, fluid exiting the first lumen 142A of the main body 136 can be directed by the end cap 138 across the lens 114 and the illumination system (e.g., the diffuser or optical element 118 of the illumination system) and towards the distal entrance of the second fluid lumen 142B, e.g., along the path of the illustrated arrows. It will be appreciated that fluid can alternatively be directed in an opposite direction. The recesses 148 can include baffles, nozzles, diverters, or other structures for tailoring the flow of fluid across the lens 114 and/or the illumination system. In some embodiments, fluid flow can be substantially contained to the interior of the end cap, e.g., without irrigating the surgical site or a working channel of an access device in which the housing 104 is mounted. Containing the fluid flow in this manner can be particularly useful in "dry environment" procedures such as a lumbar TLIF procedure. Containing the fluid flow can help limit bleeding and possible tissue damage. In other embodiments, the fluid is not contained to the end cap and can be used to irrigate the surgical site and/or working channel.

Figure 4A:
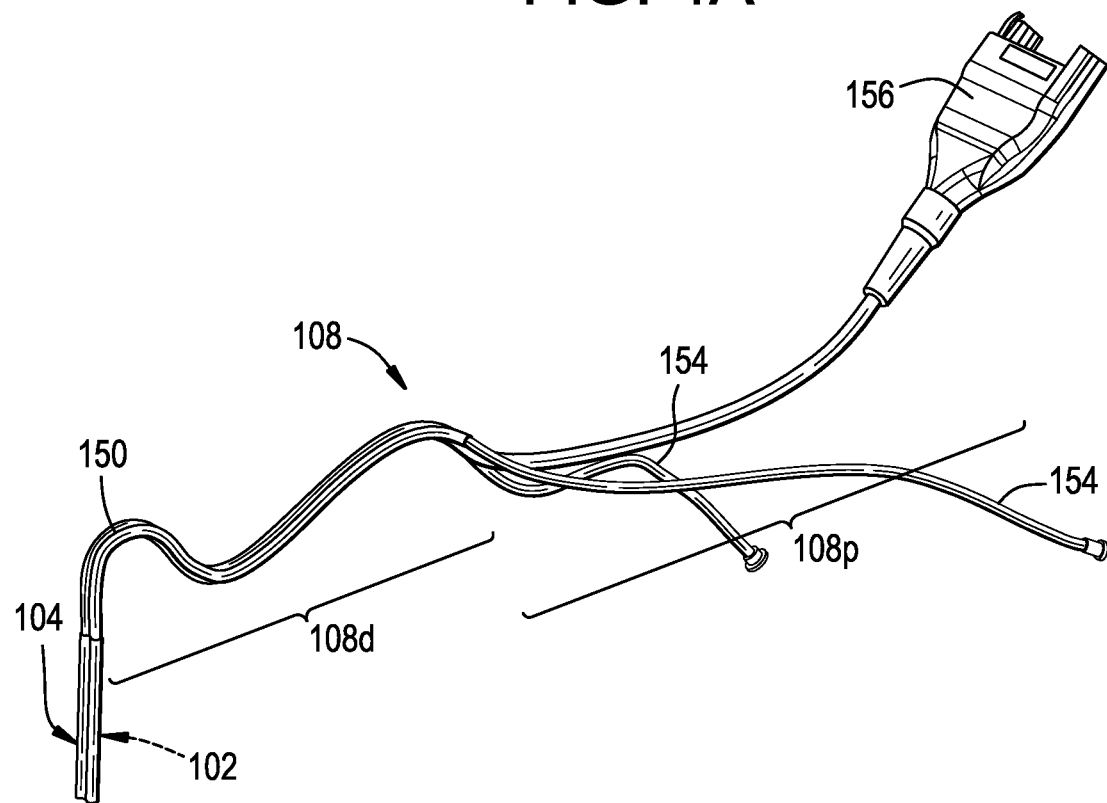
FIG. 4A is a perspective view of a connector assembly of the system of FIG. 1.
Figure 4B:
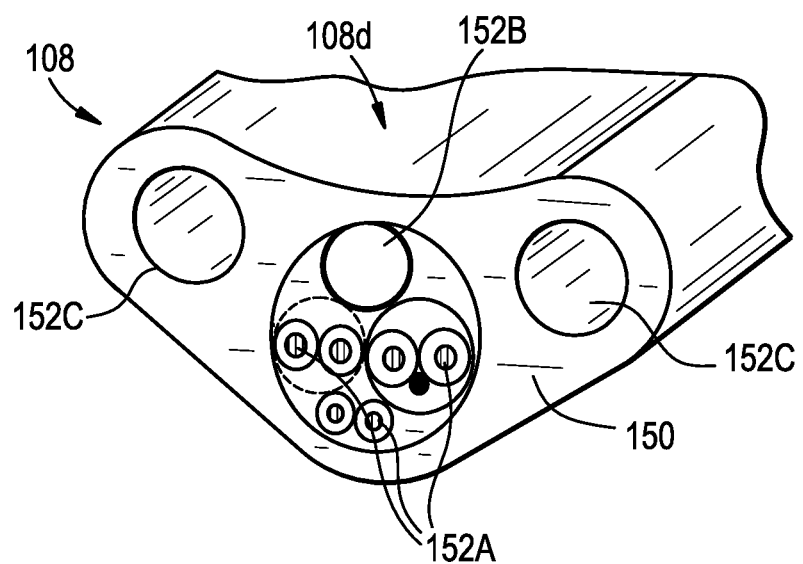
FIG. 4B is a sectional perspective view of the connector assembly of FIG. 4A, adjacent a distal end thereof.

The housing 104 and/or the camera module 102 can be coupled to the controller 106 via a connector or connector assembly 108. An exemplary connector assembly 108 is shown in FIGS. 4A-4B. The connector assembly 108 can include one or more conductors therein. The connector assembly 108 can include fluid conductors for delivering fluid to or from the housing 104. The connector assembly 108 can include optical conductors for delivering light to or from the camera module 102. The connector assembly 108 can include electrical conductors for communicating image data, control signals, or other information between the controller 106 and the camera module 102. The conductors can be disposed partially or entirely within an outer sheath 150 of the connector assembly 108.

The connector assembly 108 can include a distal section 108d and a proximal section 108p. In the distal section 108d, all of the conductors of the connector assembly 108 can be disposed within the outer sheath 150. In the proximal section 108p, one or more of the conductors can exit the outer sheath 150 and can extend separately therefrom. For example, in the illustrated embodiment, the distal section 108d of the connector assembly 108 includes electrical conductors 152A, one or more optical fibers 152B, and first and second fluid lumens 152C all extending through a common outer sheath 150. Also in the illustrated embodiment, the proximal section 108*p* of the connector assembly 108 is configured such that the electrical conductors 152A and one or more optical fibers 152B continue through the common outer sheath 150 while the first and second fluid lumens 152C exit the outer sheath as discrete fluid tubes 154. The outer sheath 150 can include a mechanical connector 156 at a proximal end thereof for making optical and/or electrical connections with the controller 106. The fluid tubes 154 can include respective fluid fittings or connectors for making fluid connections, e.g., with a fluid reservoir and/or vacuum source of the controller 106 or separate from the controller.

The distal section 108*d* of the connector assembly 108 can have an exterior shape that matches that of the housing 104, e.g., as shown in FIG. 4B. The distal section 108*d* of the connector assembly 108 can mate with the housing 104 to define a seamless exterior transition. At least a portion of the connector assembly 108 can be flexible or bendable. As described further below, the distal section 108*d* of the connector assembly 108 can be flexible to facilitate integration of the system 100 with an access device 110.

Figure 5A:
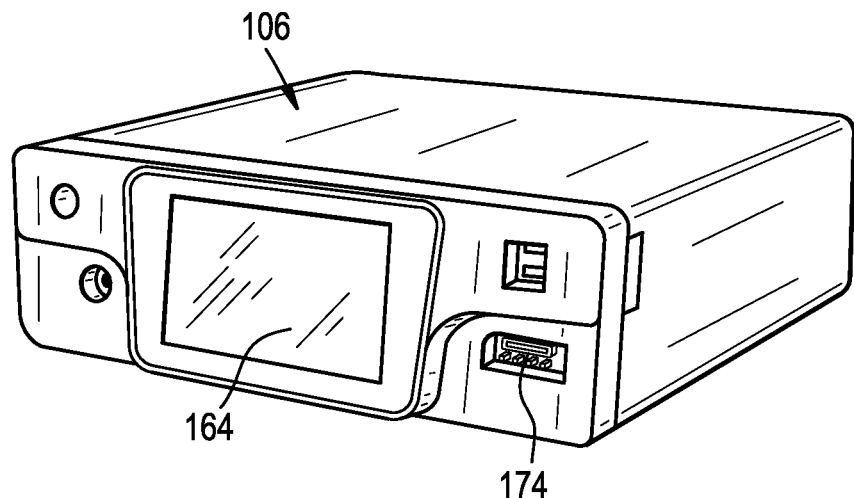
FIG. 5A is a perspective view of a controller of the system of FIG. 1.
Figure 5B:
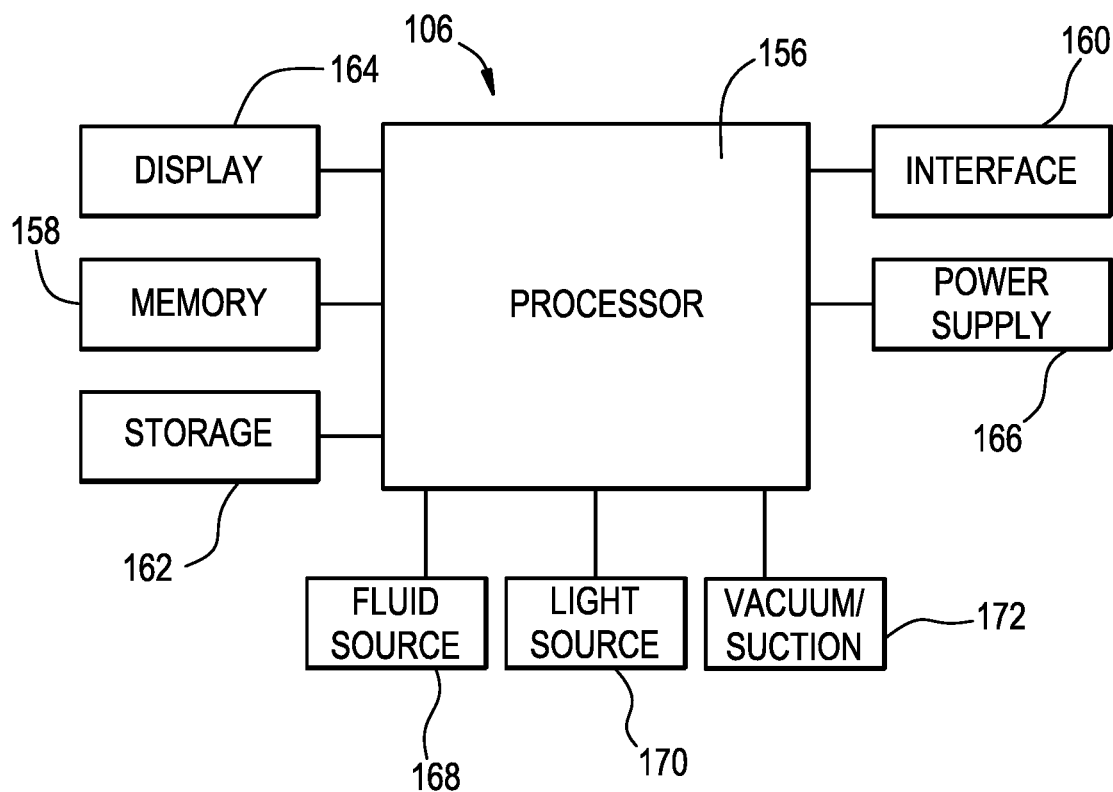
FIG. 5B is a schematic block diagram of the controller of FIG. 5A.

An exemplary controller 106 is shown in FIGS. 5A-5B. Although an exemplary controller 106 is depicted and described herein, it will be appreciated that this is for sake of generality and convenience. In other embodiments, the controller 106 may differ in architecture and operation from that shown and described here. The controller 106 can be a tablet computer, mobile device, smart phone, laptop computer, desktop computer, cloud-based computer, server computer, and so forth. The controller 106 can include a processor 156 for controlling operation of the controller 106, for example by executing embedded software, operating systems, device drivers, application programs, and so forth. The processor 156 can be or can include one or more microprocessors, microcontrollers, ASICs, FPGAs, PICs, processors that read and interpret program instructions from internal or external memory or registers, and so forth. The controller 106 can include a memory 158, which can provide temporary or permanent storage for code to be executed by the processor 156 or for data that is processed by the processor. The memory 158 can include read-only memory (ROM), flash memory, one or more varieties of random access memory (RAM), and/or a combination of memory technologies. The various components of the controller 106 can be interconnected via any one or more separate traces, physical busses, communication lines, etc.

The controller 106 can include an interface 160, such as a communication interface or an I/O interface. A communication interface can enable the controller 106 to communicate with remote devices (e.g., other controllers or computer systems) over a network or communications bus (e.g., a universal serial bus). An I/O interface can facilitate communication between one or more input devices, one or more output devices, and the various other components of the controller 106. Exemplary input devices include touch screens, mechanical buttons, keyboards, and pointing devices. The controller 106 can include a storage device 162, which can include any conventional medium for storing data in a non-volatile and/or non-transient manner. The storage device 162 can include one or more hard disk drives, flash drives, USB drives, optical drives, various media disks or cards, and/or any combination thereof. The controller 106 can include a display 164, and can generate images to be displayed thereon. The display 164 can be an electronic display, a vacuum fluorescent display (VFD), an organic light-emitting diode (OLED) display, or a liquid crystal display (LCD). The controller 106 can include a power supply 166 and appropriate regulating and conditioning circuitry. Exemplary power supplies include batteries, such as polymer lithium ion batteries, or adapters for coupling the controller 106 to a DC or AC power source (e.g., a USB adapter or a wall adapter).

The controller 106 can include a fluid source 168 that can be in fluid communication with a fluid lumen 152C of the connector assembly 108 when the connector assembly is attached to the controller 106. The fluid source 168 can include a reservoir of cleaning media. The cleaning media can be a flowable gas or liquid. The cleaning media can include one or more of carbon dioxide, saline, oxygen, air, water, and the like. The fluid source 168 can include a pump or other mechanism for urging cleaning media through the connector assembly 108 and the housing 104. The pump can be controlled by the processor 156 to execute a cleaning cycle. The cleaning cycle can be executed automatically, or in response to a user instruction. For example, the processor 156 can detect user actuation of a button, foot pedal, or other interface element and initiate a cleaning cycle in response thereto.

The controller 106 can include a light source 170 that can be optically coupled to an optical fiber 152B of the connector assembly 108 when the connector assembly is attached to the controller. Exemplary light sources include light-emitting diodes (LEDs), incandescent or fluorescent bulbs, etc.

The controller 106 can include a vacuum or suction source 172 that can be in fluid communication with a fluid lumen 152C of the connector assembly 108 when the connector assembly is attached to the controller. The controller 106 can include an onboard vacuum pump for generating suction, or can be configured to attach to a standard hospital or operating room vacuum supply. The suction source 172 can include a valve, regulator, or other component for adjusting the degree of suction applied to the housing 104 and/or for turning the suction on or off. The suction source 172 can be controlled by the processor 156, e.g., to execute a cleaning cycle. The cleaning cycle can be executed automatically, or in response to a user instruction. For example, as noted above, the processor 156 can detect user actuation of a button, foot pedal, or other interface element and initiate a cleaning cycle in response thereto.

The controller 106 can include one or more connectors 174 for mating with the connector 156 and/or the fluid couplings 154 of the connector assembly 108. When mated, the connectors can establish electrical, optical, and/or fluid connections between the controller 106 and the connector assembly 108. It will be appreciated that any one or more of the components above can be disposed external to the housing of the controller 106, and/or can be separate or isolated from the controller altogether. For example, any one or more of the fluid source 168, the light source 170, and the suction source 172 can be external to and/or separate from the controller 106.

The controller 106 can receive image data from the image sensor 112. The image data can be communicated via a wired or wireless connection. The image data can include still image data and/or video image data. The controller 106 can display the image data on an on-board display 164 of the controller, or on one or more external monitors or displays operably coupled to the controller. The image data can be displayed to a surgeon or other user to facilitate a surgical procedure. The controller 106 can display patient data, user interface controls for manipulating system settings, controls for capturing screen shots of displayed images, and so forth.

The various functions performed by the controller 106 can be logically described as being performed by one or more modules. It will be appreciated that such modules can be implemented in hardware, software, or a combination thereof. It will further be appreciated that, when implemented in software, modules can be part of a single program or one or more separate programs, and can be implemented in a variety of contexts (e.g., as part of an embedded software package, an operating system, a device driver, a standalone application, and/or combinations thereof). In addition, software embodying one or more modules can be stored as an executable program on one or more non-transitory computer-readable storage mediums.

The system 100 can be configured to be integrated or used with an access device. Exemplary access devices can include cannulas, retractors, tubes, and other structures for providing a working channel in a surgical application. The access device can define a working channel that extends from a surgical site, e.g., an intervertebral disc space or a spinal region proximate thereto, to a location outside a patient's body. The access device can include a visualization channel for receiving the housing 104 and the camera module 102 of the visualization system 100. The visualization channel can also receive at least a portion of the connector assembly 108. The visualization channel can be the same as the working channel, can be independent of the working channel, or can overlap or intersect with the working channel. At least a portion of the sidewall of the working channel can be defined by an exterior surface of the housing 104. The housing 104 and/or the camera module 102 can be disposed off-center within the access device. The housing 104 and/or the camera module 102 can be slidably and/or rotatably coupled to the access device.

The housing 104 and/or the camera module 102 can be axially translatable within the access device, e.g., in a proximal-distal direction, to adjust the depth of the camera module relative to the access device. For example, the housing 104 can be advanced distally relative to the access device to move the lens 114 and image sensor 112 closer to the surgical site. By way of further example, the housing 104 can be retracted proximally relative to the access device to move the lens 114 and image sensor 112 farther from the surgical site. The ability to reposition the camera module 102 within the access device can facilitate various surgical procedures. For example, in an exemplary TLIF procedure, the camera module 102 can be positioned relatively shallow within the access device when cutting through Kambin's triangle and can then be advanced deeper within the access device when performing subsequent discectomy. In some cases, the camera module 102 can be advanced distally into the disc space. The ability to reposition the camera module 102 can also allow the camera module to be a modular component interchangeably usable with many different types or sizes of access device, or with an adjustable-length access device.

An exemplary access device 110 is shown in FIGS. 6A-6H. The access device 110 can include an elongate body having proximal and distal ends.

The access device 110 can define a working channel 174 extending between the proximal and distal ends and having a central longitudinal axis A4. The working channel 174 can be cylindrical. The working channel 174 can have a circular transverse cross-section. The working channel 174 can have a diameter in the range of about 3 mm to about 30 mm, in the range of about 10 mm to about 20 mm, and/or in the range of about 12 mm to about 15 mm. The working channel 174 can have a diameter of about 15 mm. While a single working channel 174 is shown, the access device 110 can include any number of working channels. In use, instruments and/or implants can be disposed in, passed through, and/or inserted into the working channel 174 to perform a surgical procedure. In some embodiments, the access device 110 can be used to access an intervertebral disc space. A cutting instrument can be inserted through the working channel 174 to cut tissue, such as bone or disc tissue. An aspiration instrument can be inserted through the working channel 174 to aspirate material from the disc space, including excised bone or disc tissue. The cutting instrument and the aspiration instrument can be a single tool. An implant such as a fusion cage, a height and/or width expandable fusion cage, a disc prosthesis, or the like can be inserted into the disc space through the working channel 174.

The access device 110 can define a visualization channel 176. The visualization channel 176 can extend between the proximal and distal ends of the access device 110, or can extend along less than an entire length of the access device. The visualization channel 176 can include a central longitudinal axis A5. The central axis A5 of the visualization channel 176 can be disposed radially-outward from the central axis A4 of the working channel 174. The working channel 174 can have a greater transverse cross-sectional area than the visualization channel 176. The visualization channel 176 can be open to, or can intersect with, the working channel 174 along its length. The visualization channel 176 can be isolated or separate from the working channel 174.

The visualization channel 176 can have an interior transverse cross section that matches or substantially matches the exterior transverse cross-section of the housing 104. When disposed within the visualization channel 176, an exterior surface of the housing 104 can define at least a portion of the inner sidewall of the working channel 174. The working channel 174 can be cylindrical about the central axis A4 and the surface of the housing 104 that faces the working channel can form a section of a cylinder centered on the axis A4. The inner sidewall of the working channel 174 and the outer surface of the housing 104 can define a substantially smooth and continuous surface.

The access device 110 can include an attachment feature 180, e.g., for attaching the access device to a support or other object. The attachment feature 180 can be formed at a proximal end of the access device 110. For example, the access device 110 can include an annular circumferential groove 180 formed in an exterior surface thereof.

The access device 110 can include a mating feature 178 for stabilizing, holding, and/or attaching the visualization system 100 to the access device. The mating feature 178 can be a proximal extension of the access device 110 as shown. The mating feature 178 can define one or more tracks 182 configured to receive the connector assembly 108 therein. The tracks 182 can be open to one side such that the connector assembly 108 can be loaded laterally into the track, e.g., by moving the connector assembly away from the central axis A5 of the visualization channel 176. Alternatively, or in addition, the connector assembly 108 can be loaded into the mating feature 178 by translating the connector assembly proximally or distally relative thereto.

One or more of the tracks 182 can define a connector path that is curved or obliquely-angled away from the central axis A5 of the visualization channel 176. The track 182 can have an interior transverse cross-section that matches or substantially matches the exterior transverse cross-section of the connector assembly 108. The track 182 can extend around the outer periphery of the connector assembly 108. The track 182 can extend around the connector assembly 108 to a sufficient degree that the free edges of the track interfere slightly with side-loading of the connector assembly into the track. Accordingly, slight deformation or deflection of the connector assembly 108 and/or the mating feature 178 can be required to load the connector assembly into the track 182. This can allow the connector assembly 108 to be held securely by the mating feature 178, e.g., by "snapping" the connector assembly into the track 182.

Figure 6A:
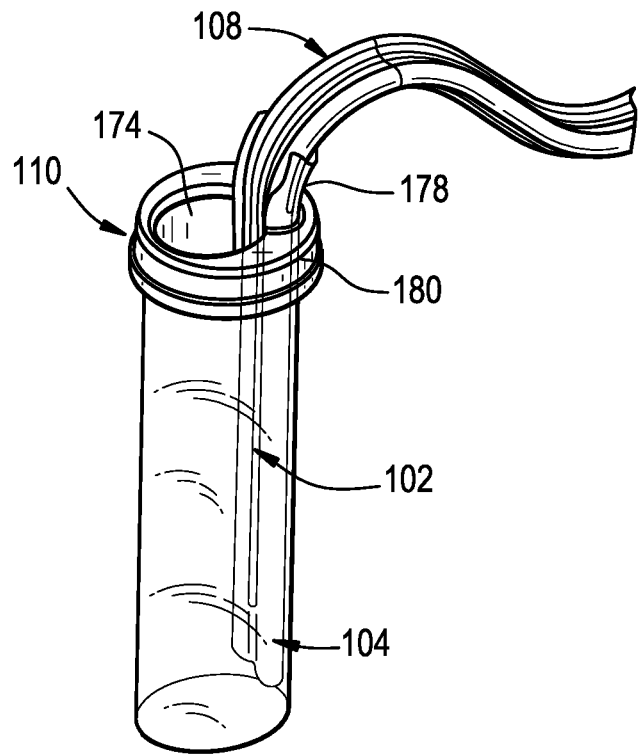
FIG. 6A is a perspective view of the system of FIG. 1 disposed in an access device, with the access device shown as transparent.
Figure 6B:
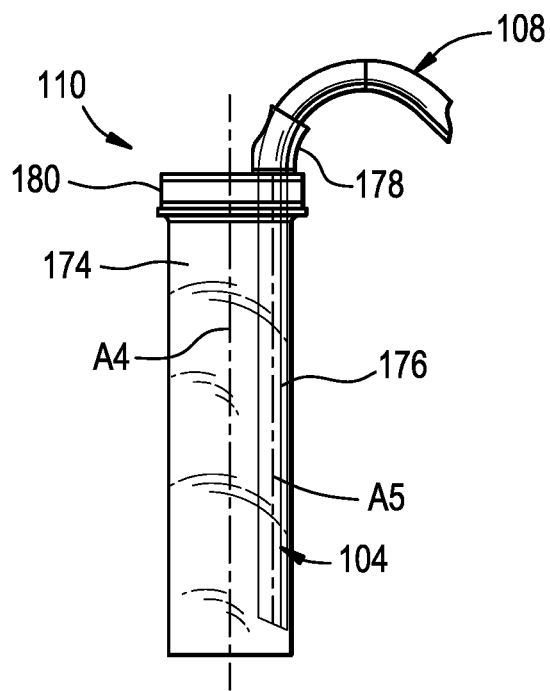
FIG. 6B is a side view of the system and access device of FIG. 6A, with the access device shown as transparent.
Figure 6E:
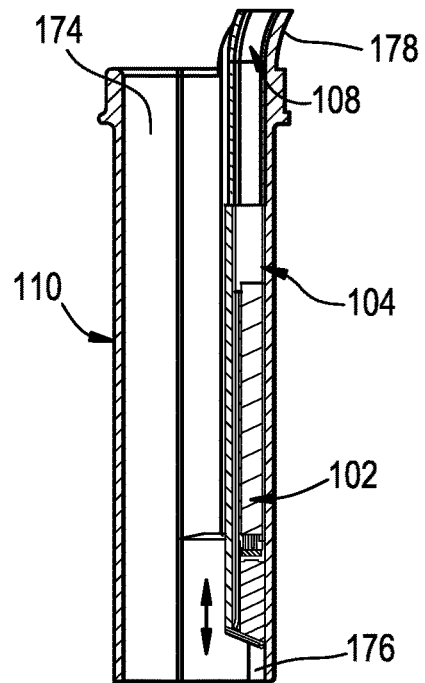
FIG. 6E is a sectional side view of the system and access device of FIG. 6A.
Figure 6F:
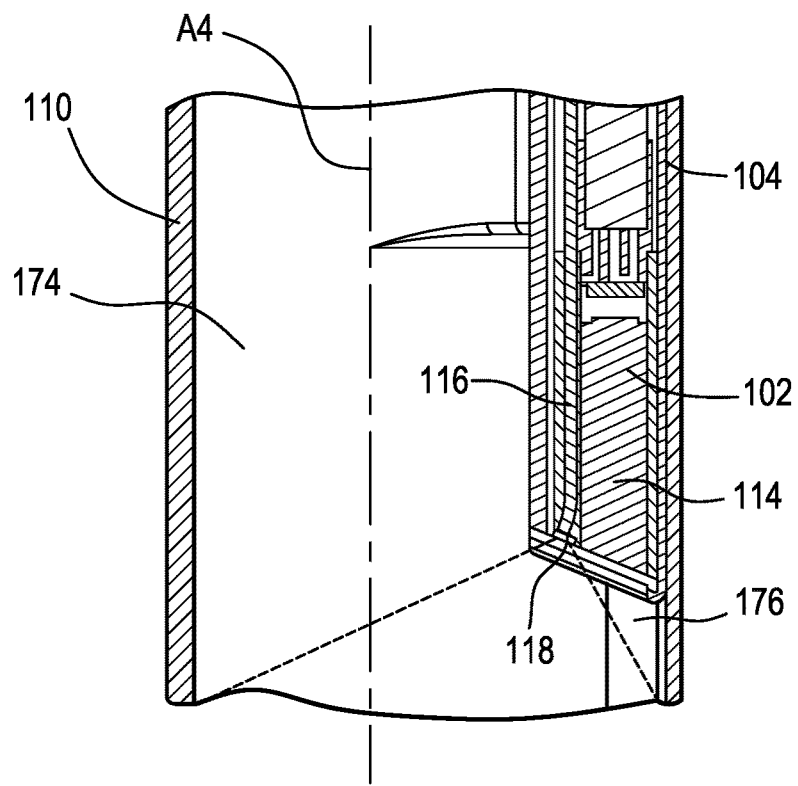
FIG. 6F is a sectional side view of the distal end of the system and access device of FIG. 6A.
Figure 6G:
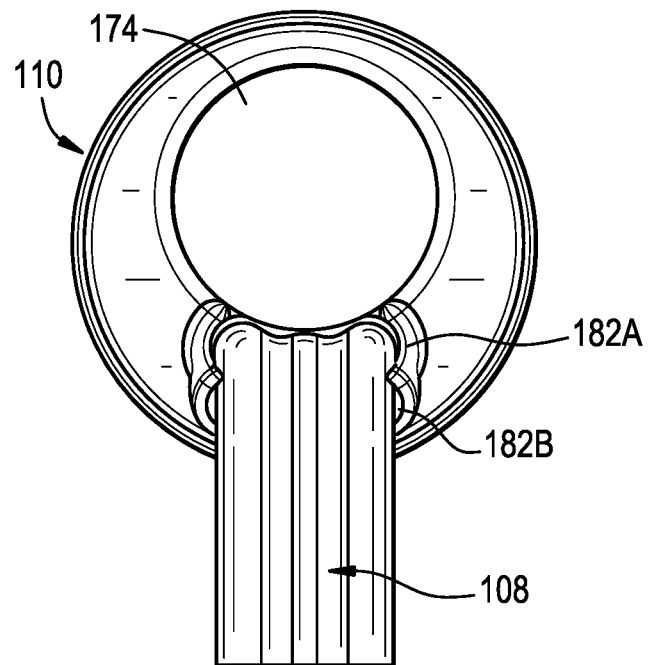
FIG. 6G is a top view of the system and access device of FIG. 6A.

The mating feature 178 can include inner and outer tracks 182A, 182B, e.g., as shown in FIGS. 6C, 6D, and 6G. The tracks 182 can include interfering edges of the type described above to restrict movement of the connector assembly 108 into and out of the tracks, but to allow such movement when sufficient force is applied, e.g., when the user specifically intends to perform such movement. The inner track 182A can be axially aligned with the visualization channel 176, or aligned therewith to a greater extent than the outer track 182B. The outer track 182B can be curved, obliquely angled, or otherwise axially offset from the visualization channel 176. When disposed in the inner track 182A, as shown in FIG. 6D, the connector assembly 108 can be retained to the access device 110, while still being able to translate proximally or distally relative to the access device with relatively little friction. When disposed in the outer track 182B, as shown in FIG. 6C, proximal-distal translation of the connector assembly 108 relative to the access device 110 can be limited or prevented, e.g., due to the curve of the connector assembly and/or due to increased friction between the connector assembly and the access device. In use, the connector assembly 108 can be positioned in the inner track 182A to adjust the height of the camera module 102 relative to the access device 110 and can be positioned in the outer track 182B to hold the camera module securely in place at a fixed height relative to the access device.

The connector assembly 108 can be secured to the mating feature 178 at any point along its length, e.g., at any point along the distal section 108d of the connector assembly. Accordingly, the visualization system 100 can be locked to the access device 110 at any inserted depth of the camera module 102. In addition, the visualization system 100 can be locked with the camera module 102 at a desired depth, regardless of the length of the access device 110, the position of the mating feature 178 along the access device, etc. This can allow the visualization system 100 to be interchangeably used with any of a variety of different type or size access devices 110.

The ability to lock the system 100 to the mating feature 178 can allow the camera module 102 to be used in a hands-free manner. In other words, the surgeon or other user does not need to manually grasp and/or hold the camera module 102 in place during use. The mating feature 178 can provide for simple, quick, and/or one-handed depth adjustment of the camera module 102, resulting in minimal delay and disruption to the procedure.

Figure 6H:
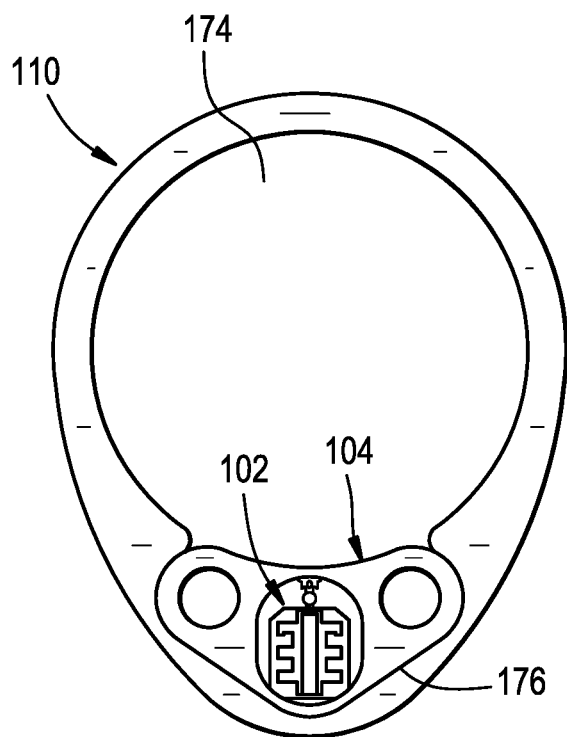
FIG. 6H is a sectional top view of the system and access device of FIG. 6A.

The access device 110 can have an exterior transverse cross section that is circular, e.g., as shown in FIG. 6G. The access device 110 can have an exterior transverse cross section that is oblong or egg-shaped, e.g., as shown in FIG. 6H. The access device 110 can include any of a variety of other exterior transverse cross sectional shapes. The access device 110 can have an external diameter or dimension in the range of about 5 mm to about 30 mm, in the range of about 10 mm to about 25 mm, and/or in the range of about 15 mm to about 22 mm. The access device 110 can have an external diameter or dimension of about 17 mm. The exterior surface of the access device 110 can be roughened, ribbed, milled, or coated with or formed from a material having a high coefficient of friction, which can advantageously improve grip and stability with surrounding tissue when the access device is inserted into a patient.

As noted above, and as shown in FIG. 6F, when disposed in the access device 110, the lens 114 of the camera module 102 can be aimed towards the central axis A4 of the working channel 174. Similarly, when so positioned, the illumination system of the camera module 102, e.g., the optical fiber 116 and/or the optical element 118, can be aimed towards the central axis A4 of the working channel 174. The illumination system can be disposed radially-outward from the central axis A4 of the working channel 174 and the lens 114 can be disposed radially-outward from the illumination system.

Figure 7:
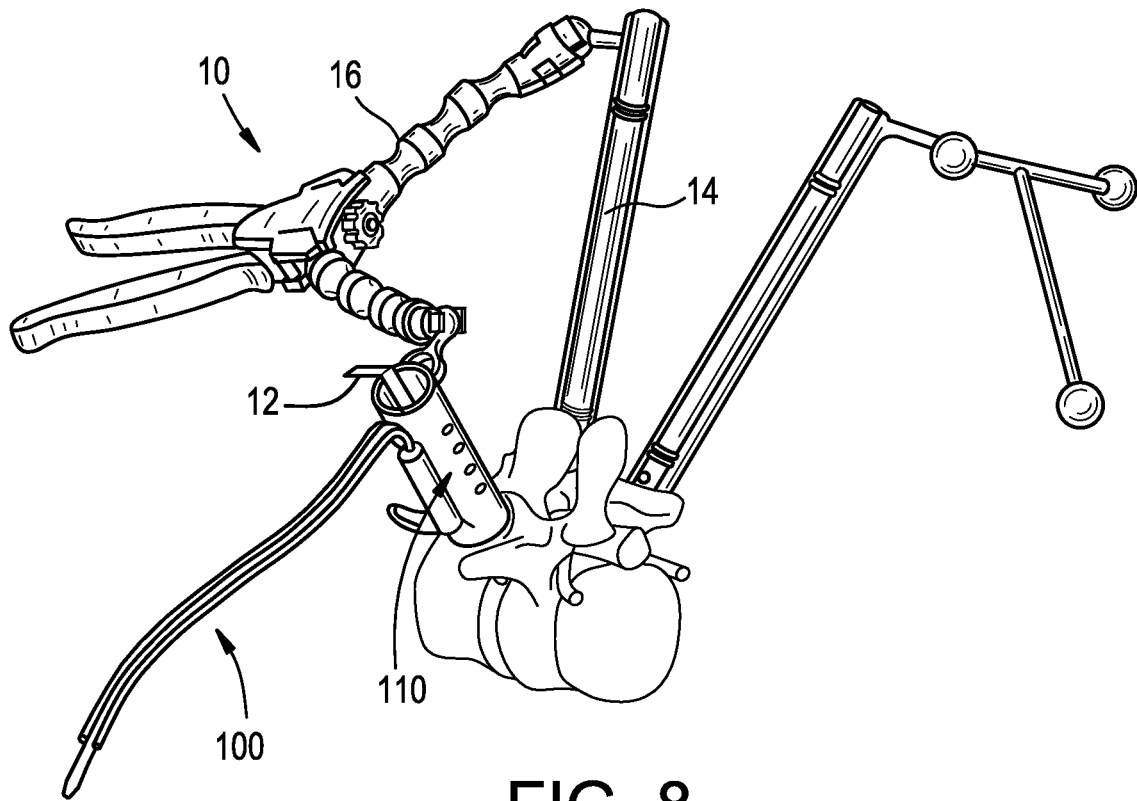
FIG. 7 is a perspective view of a surgical system, including the visualization system of FIG. 1, in use to perform a surgical procedure on a patient's spine.

FIG. 7 illustrates an exemplary surgical system 10 in which the devices and methods described herein can be used, though it will be appreciated that such devices and methods can be used in various other applications instead or in addition. Further details on the system of FIG. 7 can be found in U.S. application Ser. No. 15/437,792 filed on Feb. 21, 2017 (now issued as U.S. Pat. No. 10,874,425), which is hereby incorporated by reference herein. The system 10 can be used in various surgical procedures, including spinal surgeries such as microsurgical bone resection, spinal decompression, spinal fusion, and the like. In general, the system 10 can include any one or more of an access device 110, a tissue retractor 12, a pedicle post or other anchor 14, a connector 16, and a camera or visualization system 100. The access device 110 can be any of the access devices described herein. The visualization system 100 can be any of the visualization systems described herein.

An exemplary method of using the system 10 of FIG. 7 can include any one or more of the following steps, performed in any of a variety of sequences: a) making an incision in a skin of a patient; b) percutaneously inserting through the incision an access device 110 having a substantially tubular shape (such as a tube or a multi-slotted retractor), the access device having a length adapted to extend from the incision to a border between sensitive and insensitive tissue (e.g., a superior articular process (SAP), or a lamina) in the spine of the patient; c) stabilizing the access device to an anchor 14 (e.g., a pedicle anchor) using a connector 16; d) inserting an access device integrated optical visualization system 100, e.g., a visualization system of the type described herein; e) resecting a portion of the superior articular process, and/or performing a microsurgical decompression procedure; f) inserting or deploying a tissue retractor 12 through or from the access device so that a distal end portion of the tissue retractor extends to the intervertebral disc, the retractor having an outer surface; g) contacting the outer surface of the retractor to a nerve root to shield the nerve root; h) microsurgically decompressing any tissue deemed to be causing nerve impingement; i) extracting intervertebral disc material including removing cartilaginous material from the vertebral endplates; j) inserting an interbody device; and k) deploying a mechanism of stabilization to stabilize the intervertebral segment.

Figure 8:
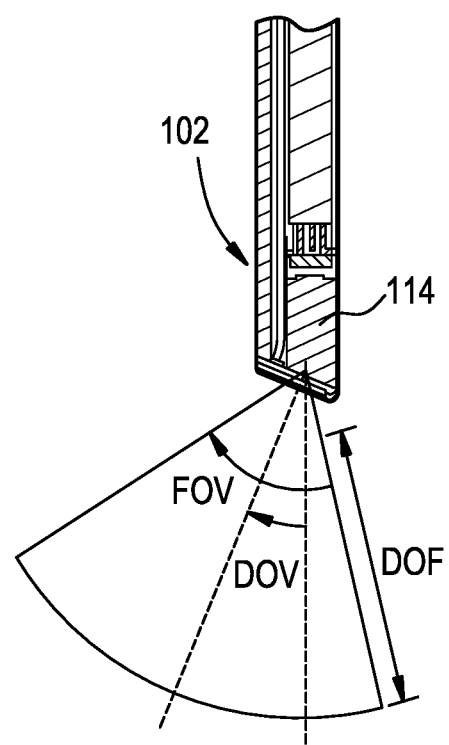
FIG. 8 is a sectional side view of the camera module of FIG. 2A, schematically illustrating viewing properties of the camera module.

Exemplary properties of the camera module 102 and the lens 114 thereof are shown in FIG. 8. The camera module 102 can have a field-of-view (FOV), a direction of view (DOV), and a depth of field (DOF). The FOV can be in the range of about 60 to about 70 degrees. The DOV can be in the range of about 15 to 30 degrees. The DOV can be in the range of about 20 to 25 degrees. The DOV can be about 22.5 degrees. The DOF can be in the range of about 7 mm to about 40 mm.

The system 100 can include active cleaning features. Active cleaning features can include application of an active force to the lens 114, the illumination system, or other components of the camera module 102. The active force can be or can include a fluid jet, fluid suction, mechanical or acoustic vibration, mechanical wipers, etc.

The system 100 can include passive cleaning features. The passive cleaning features can be used independently, or can augment or improve the performance of active cleaning features. As one example, the lens 114 can have a coating applied thereto to resist or prevent adhesion of debris to the lens. The coating can be hydrophilic. The coating can be oleophilic. The coating can be hydrophobic. The coating can be oleophobic. The coating can be a pollution-repellant coating. The coating can be a gradient coating, e.g., one in which a central region of the lens has a hydrophobic coating and a peripheral region of the lens has a hydrophilic coating. The gradient lens coating can be effective to "walk" or direct fluid from the center of the lens towards the outer periphery of the lens and out of the way of the image sensor 112.

Figure 9:
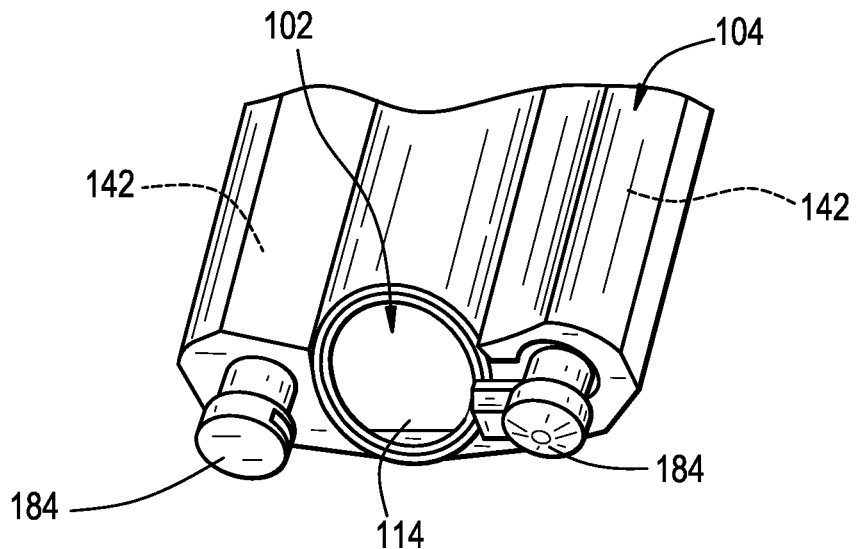
FIG. 9 is a perspective view of the distal end of another exemplary housing.

As shown in FIG. 9, the fluid lumens 142 of the housing 104 can each include a respective nozzle 184 disposed at a distal end thereof. The end cap 138 of the housing 104 can be omitted in such arrangements. The nozzles 184 can be configured to aim or direct the flow of fluid and/or suction forces towards the lens 114 or the illumination system of the camera module 102.

Figure 10A:
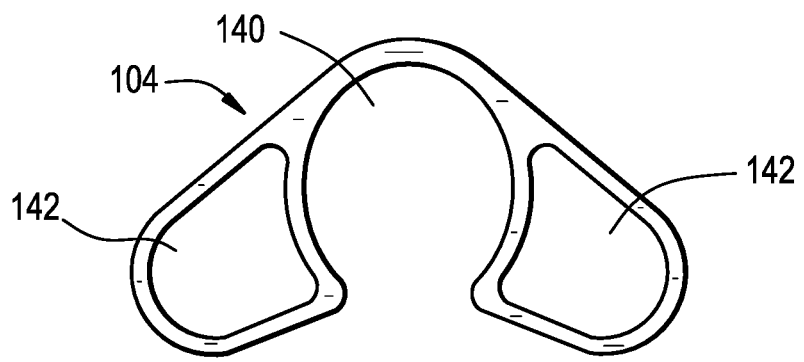
FIG. 10A is a sectional top view of another exemplary housing.

FIG. 10A illustrates another exemplary transverse cross-section of the housing 104. As shown, the fluid lumens 142 can be enlarged and can be non-circular. The fluid lumens 142 can be ear-shaped. The fluid lumens 142 can be asymmetrical.

Figure 10B:
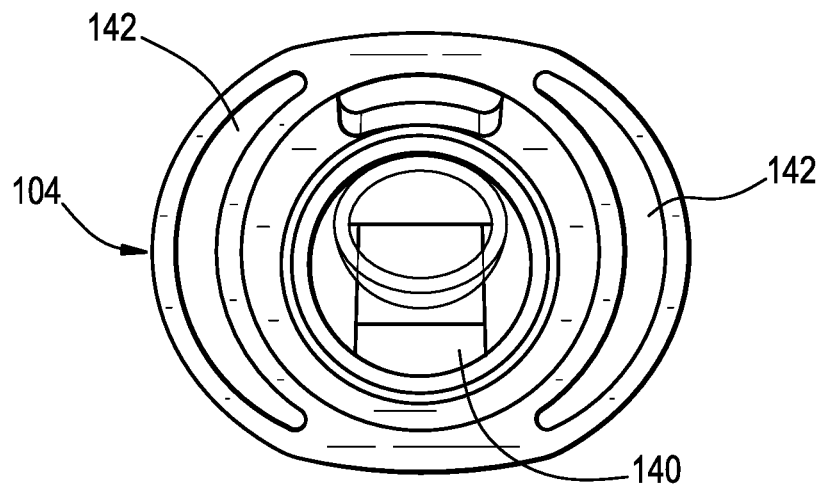
FIG. 10B is a sectional top view of another exemplary housing.
Figure 11A:
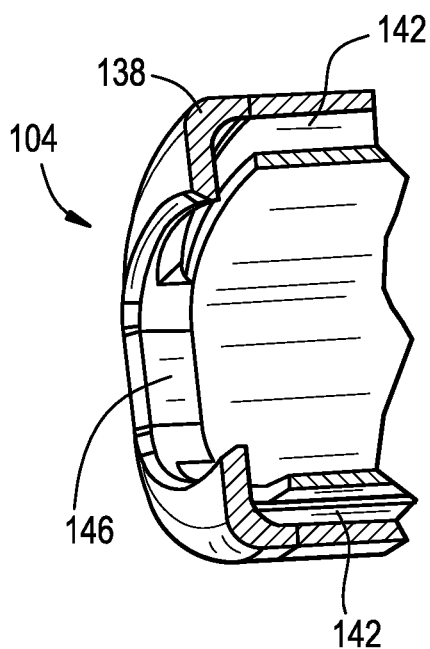
FIG. 11A is a sectional perspective view of another exemplary housing.
Figure 11B:
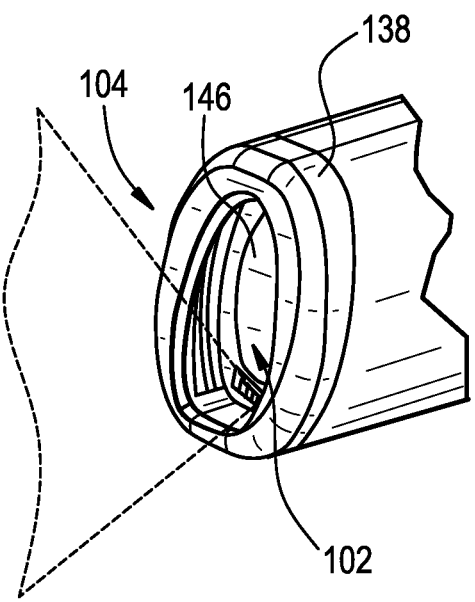
FIG. 11B is a perspective view of the housing of FIG. 11A.
Figure 11C:
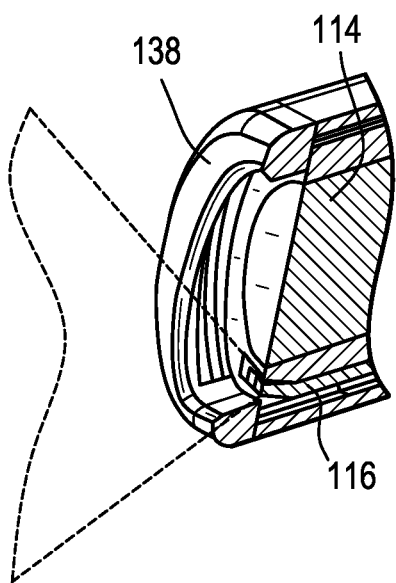
FIG. 11C is a sectional perspective view of the housing of FIG. 11A.
Figure 11D:
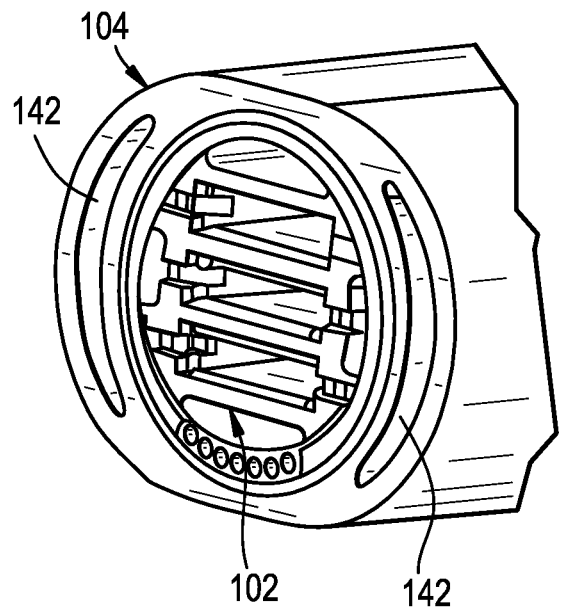
FIG. 11D is a sectional perspective view of the housing of FIG. 11A.

FIG. 10B illustrates another exemplary transverse cross-section of the housing 104. As shown, the fluid lumens 142 can be crescent or banana shaped. The fluid lumens 142 can have a convex inner sidewall that follows the outer periphery of the camera lumen 140.

FIGS. 11A-11D illustrate the distal end of an alternative housing 104 having crescent-shaped fluid lumens 142, an oval or oblong exterior transverse cross-section, and an end cap 138 with an oval or oblong central opening 146.

Figure 12A:
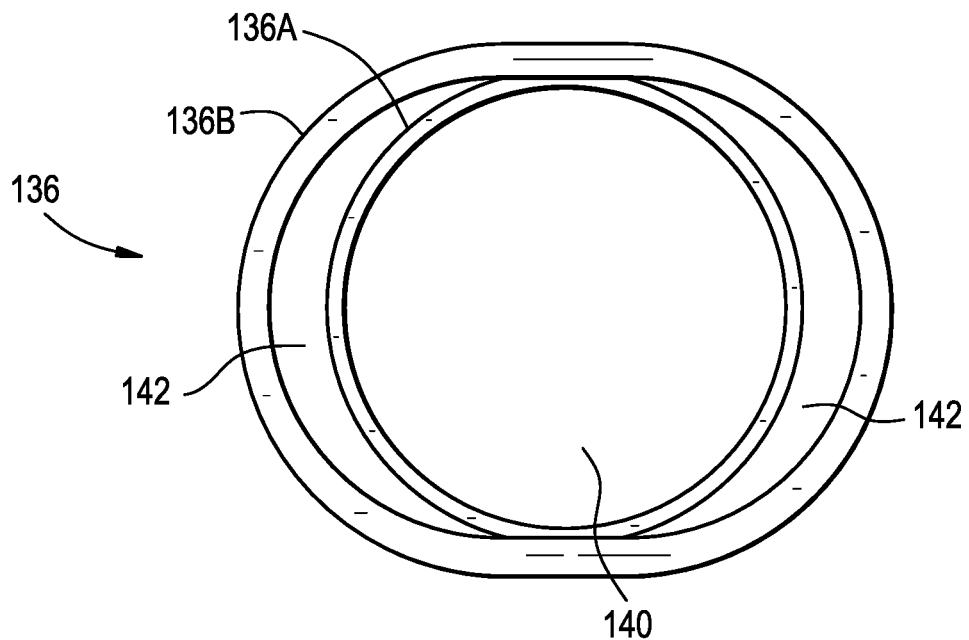
FIG. 12A is a sectional top view of another exemplary housing.
Figure 12B:
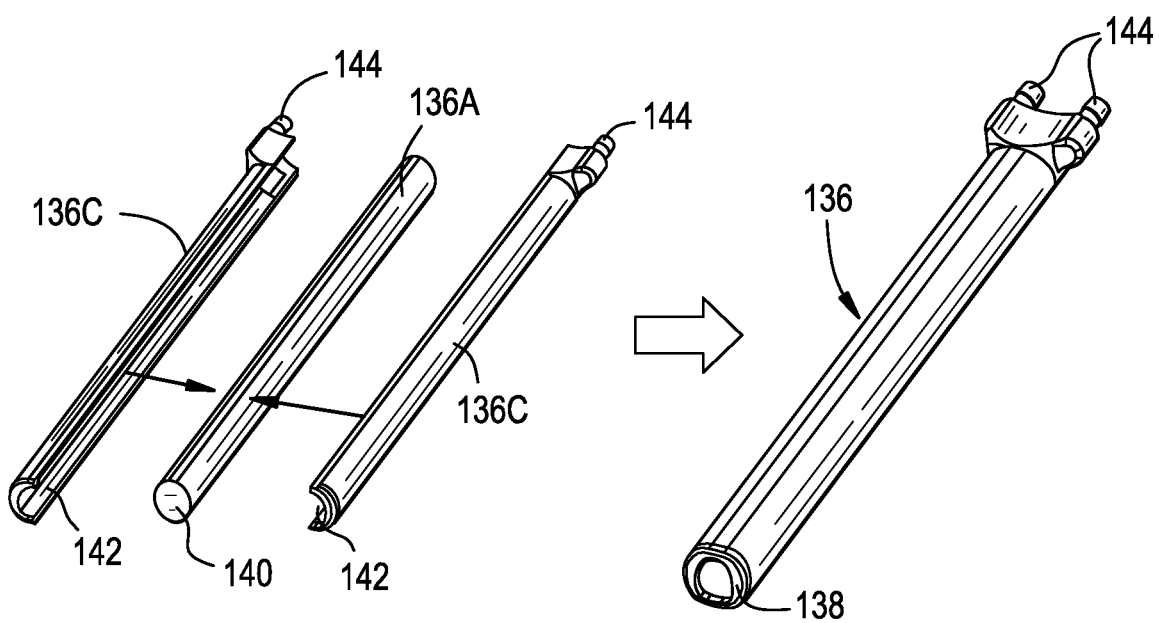
FIG. 12B is an exploded and assembled view of another exemplary housing.

As noted above, the main body 136 of the housing 104 can be formed by welding or otherwise attaching multiple longitudinal components to one another. For example, as shown in FIG. 12A, an inner circular tube 136A can be inserted into an outer oval tube 136B to define a main body 136 having a central camera lumen 140 and first and second lateral fluid lumens 142. The inner tube 136A can be welded, adhered, or otherwise attached and/or sealed to the outer tube 136B. By way of further example, as shown in FIG. 12B, opposed outer shells 136C can be welded or otherwise attached to an inner tube 136A to define a main body 136 having a central camera lumen 140 and first and second lateral fluid lumens 142. The outer shells 136C can include respective proximal fluid couplings 144 and inner channels that connect the fluid couplings to the void spaces 142 formed between the shells and the inner tube 136A when the components are mated to each other. The arrangement shown in FIG. 12B can advantageously allow a complex housing cross-section to be formed within one or more simple welds of the two shells 136C to the inner tube 136A and/or to each other.

Figure 13:
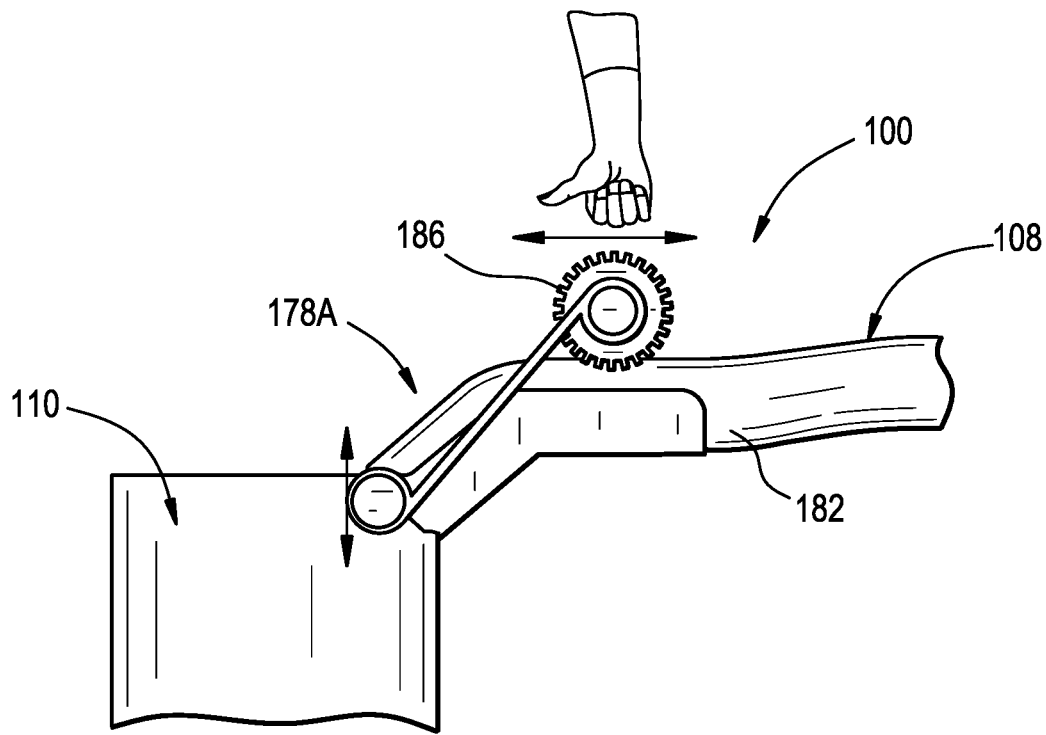
FIG. 13 is a side view of a mating feature that can be included in the access devices herein.

FIG. 13 illustrates an exemplary mating feature 178A for attaching the visualization system 100 to the access device 110. The mating feature 178A can include a proximal extension of the access device 110 having a track 182 for guiding or holding the connector assembly 108 of the visualization system 100. An actuation wheel or gear 186 can be rotatably mounted over the track 182. The wheel 186 can be engaged with the connector assembly 108 such that rotation of the wheel advances or retracts the connector assembly relative to the access device 110. The wheel 186 can allow for stageless and precise depth adjustment of the camera module 102. The wheel 186 can include teeth, protrusions, or other surface features for enhancing user grip and/or friction between the wheel and the connector assembly 108. The connector assembly 108 can include teeth or ridges that can be enmeshed with the teeth of the wheel 186. The wheel 186 can be spring-biased into engagement with the connector assembly 108. The gap between the wheel 186 and the track 182 can be open to one side, e.g., to allow side-loading of the connector assembly 108 into the gap. The user can thus perform gross depth adjustment of the camera module 102 in a freehand manner, and then insert the connector assembly 108 into the gap and use the wheel 186 to achieve fine depth adjustment.

Figure 14:
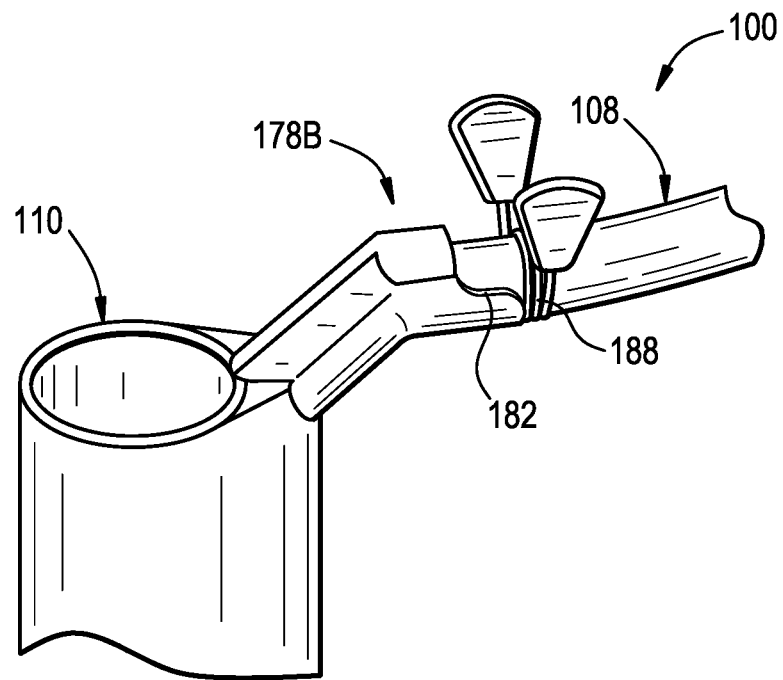
FIG. 14 is a perspective view of another mating feature that can be included in the access devices herein.

FIG. 14 illustrates an exemplary mating feature 178B for attaching the visualization system 100 to the access device 110. The mating feature 178B can include a proximal extension of the access device 110 having a track 182 for guiding or holding the connector assembly 108 of the visualization system 100. The mating feature 178B can include a clamp 188 that can be actuated by a user to selectively grasp or selectively release the connector assembly 108. Any of a variety of types of clamps can be used, though in the illustrated embodiment, the mating feature 178B includes a coil spring 188 that defines a central passage through which the connector assembly 108 can be inserted. The spring 188 can include handle levers that, when squeezed together, relax the tension of the spring and expand the diameter of the central passage to allow movement of the connector assembly 108 relative to the access device 110. When the levers are released, the tension in the spring 188 can be increased to contract the diameter of the central passage and clamp down on the connector assembly 108, thereby holding it in a fixed position relative to the access device 110.

Figure 15A:
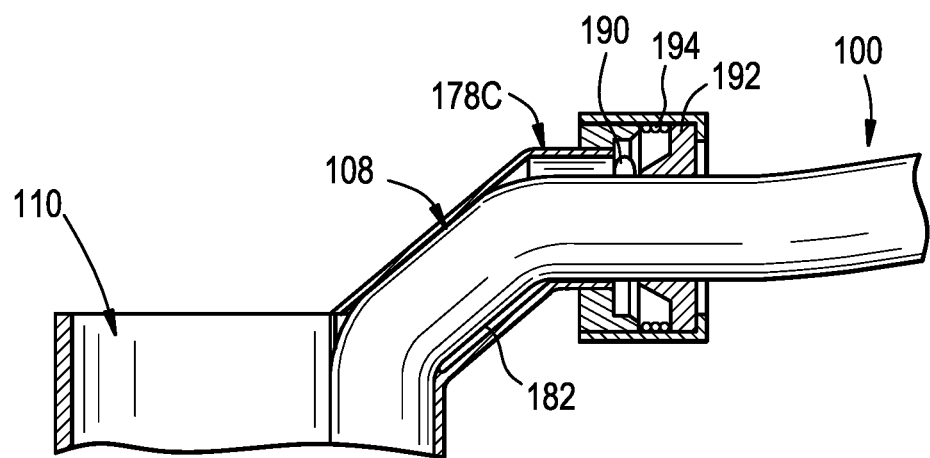
FIG. 15A is a sectional side view of another mating feature that can be included in the access devices herein, shown in locked state.
Figure 15B:
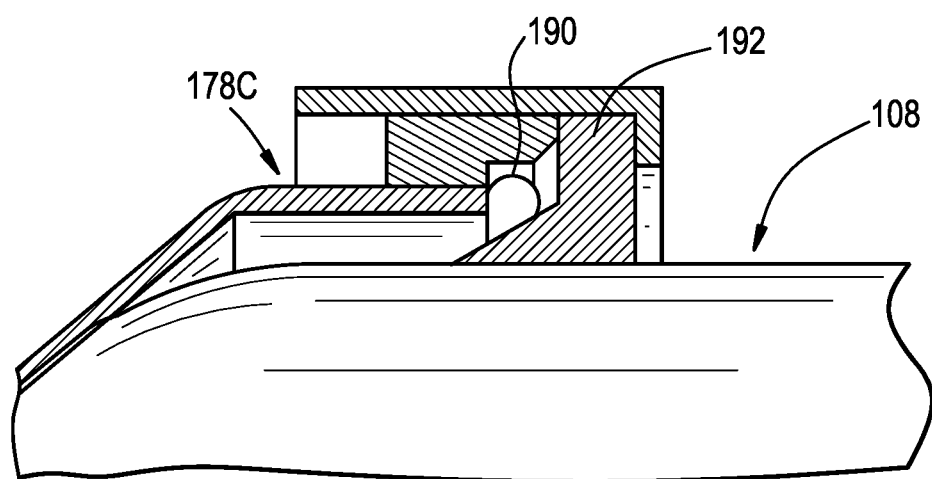
FIG. 15B is a sectional side view of the mating feature of FIG. 15A, shown in an unlocked state.

FIGS. 15A-15B illustrate an exemplary mating feature 178C for attaching the visualization system 100 to the access device 110. The mating feature 178C can include a proximal extension of the access device 110 having a track 182 for guiding or holding the connector assembly 108 of the visualization system 100. The mating feature 178C can include an O-ring 190 that defines a central passage through which the connector assembly 108 can be inserted. The O-ring 190 can be maintained in a fixed position relative to the extension 178C, such that when the O-ring clamps down on a connector assembly 108 inserted therethrough, the connector assembly can be maintained at a fixed position relative to the extension. The extension 178C can include a movable button 192 with a conical or ramped bearing surface. As shown in FIG. 15B, pressing the button 192 into the extension 178C (to the left in the drawing) can be effective to wedge the cone of the button into the O-ring 190, thereby expanding the diameter of the O-ring and allowing movement of the connector assembly 108 relative to the extension. As shown in FIG. 15A, when the button 192 is released, a spring 194 can urge the button outward (to the right in the drawing), withdrawing the cone from the O-ring 190 to allow the O-ring diameter to contract and clamp down on the connector assembly 108, thereby holding it in a fixed position relative to the access device 110.

Figure 16A:
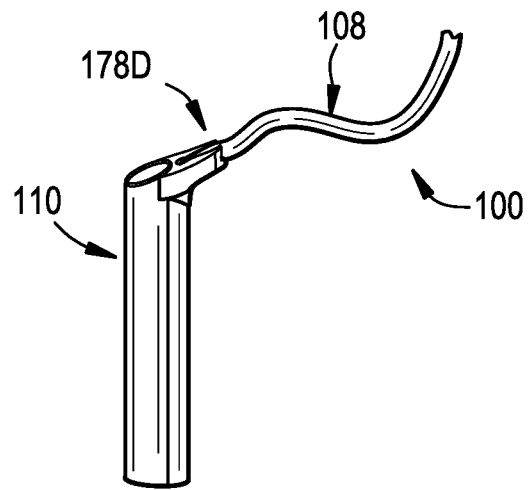
FIG. 16A is a perspective view of another mating feature that can be included in the access devices herein.
Figure 16B:
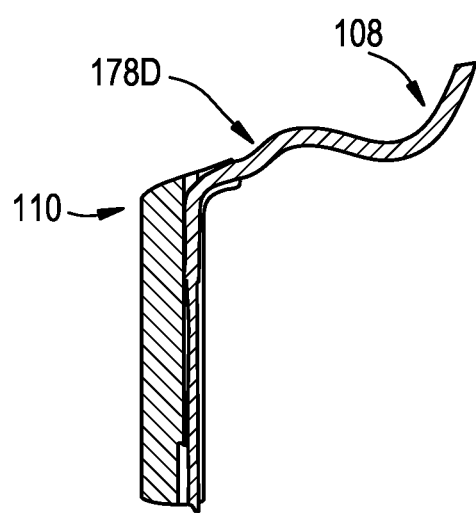
FIG. 16B is a sectional side view of the mating feature of FIG. 16A.
Figure 16C:
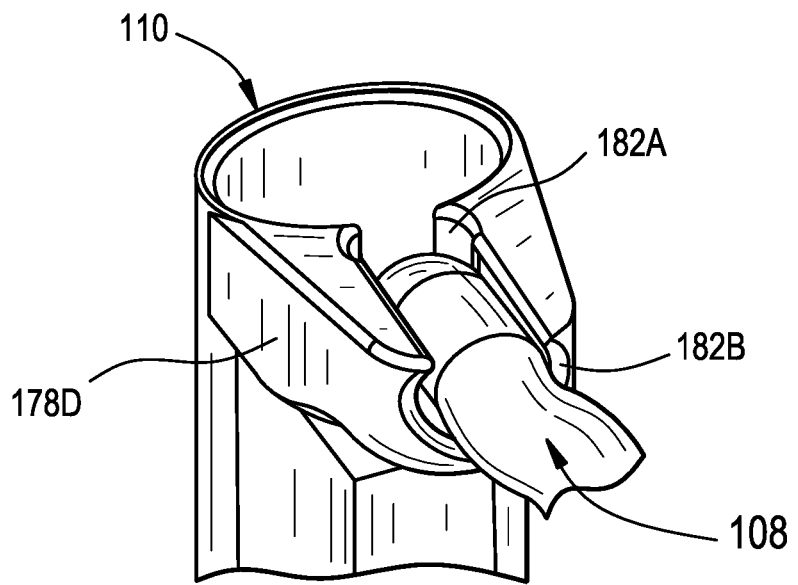
FIG. 16C is a perspective view of the mating feature of FIG. 16A.

FIGS. 16A-16C illustrate an exemplary mating feature 178D for attaching the visualization system 100 to the access device 110. The mating feature 178D can include a proximal extension of the access device 110 having a track 182 for guiding or holding the connector assembly 108 of the visualization system 100. The mating feature 178D can be an angled click-type fastening system of the type described above. The mating feature 178D can be optimized for use with a connector assembly 108 having a circular exterior transverse cross-section. The mating feature 178D can include a longitudinally-oriented adjustment track 182A and an obliquely- or laterally-oriented locking track 182B.

Figure 17:
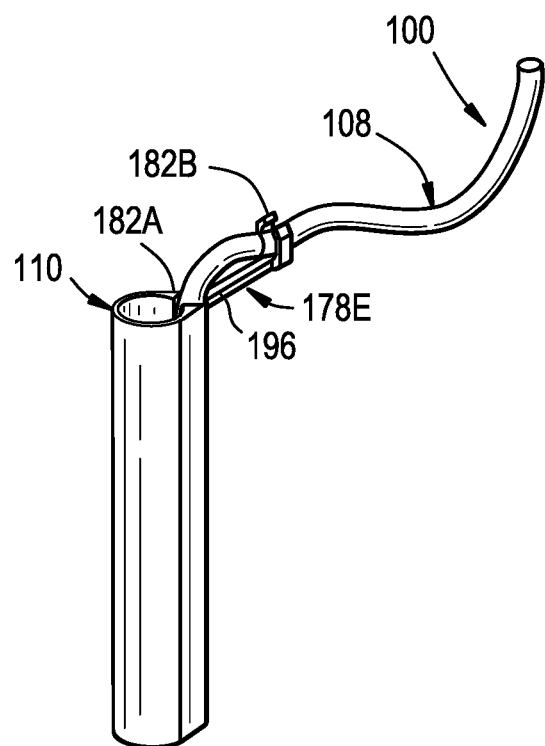
FIG. 17 is a perspective view of another mating feature that can be included in the access devices herein.

FIG. 17 illustrates an exemplary mating feature 178E for attaching the visualization system 100 to the access device 110. The mating feature 178E can include a proximal extension of the access device 110 having a track 182 for guiding or holding the connector assembly 108 of the visualization system 100. The mating feature 178E can be an angled click-type fastening system of the type described above. The mating feature 178E can include a longitudinally-oriented adjustment track 182A and an obliquely- or laterally-oriented locking track 182B. The locking track 182B can be spaced a distance apart and radially-outward from the main body of the access device 110 by a strut or beam 196. The mating feature 178E can be configured to contact the connector assembly 108 only at the locking track 182B. The mating feature 178E can be simple to manufacture and can accommodate a gradual bend radius of the connector assembly 108.

Figure 18:
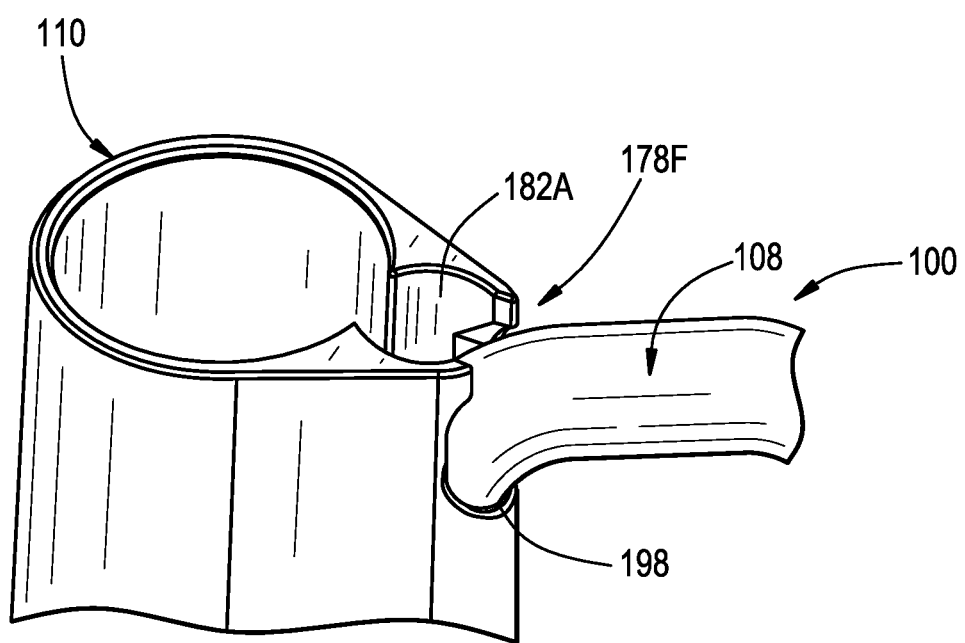
FIG. 18 is a perspective view of another mating feature that can be included in the access devices herein.

FIG. 18 illustrates an exemplary mating feature 178F for attaching the visualization system 100 to the access device 110. The mating feature 178F can include a cut-out 198 formed in the proximal edge of the access device 110. The mating feature 178F can be a click-type fastening system of the type described above. The connector assembly 108 can be positioned within a longitudinally-oriented adjustment track 182A of the mating feature 178F to allow depth adjustment of the camera module 102. The connector assembly 108 can be urged out of the adjustment track 182A and into the cut-out 198 to apply sufficient friction to the connector assembly to limit or prevent depth adjustment of the camera module 102. The cut-out 198 can be U-shaped. The cut-out 198 can be V-shaped. The mating feature 178F can allow the connector assembly 108 to be routed away from the access device 110 at a greater angle and closer to the skin surface of the patient, reducing the overall profile of the system 100 and keeping the connector assembly out of the way of the surgeon or other user.

Figure 19:
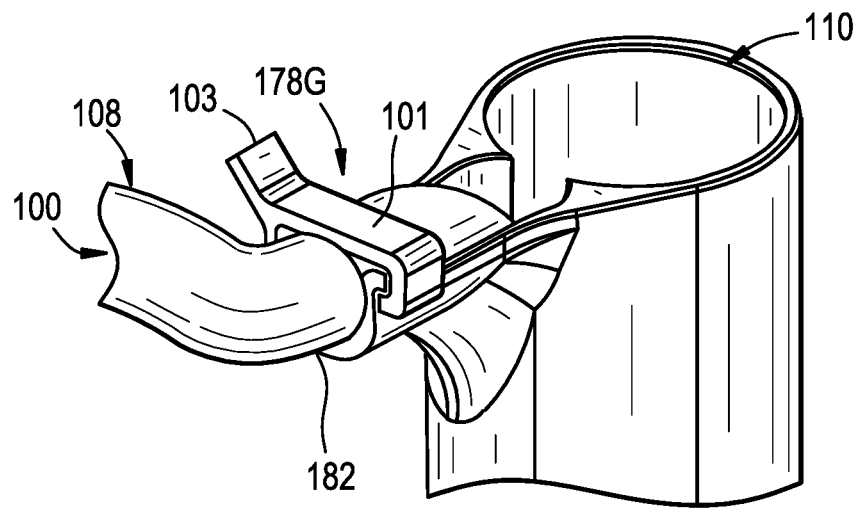
FIG. 19 is a perspective view of another mating feature that can be included in the access devices herein.

FIG. 19 illustrates an exemplary mating feature 178G for attaching the visualization system 100 to the access device 110. The mating feature 178G can include a proximal extension of the access device 110 having a track 182 for guiding or holding the connector assembly 108 of the visualization system 100. The mating feature 178G can include a lid or closure cap 101 pivotably coupled thereto, e.g., via a living hinge or flexible material properties of the extension. The lid 101 can be positioned in a closed state in which it clamps the connector assembly 108 to the extension to limit or prevent depth adjustment of the camera module 102. The lid 101 can be positioned in an open state in which it does not engage the connector assembly 108, or engages the connector assembly to a lesser degree, such that the connector assembly is movable relative to the extension to adjust the depth of the camera module 102. The lid 101 can be retained in the closed state, e.g., via a snap-lock, click-lock, or other locking structure. The lid 101 can include a lever 103 to facilitate release of the lid from the closed state.

Figure 20:
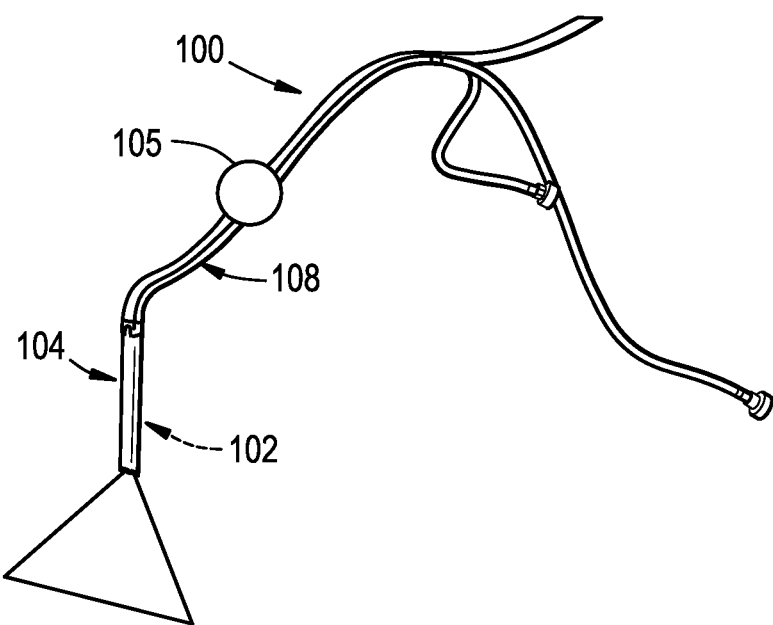
FIG. 20 is a perspective view of the system of FIG. 1, shown with a user control.

As shown in FIG. 20, the visualization system 100 can include a user control 105. The user control 105 can be disposed at any of a variety of locations along the visualization system 100, e.g., along a distal portion of the connector assembly 108 as shown. During use, the user control 105 can be positioned within the sterile field. This can allow a surgeon or other user to actuate the control 105 directly, without having to leave the sterile field or rely on an assistant outside the sterile field. The control 105 can be operably coupled to the camera module 102, to the controller 106, to the fluid source 168, to the light source 170, and/or to the suction source 172. Actuation of the control 105 can be effective to initiate a cleaning operation, to stop a cleaning operation, to capture an image, to rotate a display of images captured by the camera module 102, to adjust a white balance of the displayed images, to adjust a brightness of the displayed images, to play or stop a recorded video, to zoom the displayed images in or out (optically and/or digitally), etc. The control 105 can include one or more push buttons. The control 105 can include one or more foot switches. The control 105 can include a hand pump or syringe for directing cleaning media towards the camera module 102. The control 105 can include a remote control integrated into the connector assembly 108. The control 105 can include a remote control coupled to the controller 106 via a wired or wireless connection.

The access devices disclosed herein can be inserted into a patient using various dilation techniques. In an exemplary method, a guidewire or needle can be inserted through a percutaneous incision in the patient. The guidewire can be placed using fluoroscopic guidance, a surgical navigation system, freehand, or otherwise. The incision can be sequentially or serially dilated, for example by inserting one or more dilators over the guidewire, each having a progressively larger outside diameter. Once sufficiently dilated, the access device can be inserted by placing the outer-most dilator into the working channel of the access device and sliding the access device distally along the dilator and into the patient. The one or more dilators can then be removed from the patient, leaving an open working channel through the access device through which the surgical procedure can be conducted.

Figure 21A:
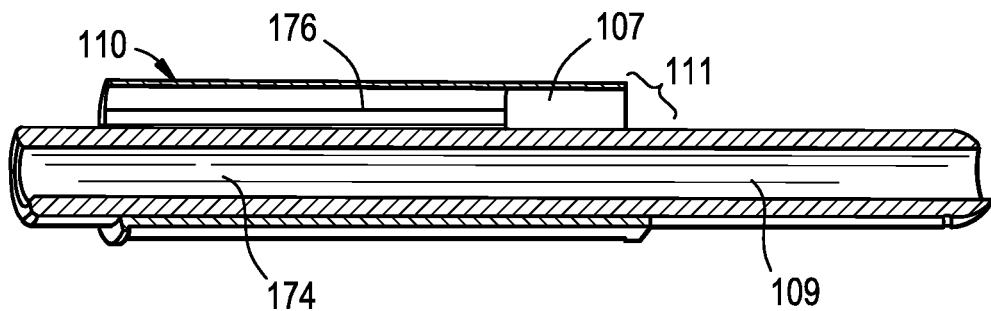
FIG. 21A is a sectional perspective view of an access device and a standard dilator.

There can be instances in which it may be necessary or desirable to augment standard cylindrical dilation techniques. For example, as shown in FIG. 21A, an access device 110 can include a cylindrical working channel 174 and an offset visualization channel 176. The access device 110 can have a non-cylindrical exterior dimension. The visualization channel 176 can terminate a distance apart from the distal end of the access device 110, leaving a void space 107 within the access device distal to the visualization channel. As shown, when a standard cylindrical dilator 109 is inserted through the working channel 174, a sharp transition or step 111 can exist at the distal end of the access device 110 between the outer surface of the dilator and the outer surface of the access device adjacent the visualization channel 176. In this example and/or in others, a dilation system can be used to facilitate insertion of the access device 110 and dilation of tissue disposed in the path of the visualization channel 176.

Figure 21B:
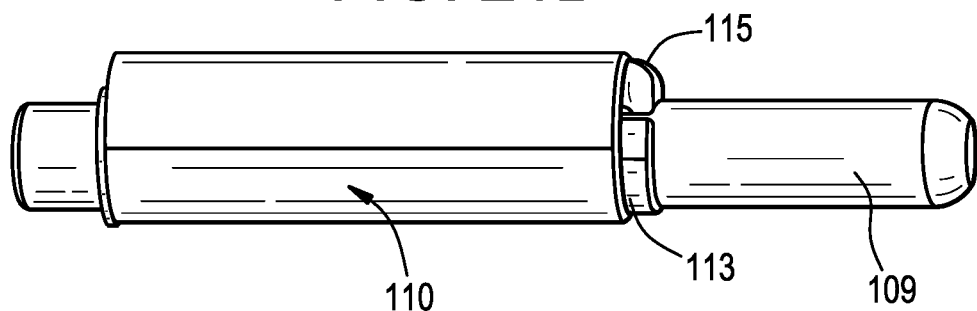
FIG. 21B is a perspective view of an access device and a dilation system.
Figure 21C:
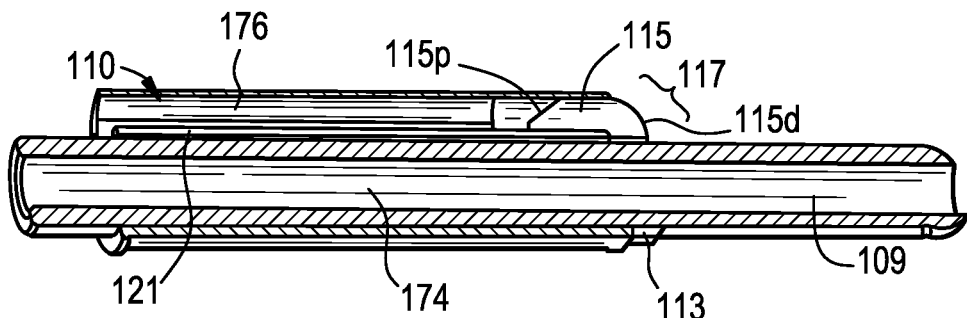
FIG. 21C is a sectional perspective view of the access device and dilation system of FIG. 21B.
Figure 21D:
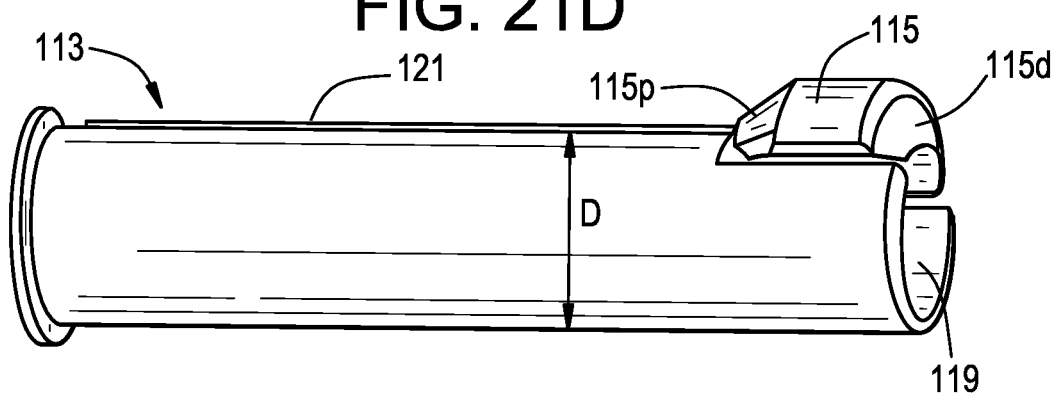
FIG. 21D is a perspective view of a sleeve of the dilation system of FIG. 21B.

FIGS. 21B-21D illustrate an exemplary dilation system. As shown, the system can include a sleeve 113 with a bulb 115 movably coupled thereto. When the sleeve 113 is disposed in the working channel 174 of the access device 110, the bulb 115 can occupy the void space 107 in the access device and provide a smooth transition 117 between the outer surface of the dilator 109 and the outer surface of the access device adjacent the visualization channel 176. Accordingly, the bulb 115 can minimize or eliminate the above-described step 111.

The sleeve 113 can be substantially cylindrical. The sleeve 113 can be hollow to define a channel 119 through which a standard cylindrical dilator 109 can be inserted. The sleeve 113 can define an outside diameter D. The bulb 115 can be movable relative to the sleeve 113 between a first position in which the bulb is disposed entirely within the outside diameter D of the sleeve and a second position in which at least a portion of the bulb protrudes out from the outside diameter D of the sleeve. The bulb 115 can be biased towards the second position. The bulb 115 can be attached to or formed integrally with the sleeve 113. The bulb 115 can be attached to the sleeve by a spring. For example, the bulb 115 can be mounted at the distal end of a longitudinal leaf spring or flat spring 121 of the sleeve 113. The spring 121 can be an integral extension of the sleeve 113 defined between opposed longitudinal slits formed in the sleeve. The bulb 115 can include a distal-facing surface 115d that is ramped, curved, tapered, or otherwise configured to provide a smooth lead-in between the outside diameter of a dilator 109 disposed in the sleeve 113 and the outside diameter of the access device 110. The bulb 115 can include a proximal-facing surface 115p that is ramped, curved, tapered, or otherwise configured to urge the bulb radially-inward towards the first position as the sleeve 113 is withdrawn proximally from the access device 110.

In use, an incision can be sequentially dilated using standard cylindrical dilators, including an outermost dilator 109. The sleeve 113 can be loaded into the access device 110 with the bulb 115 disposed in the first, radially-inward position. The sleeve 113 can be advanced distally relative to the access device 110 until the bulb 115 is at the depth of the void space 107, at which point the bulb can move radially-outward to the second position under the bias of the spring 121. The bulb 115 can also be urged radially-outward, and maintained in that position, by insertion of a dilator 109 through the sleeve 113. The access device 110 with the inserted sleeve 113 can then be advanced distally over the outer-most dilator 109. As the access device 110 is advanced distally, the distal-facing surface 115d of the bulb 115 can gently urge tissue out of the path of the access device. Once the access device 110 is positioned as desired, the dilators 109 can be removed from the sleeve 113 by withdrawing the dilators proximally therefrom. The sleeve 113 can also be removed from the access device 110 by withdrawing the sleeve proximally therefrom. As the sleeve 113 is withdrawn proximally relative to the access device 110, the bulb 115 can be urged radially-inward, e.g., by the proximal-facing surface 115p of the bulb 115 bearing against the distal end of the visualization channel 176, thereby moving the bulb to the first, radially-inward position to allow the sleeve to be removed from the access device. The sleeve 113 can form a dilator having a profile at its distal end that differs from its profile at its proximal end.

Figure 22A:
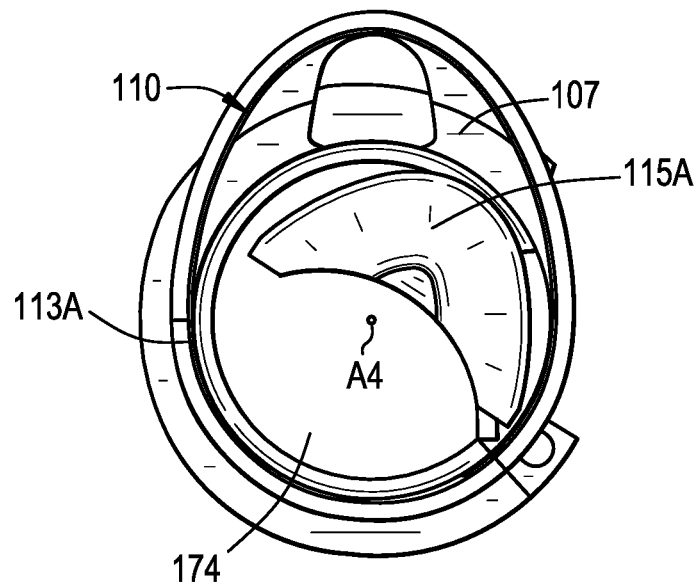
FIG. 22A is a proximal-facing end view of an access device and a dilation system in a first configuration.
Figure 22B:
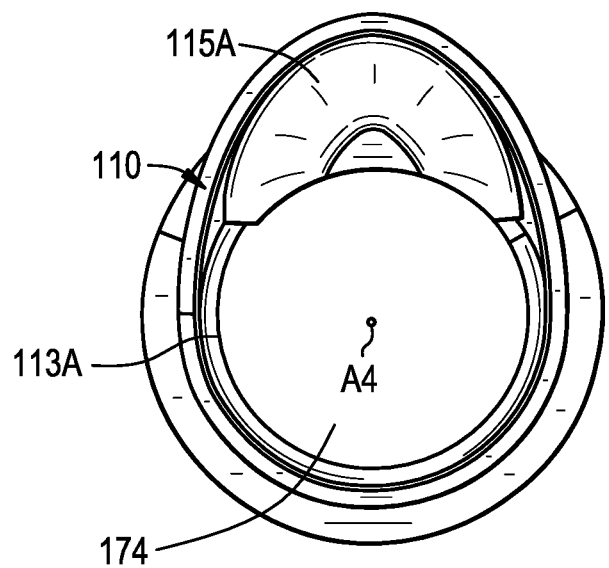
FIG. 22B is a proximal-facing end view of the access device and dilation system of FIG. 22A in a second configuration.
Figure 23A:
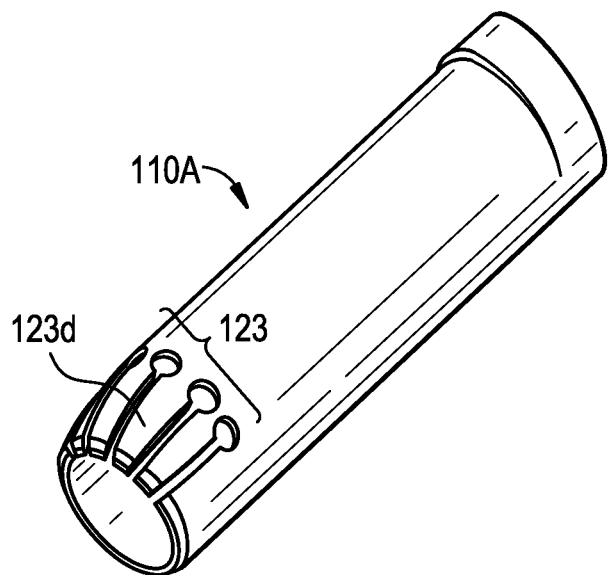
FIG. 23A is a perspective view of an access device.
Figure 23B:
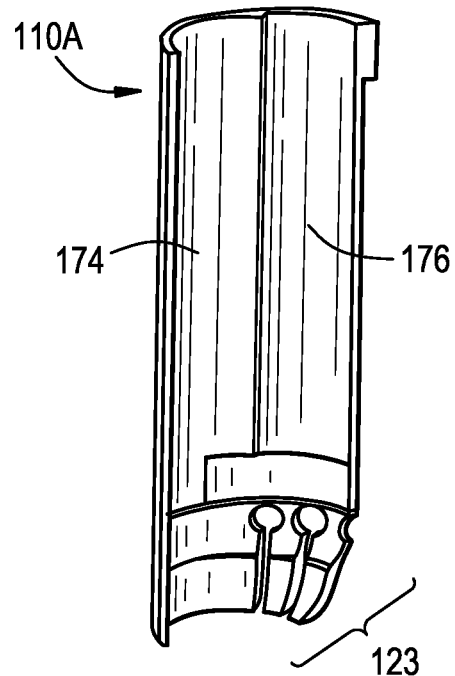
FIG. 23B is a sectional perspective view of the access device of FIG. 23A.
Figure 23C:
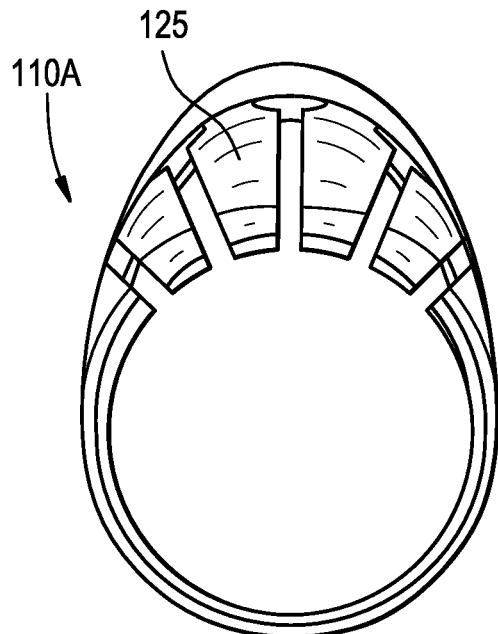
FIG. 23C is a bottom view of the access device of FIG. 23A.
Figure 23D:
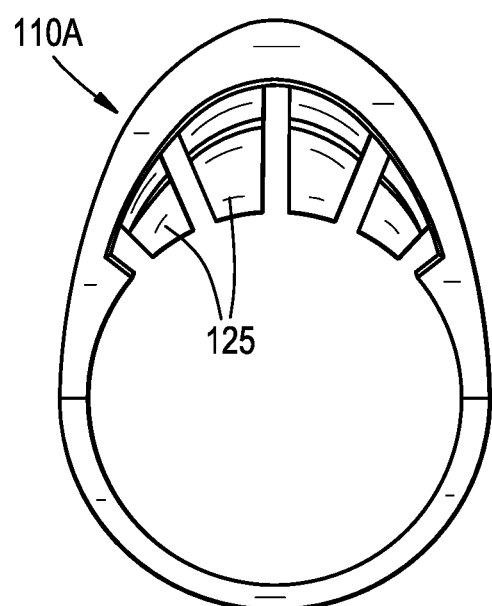
FIG. 23D is a top view of the access device of FIG. 23A.
Figure 23E:
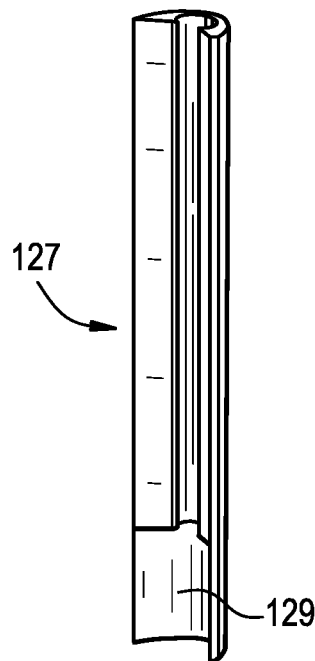
FIG. 23E is a perspective view of a dilation shaft configured for use with the access device of FIG. 23A.
Figure 23F:
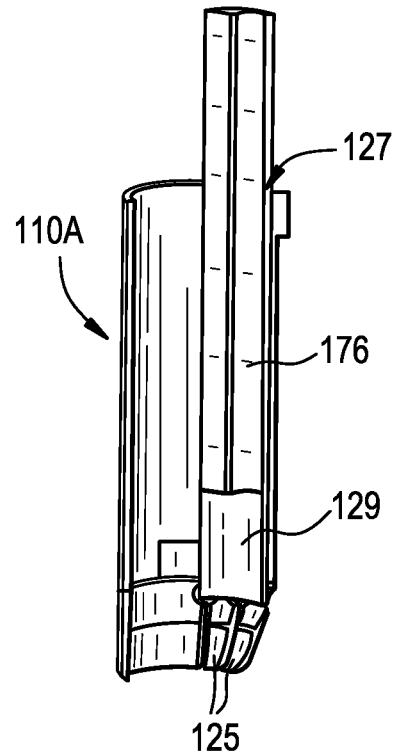
FIG. 23F is a sectional perspective view of the dilation shaft of FIG. 23E inserted into the access device of FIG. 23A.
Figure 23G:
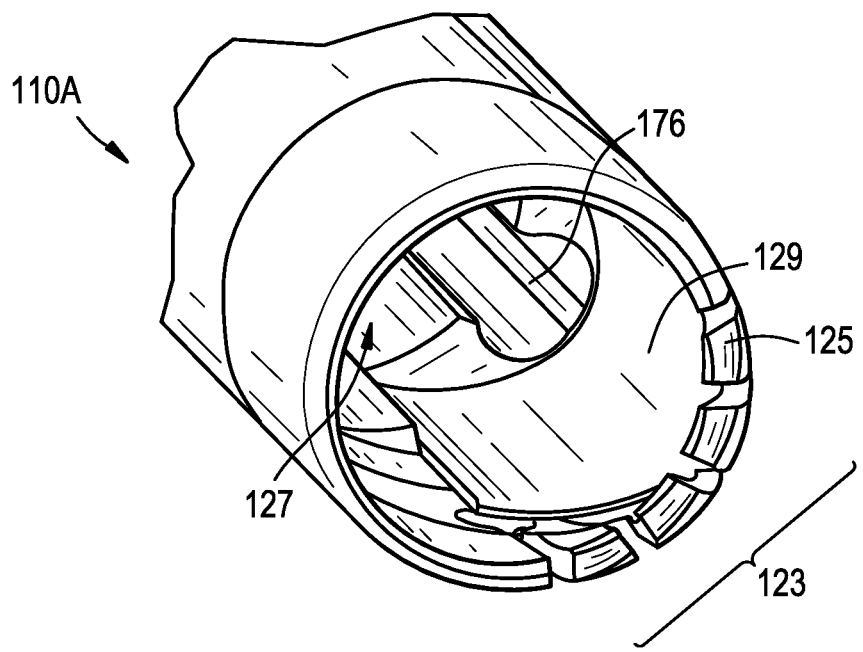
FIG. 23G is a perspective view of the dilation shaft of FIG. 23E inserted into the access device of FIG. 23A.

FIGS. 22A-22B illustrate another exemplary dilation system in which the sleeve 113A is configured to rotate relative to the access device 110 about the central longitudinal axis A4 of the working channel 174. The sleeve 113A can have a longitudinal slit or other features for allowing the sleeve to expand and contract radially. The sleeve 113A can be radially-contracted upon insertion into the access device 110 to bias the bulb 115A radially-outward. The sleeve 113A can be rotatable about the axis A4 between a first position, shown in FIG. 22A, in which the bulb 115 is rotationally offset from the void space 107 and thus deflected radially-inward by the inner sidewall of the working channel 174, and a second position, shown in FIG. 22B, in which the bulb is rotationally aligned with the void space such that the bulb springs radially-outward to fill the void space. In the first position, the bulb 115A can be positioned such that it does not interfere with insertion or removal of the sleeve 113A from the access device 110. In the second position, the bulb 115A can fill the void space 107 to provide a smooth transition between a dilator and the access device 110, e.g., as described above. The sleeve 113A can form a dilator having a profile at its distal end that differs from its profile at its proximal end.

FIGS. 23A-23G illustrate another exemplary dilation system. As shown, the distal end of the access device 110A can include a ramped, curved, or tapered transition portion 123 that provides a smooth transition between a cylindrical dilator inserted through the working channel 174 of the access device and the outside surface of the access device adjacent the visualization channel 176. The transition portion 123 can be flexible or bendable. The transition portion 123 can be movable between a first position in which the transition portion extends radially-inward to provide a smooth distal-facing dilation surface 123d and a second position in which the transition portion is moved radially-outward from the first position so as not to obstruct the field of view of a camera module mounted in the access device 110A. The transition portion 123 can include one or more movable fingers 125. The fingers 125 can be defined by a plurality of longitudinal slits formed in the outer wall of the access device 110A. The fingers 125 can have resilient material properties, such that they are biased inwards towards the first position.

The transition portion 123 can be moved between the first and second positions by a dilation shaft 127 insertable through the access device 110A. The dilation shaft 127 can include a distal shroud 129 configured to contact and bear against the transition portion 123 as the dilation shaft is advanced distally within the access device 110A to urge the transition portion radially outward. The shroud 129 can form a section of a cylinder as shown. At least a portion of the visualization channel 176 can be formed in the dilation shaft 127. The dilation shaft 127 can remain in place within the access device 110 when the camera module 102 is disposed in the access device and as the surgical procedure is performed.

Figure 24A:
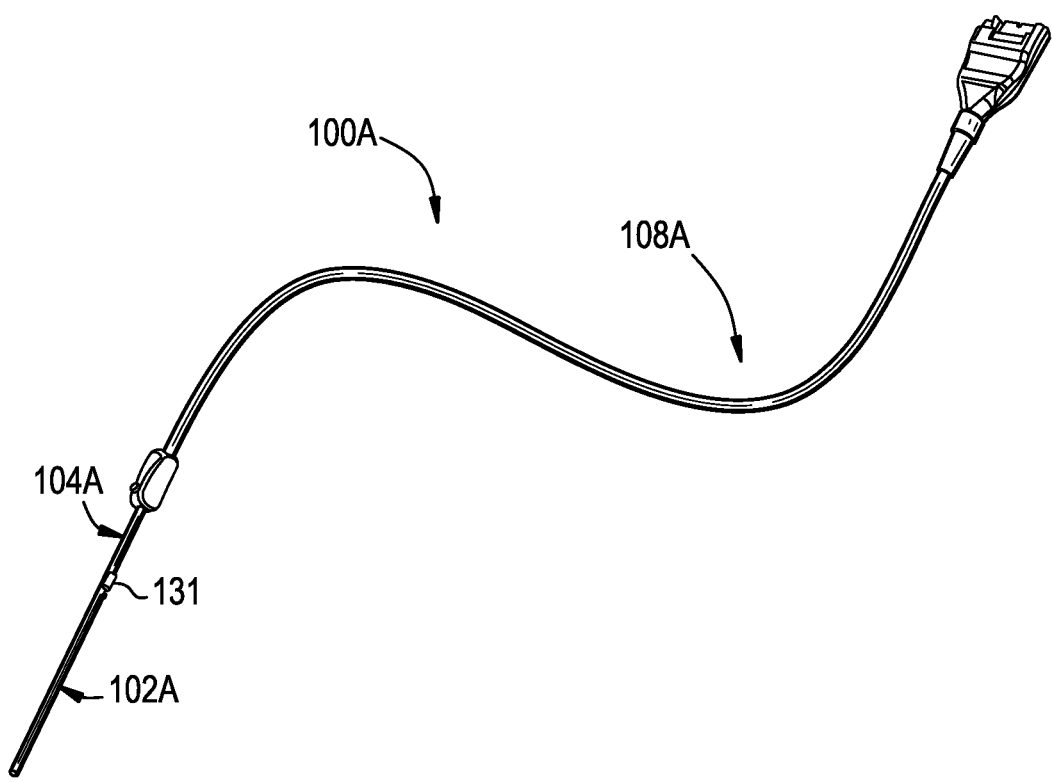
FIG. 24A is a perspective view of a visualization system.
Figure 24B:
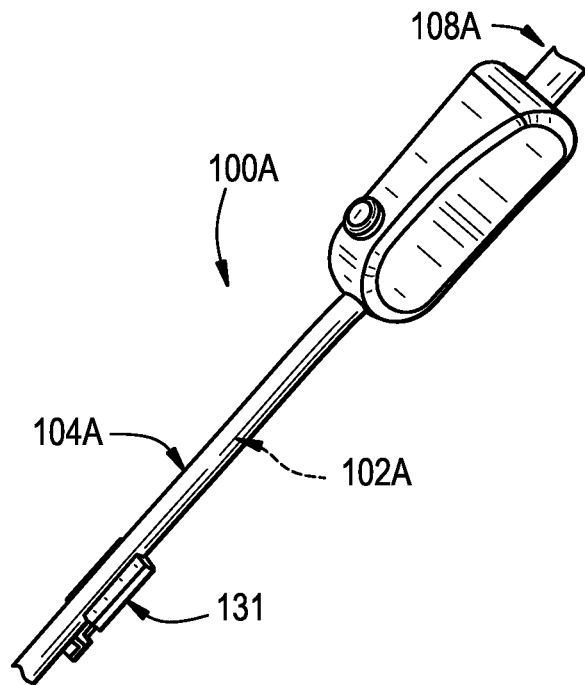
FIG. 24B is a perspective view of a housing, camera module, and mating feature of the visualization system of FIG. 24A.
Figure 24C:
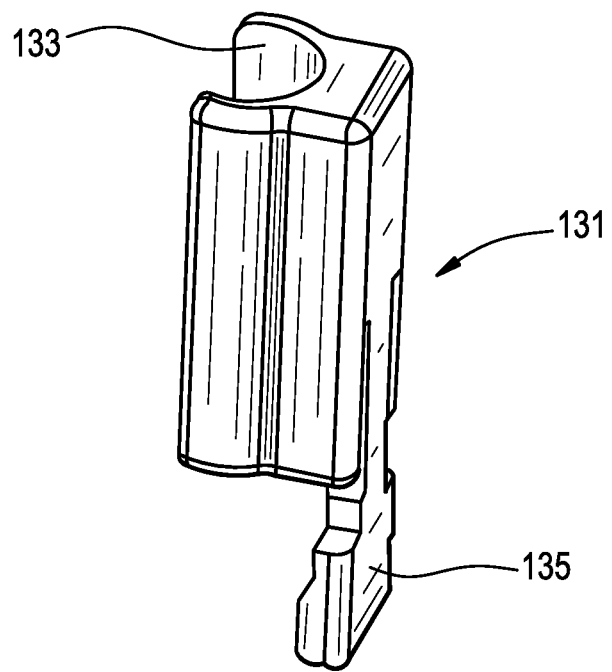
FIG. 24C is a perspective view of the mating feature of the visualization system of FIG. 24A.

FIGS. 24A-24C illustrate an auxiliary visualization system 100A. The system 100A can be used independently, or can be used with the visualization system 100 described above. The system 100A can include a camera module 102A, housing 104A, and connector assembly 108A, each of which can include any of the features of the corresponding components of the system 100. The system 100A can be used as a freehand stylus-type or wand-type camera. The system 100A can be inserted through a working channel of an access device while the system 100 is inserted through a visualization channel of the access device. Both cameras 100, 100A can be coupled to the same controller or display, or each can be coupled to an independent controller or display. Multiple auxiliary cameras 100A can be used simultaneously. In the case of a spinal surgery, the auxiliary camera 100A can extend into the disc space and the primary camera 100 can remain within the access device. The auxiliary camera 100A can be attached to the access device using a mating feature 131. The mating feature 131 can be configured to hold or support the auxiliary camera 100A relative to an access device. The mating feature 131 can allow hands-free operation of the auxiliary camera 100A. As shown in FIG. 24C, the mating feature 131 can include a C-shaped clip or other mechanism 133 for attaching to the housing or connector assembly of the auxiliary camera 100A. The mating feature 131 can include any of the features described above with respect to mating features for attaching the visualization system 100 to an access device. The mating feature 131 can include a distal clip or springy strip 135 for attaching the mating feature to the proximal rim of an access device.

The visualization systems and/or access devices disclosed herein can be used in any of a variety of surgical procedures. For example, such systems and devices can be used in ear, nose, and throat (ENT) surgery, sinus surgery, gastrointestinal (GI) surgery, abdominal surgery, intravascular surgery, cardiothoracic surgery, joint surgery, and so forth. In some embodiments, the visualization system can be used, with or without an access device, as a self-cleaning endoscope for sinus surgery. Active and/or passive cleaning features of the system can reduce or eliminate the need to repeatedly withdraw the scope from the patient to clean the lens. In some embodiments, the visualization system can be used, with or without an access device, as a self-cleaning endoscope for airway surgery (e.g., laryngoscopy, bronchoscopy, etc.). In some embodiments, the visualization system can be used, with or without an access device, as a self-cleaning upper and/or lower GI scope. The visualization system can form a rigid endoscope with self-cleaning abilities.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A visualization system, comprising:
a camera module having an image sensor and a lens; and
a housing in which the camera module is disposed, the housing having a main body, and a distal end cap, the main body includes a distal end with a distal-facing surface, a camera lumen therein in which the camera module is disposed, and first and second fluid lumens, and the distal end cap includes a proximal-facing surface including a first portion that is configured to abut the distal-facing surface of the main body, and
wherein a second portion of the proximal-facing surface of the distal end cap and the distal-facing surface of the main body defines a fluid passageway therebetween configured to direct fluid flowing out of the first fluid lumen of the housing across the lens of the camera module,
wherein, the distal end includes a convex side and a non-convex side,
when the first portion of the proximal-facing surface abuts the distal-facing surface of the main body, the outer periphery of the distal end cap defines a convex side coextensive with the convex side of the main body and a cut out extending through the distal end cap from the non-convex side of the main body towards the camera lumen, and
a portion of the cut out is axially aligned with the camera lumen.

2. The system of claim 1, wherein a central region of the lens is coated with hydrophobic coating and a peripheral region of the lens is coated with a hydrophilic coating.

3. The system of claim 1, wherein the camera module is disposed centrally in the main body, between the first and second fluid channels.

4. The system of claim 1, wherein a distal facing surface of the main body and a distal facing surface of the distal end cap are obliquely angled relative to a central longitudinal axis of the camera module.

5. The system of claim 1, wherein the main body has an outer surface that includes first and second planar regions connected by a central transition region that defines a section of a cylinder, the transition region following an outer perimeter of a camera lumen of the main body.

6. The system of claim 5, wherein the main body has an inner surface that is concavely curved and connected to the outer surface by first and second transition regions that define sections of respective cylinders, the first and second transition regions following the outer perimeters of the first and second fluid channels.

7. The system of claim 1, wherein the cut-out is axially aligned with the lens.

8. The system of claim 7, wherein the proximal-facing surface of the distal end cap defines a recess configured to direct fluid flowing out of the first fluid channel of the housing across the lens and into the second fluid channel of the housing.

9. The system of claim 8, wherein the recess includes lateral end portions axially aligned with the first and second fluid channels and medial endportions that are open to the cut-out of the distal end cap.

10. The system of claim 1, further comprising a connector assembly extending from the housing, the connector assembly including electrical and optical connections to the camera module and fluid connections to the housing.

11. The system of claim 10, wherein the connector assembly has an exterior shape that matches that of the housing.

12. The system of claim 1, wherein the non-convex side of the distal end of the main body has a sidewall having a concave inner surface disposed adjacent the working channel and the convex side of the distal end of the main body has a convex outer surface disposed opposite the inner surface.

\* \* \* \* \*